United States Patent [19]

Hanessian

[11] Patent Number: 5,767,256
[45] Date of Patent: Jun. 16, 1998

[54] SOLUTION AND SOLID PHASE STEREOCONTROLLED GLYCOSIDATION

[76] Inventor: Stephen Hanessian, 65 Gables Court, Beaconsfield Quebec, Canada, H9W 5H3

[21] Appl. No.: 403,813

[22] PCT Filed: Jul. 19, 1994

[86] PCT No.: PCT/GB94/00396

§ 371 Date: Mar. 14, 1995

§ 102(e) Date: Mar. 14, 1995

[87] PCT Pub. No.: WO95/03316

PCT Pub. Date: Feb. 2, 1995

[30] Foreign Application Priority Data

Jul. 19, 1993 [CA] Canada ................................. 2100821

[51] Int. Cl.⁶ .............................. C07H 1/00; C07H 15/00
[52] U.S. Cl. .................................. 536/18.6; 536/25.3
[58] Field of Search ............................. 536/18.6, 25.3

[56] References Cited

PUBLICATIONS

Hanessian *Carbohydrate Research* 1980, 80, C17–C22.
Chemical Abstracts, vol. 107, No. 23, 1987, Columbus, Ohio, U.S.; Abstract No. 217957, Nikolaev, A.V., Use of 2-pyridyl 2,3,4,6-tetra-O-benzyl-beta-D-glucoside in the synthesis of 1,2-cis-bonded disaccharides, p. 625.

Tetrahedron, vol. 47, 1991, Vankar, Y.D., Synthesis of beta-O-glycosides, pp. 9985-9992, compound 3 (see Table 1).

Chemistry Letters, Apr. 4, 1994, Mukaiyama, T., Stereoselective synthesis of alpha-ribonucleosides, pp. 557-560.

Chemistry Letters, 1979, Shoda, S. et al. A new method for the synthesis of beta-glucosides, pp. 847-848.

Tetrahedron, vol. 47, 1991, Mereyala, H.B., Stereoselective synthesis of alpha-linked saccharides, pp. 6435-6448.

Tetrahedron, vol. 48, 1992, Garner, P., Synthesis of 2-aminopurine nucleosides, pp. 4259-4270.

Tetrahedron Letters, vol. 32, 1991, Knapp, S., Nucleoside synthesis from thioglycosides, pp. 3627-3630.

*Primary Examiner*—Kathleen K. Fonda
*Attorney, Agent, or Firm*—McFadden, Fincham

[57] ABSTRACT

Novel glycosides containing novel leaving groups, pyridyloxy, pyrimidyloxy, methoxypyridyloxy, pyridyl carbonate and pyridyl thiocarbonate are utilized in many fertile syntheses of glycosides, disaccharides, trisaccharides, oligosaccharides, nucleosides and the like. These synthetic schemes are superior in stereospecificity, yield and speed of preparation of numerous novel compounds. Polymer supported syntheses may be utilized within the general scheme to provided enhanced product purity.

19 Claims, No Drawings

SOLUTION AND SOLID PHASE STEREOCONTROLLED GLYCOSIDATION

This application is the U.S. national stage entry under 35 U.S.G. 371 of PCT/CA94/00396, filed Jul. 19, 1994.

The requirement to produce pure stereospecific products is the core, pith and marrow of carbohydrate chemistry. Particularly essential is the requirement to produce pure(r) alpha and beta anomers (C-1 anomers in D- and L-sugars). Optimized yield of the compound and proportion of alpha anomer are both highly desirable, as those skilled in the art would appreciate, for practical and commercial reasons.

The present invention primarily relates to a process of providing pure, or significantly higher proportion of alpha anomers in significantly improved yield. Specific donors, acceptors, promoters, and solvents are combined to produce specific anomers. The present invention secondarily provides novel compounds prepared by the process. Although the invention will be described and referred to as it relates to processes of preparation of anomers from specific donors, acceptors, promoters, and solvents, and the resulting anomers, it will be understood that the principles of this invention are equally applicable to similar processes and anomers and accordingly, it will be understood that the invention is not limited to such processes and anomers.

BACKGROUND AND PRIOR ART

The literature teaches the use of various glycosyl donors (sugar residues with a leaving group) with anomeric bromide and other functional groups to build an ultimate di-, tri-, or oligosaccharide.

O-protected beta bromo anomer is converted to the alpha disaccharide in 42% and 65% yield (Lemieux, J. Am. Chem. Soc. 1975, 97, 4056).

Similarly the alpha bromo 1,2-trans peracetyl glycoside anomer is converted to the equivalent beta (1,2-trans) glycoside in 47%, 64%, and 72% yield while the beta acetyl anomer was similarly converted in 71%, 72% and 80% yield (Hanessian, Carbohdr. Res., 53, C13 (1977) and 59, 261 (1977).

Activation of various anomeric donors has been heavily studied, using a variety of promoters. Particularly of interest are those where the alpha:beta product ratio is known and can be improved, and where the overall yield is high.

Previous work from applicant's laboratories has shown that glycosides can be prepared from glycosyl heterocyclic donors without protection of OH groups (S. Hanessian et al. Carbohydrate Res. 80, C17 (1980)). Speculation as to reaction mechanisms suggests metal complex formation with beta 2-pyridylthio donor leaving group, that is the activation is remote to the anomeric carbon, which applicant has termed "remote activation."

Extension of experimentation to a beta perbenzylated glycosyl 2-pyridinecarboxylate donor showed solvent dependence of anomeric product—ether-$CH_2Cl_2$ giving primarily alpha while $CH_3CN$ gave primarily beta. Other extension based on applicant's original work can be found in Tetrahedron, 47, 6435, (1991).

It is a broad object of the invention to prepare specific anomeric compounds in improved yield and proportion, by selection of specific donors, selection of specific acceptors, selection of specific solvents, and selection of specific promoters, in combination underselected specific process conditions. It is an ancillary object of the invention to identify specific donors, suitable for use in the invention. It is another ancillary object of the invention to identify specific acceptors, suitable for use in the invention. It is another ancillary object of the invention to identify specific promoters, suitable for use in the invention. It is another ancillary object of the invention to identify specific solvents, suitable for use in the invention. It is a subsidiary object of the invention to prepare novel anomeric compounds, utilizing unprotected and O-protected glycosyl donors. It is a further subsidiary object of the invention to develop synthetic methods for the synthesis of glycosides, disaccharides, oligosaccharides and nucleosides, using glycosides including but not restricted to pyridyloxy, methoxypyridyloxy, pyrimidyloxy, pyridylcarbonate, and pyridylthiocarbonate leaving groups, to provide said glycosides, disaccharides, oligosaccharides and nucleosides, including polymer supported oligosaccharide syntheses, in superior yield and stereospecificity, faster reaction times and shorter syntheses.

In another embodiment of the invention a still further object is to provide for a solid phase process to prepare oligosaccharides using the MOP glycosides in which process a resin support is employed. This objective employs a process in which a fixed glycocide is then permitted to react with an acetylated MOP glycocide.

GENERAL SCOPE OF INVENTION

The overall synthetic scope, of the invention is generally indicated, without such indication being restrictive or limiting in scope or application, Table XLIV.

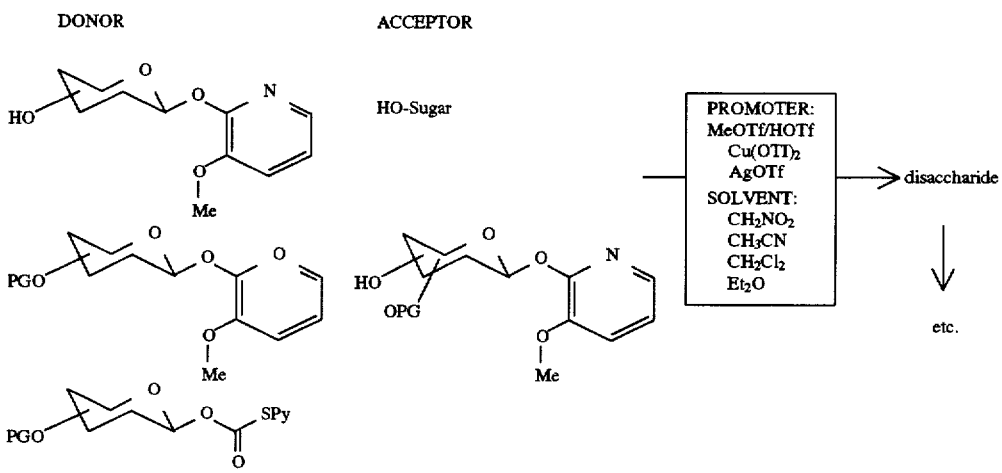

In one broad aspect the invention is directed to a process of glycoside synthesis comprising reaction of a donor selected from O-pyranosyl and O-furanosyl glycosides, with an acceptor including an alcoholic hydroxyl, in the presence of a promoter and a solvent, the improvement providing that the donor is selected from the group consisting of glycosides substituted by leaving groups D of formula XII and related heterocyclic bases.

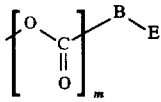

FORMULA XII where m is 0 or 1, when m is 0, B is O, when m is 1, B is O or S, and E has formula XIII.

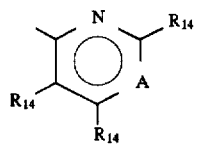

FORMULA XIII when A is N, or CR14, R14 is H or alkoxy of 1 to 5 carbon atoms, or two adjacent R14 together form a four carbon portion of a fused benzenoid ring. The promoter is selected from the group consisting of MeOTf, TfOH, BF₃, AgOTf, Cu(OTf)₂, ZnCl₂, and other acids, Lewis acids and chelating metals. The solvent is selected from the group consisting of CH₃NO₂, and CH₂Cl₂, Et₂O, CH₃CN, DMF, THF, and other solvents of like polarity and dipole moment and mixtures thereof.

In a second broad aspect the invention is directed to an improved process of glycoside synthesis comprising reaction of a donor selected from O-pyranosyl and O-furanosyl glycosides, with an acceptor including an alcoholic hydroxyl, in the presence of a promoter and a solvent. The improvement provides a donor selected from the group consisting of glycosides substituted by leaving groups X of formula I and related heterocyclic bases:

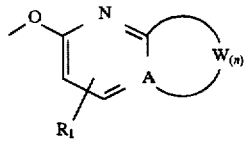

FORMULA I where n is 0 or 1, and W is a heterocyclic or biheterocyclic ring with each ring having from 5 to 7 atoms of which up to 2 atoms can be S, O or N, or a combination thereof. A is N, or CH, and R1 is H, alkoxy-alkyl in which the alkoxy and alkyl group contain up to 5 carbon atoms each, or alkoxy of 1 to 5 carbon atoms, said promoter is selected from the group consisting of MeOTf, TfOH, BF₃, Cu(OTf)₂, ZnCl₂, and other acids, Lewis acids, and N-haloimides, and chelating metals. The promoter is selected from the group consisting of MeOTf, TfOH, BF₃, Cu(OTf)₂, ZnCl₂, and other acids, Lewis acids and chelating metals. The solvent is selected from the group consisting of CH₃NO₂, and CH₂Cl₂, Et₂O, CH₃CN, DMF, THF, and other solvents of like polarity and dipole moment and mixtures thereof.

Preferably the donor is an O-pyranosyl glycoside, the promoter is selected from the group consisting of MeOTf, TfOH, BF₃, Cu(OTf)₂, and ZnCl₂, and the solvent is selected from the group consisting of CH₃NO₂, and CH₂Cl₂, Et₂O, CH₃CN, DMF and THF, and mixtures thereof.

More preferably the donor is selected from the group consisting of glycosides of formula RX wherein X has formula I and related heterocyclic structures, and R has formula II.

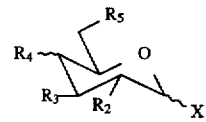

FORMULA II wherein R2 is azido, acyloxy of 2 to 6 carbon atoms, acylamino of 2 to 5 carbon atoms, hydroxy, arylcarboxy of 7 to 10 carbon atoms unsubstituted or halogen substituted, arylalkoxy of 7 to 10 carbon atoms, or alkoxy of 1 to 10 carbon atoms, R3, and R4 are independently hydroxy, acyloxy of 2 to 6 carbon atoms, arylcarboxy of 7 to 10 carbon atoms unsubstituted or halogen substituted, arylalkoxy of 7 to 10 carbon atoms, or alkoxy of 1 to 10 carbon atoms, R5 is independently hydroxy, acyloxy of 2 to 6 carbon atoms, arylcarboxy of 7 to 10 carbon atoms unsubstituted or halogen substituted, arylalkoxy of 7 to 10 carbon atoms, alkoxy of 1 to 10 carbon atoms, trialkylsiloxy wherein the alkyls are independently of 1 to 5 carbon atoms, or R2, R3, R4, R5, may be R. The promoter is selected from the group consisting of MeOTf, TMSOTf, TfOH, BF₃, Cu(OTf)₂, and ZnCl₂, while the solvent is selected from the group consisting of CH₃NO₂, CH₂Cl₂, Et₂O, CH₃CN, DMF, and THF and mixtures thereof.

Conveniently the the acceptor is selected from the group consisting of R'OH, wherein R' is alkyl, alkenyl, cycloalkyl, cycloalkenyl, or aralkyl of 1 to 27 carbon atoms, including N-substituted amino-alcohols and S-substituted thio-alcohols, esters of alkanols of 1 to 10 carbon atoms with hydroxyalkanoic acids of 2 to 6 carbon atoms, esters of alkanols of 1 to 10 carbon atoms with hydroxyaminoalkanoic acids of 2 to 6 carbon atoms having the amino function acylated by an acid of 2 to 10 carbon atoms, and glycosides of formula R"Y, wherein R" has formula III.

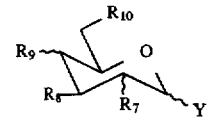

FORMULA III containing at least one unprotected alcoholic hydroxyl, where Y is selected from the group consisting of alkoxy of 1 to 12 carbon atoms and X, R7 is azido, hydroxyl, acyloxy of 2 to 6 carbon atoms, arylcarboxy of 7 to 10 carbon atoms unsubstituted or halogen substituted, arylalkoxy of 7 to 10 carbon atoms, alkoxy of 1 to 10 carbon atoms, hydrogen, or aminocarbalkoxy of 2 to 10 carbon atoms, R8 is hydrogen, hydroxyl, alkenyloxy of 1 to 5 carbon atoms, acyloxy of 2 to 6 carbon atoms, arylcarboxy of 7 to 10 carbon atoms unsubstituted or halogen substituted, arylalkoxy of 7 to 10 carbon atoms, or alkoxy of 1 to 10 carbon atoms, R9 is hydroxyl, arylcarboxy of 7 to lo carbon atoms unsubstituted or halogen substituted, arylalkoxy of 7 to 10 carbon atoms, alkoxy of 1 to 10 carbon atoms, or acyloxy of 2 to 6 carbon atoms, R10 is hydroxyl arylalkoxy of 7 to 10 carbon atoms, or alkoxy of 1 to 10 carbon atoms, Y and R7 may together be alkylidenyldioxy of 3 to 9 carbon atoms, or cycloalkylidenyldioxy of 5 to 10 carbon atoms, or R8 and R9 may together be alkylidenyldioxy of 3 to 9 carbon atoms, or cycloalkylidenyldioxy of 5 to 10 carbon atoms or R9 and R10 arylalkylidenyldioxy of 7 to 10 carbon atoms or R7, R8, R9, R10 may be R or R".

Most preferably X is 3-methoxy-pyridyl-2-oxy. The process may be considered as two distinct groups depending on whether the X group is alpha or beta on the pyranosyl ring. In the beta case R has formula IV, while in the alpha case R has the formula V.

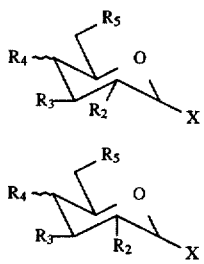

FORMULA IV (BETA)

FORMULA V (ALPHA)

In the alpha case, R2, is azido, arylalkoxy of 7 to 10 carbon atoms, or alkoxy of 1 to 10 carbon atoms, R3, R4 and R5 are arylalkoxy of 7 to 10 carbon atoms, or alkoxy of 1 to 10 carbon atoms. The promoter is $Cu(OTf)_2$. The solvent is selected from the group consisting of $CH_2Cl_2$, $Et_2O$, and mixtures thereof. The acceptor is selected from the group consisting of glycosides of formula R"Y, containing at least one unprotected alcoholic hydroxyl, wherein Y is alkoxy of 1 to 12 carbon atoms, R7 is hydroxy, acyloxy of 2 to 6 carbon atoms, arylalkoxy of 7 to 10 carbon atoms, alkoxy of 1 to 10 carbon atoms, or aminocarbalkoxy of 2 to 10 carbon atoms, R8 is hydrogen, hydroxyl, acyloxy of 2 to 6 carbon atoms arylalkoxy of 7 to 10 carbon atoms, or alkoxy of 1 to 10 carbon atoms, R9 is hydroxyl, or acyloxy of 2 to 6 carbon atoms, R10 is hydroxyl arylalkoxy of 7 to 10 carbon atoms, or alkoxy of 1 to 10 carbon atoms, R9 and R10 may together be aralkylidenyldioxy of 7 to 10 carbon atoms.

In another aspect the process may be applied to unprotected donors wherein R2, R3, and R4 are independently hydroxy, arylalkoxy of 7 to 10 carbon atoms, or alkoxy of 1 to 10 carbon atoms, R5 is independently hydroxy, arylalkoxy of 7 to 10 carbon atoms, alkoxy of 1 to 10 carbon atoms or trialkylsiloxy wherein the alkyls are independently of 1 to 5 carbon atoms, or R2, R3, R4, R5 may be R, and at least one of R2, R3, R4 and R5 is hydroxyl. The promoter is selected from the group consisting of MeOTf, TMSOTf, $BF_3$, $Cu(OTf)_2$, and $ZnCl_2$. The solvent is selected from the group consisting of $CH_3NO_2$, $CH_2Cl_2$, $CH_3CN$, and THF and mixtures thereof. The acceptor may be selected from the group consisting of alkanols, alkenols and cycloalkanols of 1 to 6 carbon atoms and glycosides of formula R"Y, containing at least one unprotected alcoholic hydroxyl, wherein Y and R7 together are alkylidenyldioxy of 3 to 9 carbon atoms, R8 and R9 together are alkylidenyldioxy of 3 to 9 carbon atoms. More preferably wherein R2, R3, R4 and R5 are hydroxyl, that it is the donor is unprotected.

In a further aspect protecting groups may be provided by ethers, in which case R2, R3, R4 and R5 are arylalkoxy of 7 to 10 carbon atoms, or alkoxy of 1 to 10 carbon atoms. The promoter is selected from the group consisting of MeOTf, and Cu(OTf)2. The solvent is selected from the group consisting of $CH_3NO_2$, $CH_2Cl_2$, $Et_2O$, and $CH_3CN$ and mixtures thereof. Preferably the acceptor is selected from the group consisting of alkanols of 1 to 5 carbon atoms and glycosides of formula R"Y, containing at least one unprotected alcoholic hydroxyl, wherein Y is selected from the group consisting of alkoxy of 1 to 12, and preferably 1 to 5 carbon atoms and 3-methoxy-pyridyl-2-oxy, R7 is azido, hydroxyl, acyloxy of 2 to 6 carbon atoms, arylcarboxy of 7 to 10 carbon atoms unsubstituted or halogen substituted, arylalkoxy of 7 to 10 carbon atoms, alkoxy of 1 to 10 carbon atoms, hydrogen, or aminocarbalkoxy of 2 to 10 carbon atoms, R8 is hydroxyl, acyloxy of 2 to 6 carbon atoms, arylcarboxy of 7 to 10 carbon atoms unsubstituted or halogen substituted, arylalkoxy of 7 to 10 carbon atoms, or alkoxy of 1 to 10 carbon atoms, R9 is hydroxyl, arylcarboxy of 7 to 10 carbon atoms unsubstituted or halogen substituted, or acyloxy of 2 to 6 carbon atoms, R10 is hydroxyl arylalkoxy of 7 to 10 carbon atoms, or alkoxy of 1 to 10 carbon atoms, Y and R7 may together be alkylidenyldioxy of 3 to 9 carbon atoms, or R8 and R9 may together be alkylidenyldioxy of 3 to 9 carbon atoms, or R9 and R10 may together be aralkylidenyldioxy of 7 to 10 carbon atoms.

In a further aspect the protecting groups may be esters, here R2, R3, and R4 are independently acyloxy of 2 to 6 carbon atoms, or arylcarboxy of 7 to 10 carbon atoms unsubstituted or halogen substituted, R5 is independently acyloxy of 2 to 6 carbon atoms, arylcarboxy of 7 to 10 carbon atoms unsubstituted or halogen substituted, and trialkylsiloxy wherein the alkyls are independently of 1 to 5 carbon atoms, or R. The promoter is $Cu(OTf)_2$, and the solvent is $CH_2Cl_2$. In this case the acceptor is preferably a glycoside of formula R"Y, containing at least one unprotected alcoholic hydroxyl, wherein Y is alkoxy of 1 to 12, preferably 1 to 5 carbon atoms, R7 is arylalkoxy of 7 to 10 carbon atoms, alkoxy of 1 to 10 carbon atoms, or aminocarbalkoxy of 2 to 10 carbon atoms, R8 is alkenyloxy of 1 to 5 carbon atoms, arylalkoxy of 7 to 10 carbon atoms, or alkoxy of 1 to 10 carbon atoms, R9 is hydroxyl, arylalkoxy of 7 to 10 carbon atoms, or alkoxy of 1 to 10 carbon atoms, R10 is hydroxyl, arylalkoxy of 7 to 10 carbon atoms, or alkoxy of 1 to 10 carbon atoms.

In a further aspect when an aminosugar or precursor is being prepared when the precursor function is acylamino, then R2 is acylamino of 2 to 5 carbon atoms, R3, R4 and R5 are hydroxyl. The promoter is selected from the group consisting of MeOTf, and TfOH. The solvent is selected from the group consisting of $CH_3NO_2$ and DMF and mixtures thereof. Preferably the acceptor is selected from the group consisting of alkanols of 1 to 5 carbon atoms and glycosides of formula R"Y, containing at least one unprotected alcoholic hydroxyl, wherein Y is 3-methoxy-pyridyl-2-oxy, R7 is azido, R8 is acyloxy of 2 to 6 carbon atoms, R9 is acyloxy of 2 to 6 carbon atoms, R10 is hydroxyl, Y and R7 may together be alkylidenyldioxy of 3 to 9 carbon atoms, or R8 and R9 may together be alkylidenyldioxy of 3 to 9 carbon atoms.

In a further aspect when an aminosugar or precursor is being prepared when the precursor function is azido, then R2 is azido, R3, is arylalkoxy of 7 to 10 carbon atoms, alkoxy of 1 to 10 carbon atoms or R wherein R2, R3, R4, and R5 are acyloxy of 2 to 6 carbon atoms, R4 and R5, are arylalkoxy of 7 to 10 carbon atoms, or alkoxy of 1 to 10 carbon atoms, or R4 and R5 together are alkylidenyldioxy of 3 to 9 carbon atoms. The promoter is Cu(OTf)2, while the solvent is selected from the group consisting of $CH_2Cl_2$, and $CH_3CN$ and mixtures thereof. Preferably the acceptor is selected from the group consisting of esters of alkanols of 1 to 10 carbon atoms with hydroxyaminoalkanoic acids of 2 to 6 carbon atoms having the amino function acylated by an acid of 2 to 10 carbon atoms, and glycosides of formula R"Y, containing at least one unprotected alcoholic hydroxyl, wherein Y is alkoxy of 1 to 12 carbon atoms, R7 is acyloxy of 2 to 6 carbon atoms, arylalkoxy of 7 to 10 carbon atoms, alkoxy of 1 to 10 carbon atoms, hydroxyl, or aminocarbalkoxy of 2 to 10 carbon atoms, R8 is hydrogen, acyloxy of 2 to 6 carbon atoms, arylalkoxy of 7 to 10 carbon atoms, alkoxy of 1 to 10 carbon atoms, or hydroxyl, R9 is hydroxyl, arylcarboxy of 7 to 10 carbon atoms unsubstituted or halogen substituted, arylalkoxy of 7 to 10 carbon atoms, alkoxy of 1 to 10 carbon atoms, or acyloxy of 2 to 6 carbon atoms, R10 is hydroxyl or acyloxy of 2 to 6 carbon atoms, or R9 and R10 aralkylidenyldioxy of 7 to 10 carbon atoms.

The invention additionally encompasses an improved a process of nucleoside synthesis comprising reaction of a donor selected from O-pyranosyl and O-furanosyl glycosides, with an acceptor including a trialkylsilyl ether of a pyrimidine, in the presence of a promoter and a solvent. The improvement lies in selecting the donor from the group consisting of glycosides substituted by leaving groups X of formula I and related heterocyclic bases:

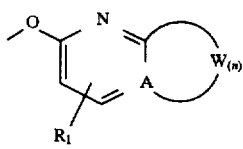

FORMULA I where n is 0 or 1, and W is a heterocyclic or biheterocyclic ring with each ring having from 5 to 7 atoms of which up to 2 atoms can be S, O or N, or a combination thereof. A is N, or CH, and R1 is H, alkoxy-alkyl in which the alkoxy and alkyl group contain up to 5 carbon atoms each, or alkoxy of 1 to 5 carbon atoms. The promoter is TMSOTf, and other acids, Lewis acids and chelating metals. The solvent is selected from the group consisting of toluene, benzene, dioxane, $CH_2Cl_2$, $Et_2O$, THF, and other solvents of like polarity and dipole moment and mixtures thereof. Preferably the donor is an O-pyranosyl or O-furanosyl glycoside, of formulae II or VI, and the trialkyl silyl pyrimidine ether has formula VII (or a corresponding 5 or 6 position analog having an N thereat).

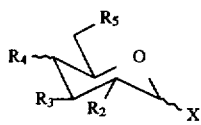

FORMULA II

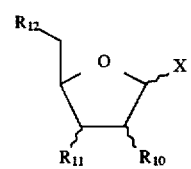

FORMULA VI

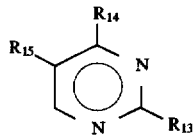

FORMULA VII wherein R2, R3, R4, and R5 are arylalkoxy of 7 to 10 carbon atoms, or alkoxy of 1 to 10 carbon atoms, R10, is hydrogen or arylalkoxy of 7 to 10 carbon atoms, or alkoxy of 1 to 10 carbon atoms, R11 and R12 are arylalkoxy of 7 to 10 carbon atoms, or alkoxy of 1 to 10 carbon atoms, R13 is trialkyl-siloxy wherein the alkyls are independently of 1 to 5 carbon atoms, R14 is trialkylsiloxy wherein the alkyls are independently of 1 to 5 carbon atoms, or acylamino of 7 to 10 carbon atoms, R15 is hydrogen, or alkyl of 1 to 5 carbon atoms. Most preferably R2, R3, R4, R5, R11, R12 are benzyloxy, R11 is hydrogen or benzyloxy, R13 is trimethylsiloxy, R14 is trimethylsiloxy or benzamido, R15 is hydrogen or methyl.

The invention is further directed to an improved process of glycoside synthesis comprising reaction of a donor selected from O-pyranosyl and O-furanosyl glycosides, with an acceptor including an alcoholic hydroxyl, in the presence of a promoter and a solvent. The improvement lies in selecting the donor from the group consisting of glycosides substituted by leaving groups X of formula I and related heterocyclic bases:

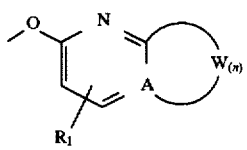

FORMULA I where n is 0 or 1, and W is a heterocyclic or biheterocyclic ring with each ring having from 5 to 7 atoms of which up to 2 atoms can be S, O or N, or a combination thereof A is N, or CH, and R1 is H, alkoxy-alkyl in which the alkoxy and alkyl group contain up to 5 carbon atoms each, or alkoxy of 1 to 5 carbon atoms. The promoter is selected from the group consisting of MeOTf, TfOH, $BF_3$, $Cu(OTf)_2$, $ZnCl_2$, and other acids, Lewis acids and chelating metals. The solvent is selected from the group consisting of $CH_3NO_2$, and $CH_2Cl_2$, $Et_2O$, $CH_3CN$, DMF, THF, and other solvents of like polarity and dipole moment and mixtures thereof. The glycoside is coupled to a supporting resin by a coupling group integral to the resin, and a linking element bonded to coupling group and the glycoside. Preferably the coupling group is phenylenemethylamine, the linking element is a dicarboxylic acid residue forming an amido bond with the coupling group and an ester bond with the glycoside. More preferably the glycoside comprises a plurality of saccharide units.

In a further aspect the invention is directed to an improved process of glycoside synthesis comprising reaction of a donor selected from O-pyranosyl and O-furanosyl glycosides, with an acceptor including an alcoholic hydroxyl, in the presence of a promoter and a solvent. The improvement comprising selecting the donor from the group consisting of glycosides substituted by leaving groups of formula VIII:

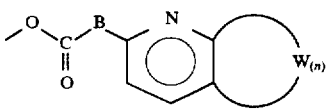

FORMULA VIII where n is 0 or 1, and W is a heterocyclic or biheterocyclic ring with each ring having from 5 to 7 atoms of which up to 2 atoms can be S, O or N, or a combination thereof and where B is O or S. The promoter is selected from the group consisting of MeOTf, TfOH, $BF_3$, AgOTf, $Cu(OTf)_2$, $ZnCl_2$, and other acids, Lewis acids and chelating metals. The solvent is selected from the group consisting of $CH_3NO_2$, and $CH_2Cl_2$, $Et_2O$, $CH_3CN$, DMF, THF, and other solvents of like polarity and dipole moment and mixtures thereof. When the donor is an O-pyranosyl glycoside, the promoter is selected from the group consisting of AgOTf and Cu $(OTf)_2$, the solvent is selected from the group consisting of $CH_3NO_2$, and $CH_2Cl_2$, $Et_2O$, $CH_3CN$, DMF and THF, and mixtures thereof. When the donor is selected from the group consisting of glycosides of formula IX wherein Z has formula VIII,

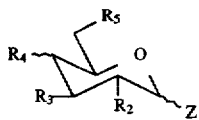

FORMULA IX then R2 is acyloxy of 2 to 6 carbon atoms, arylcarboxy of 7 to 10 carbon atoms unsubstituted or halogen substituted, arylalkoxy of 7 to 10 carbon atoms, or alkoxy of 1 to 10 carbon atoms, R3, and R4 are independently acyloxy of 2 to 6 carbon atoms, arylcarboxy of 7 to 10 carbon atoms unsubstituted or halogen substituted, arylalkoxy of 7 to 10 carbon atoms, or alkoxy of 1 to 10 carbon atoms, R5 is independently acyloxy of 2 to 6 carbon atoms, arylcarboxy of 7 to 10 carbon atoms unsubstituted or halogen substituted, arylalkoxy of 7 to 10 carbon atoms, alkoxy of 1 to 10 carbon atoms, trialkylsiloxy wherein the alkyls are independently of 1 to 5 carbon atoms, or R2, R3, R4, R5, may be R. The promoter is selected from the group consisting of AgOTf, and $Cu(OTf)_2$. The solvent is selected from the group consisting of $CH_3NO_2$, $CH_2Cl_2$, $Et_2O$, $CH_3CN$, DMF, and THF and mixtures thereof.

When the donor is selected from the group consisting of glycosides of formula X wherein Z has formula VIII,

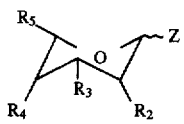

FORMULA X then R2, R3 and R4 are independently acyloxy of 2 to 6 carbon atoms, or arylcarboxy of 7 to 10 carbon atoms unsubstituted or halogen substituted, R5 is alkyl of 1 to 5 carbon atoms. Then the promoter is selected from the group consisting of AgOTf, and Cu(OTf)$_2$, the solvent is selected from the group consisting of $CH_3NO_2$, $CH_2Cl_2$, $Et_2O$, $CH_3CN$, DMF, and THF and mixtures thereof.

When the acceptor is selected from the group consisting of glycosides of formula RX wherein X has formula I and related heterocyclic structure, and R has the formula II

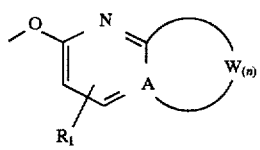

FORMULA I

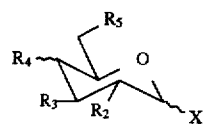

FORMULA II where n is 0 or 1, and W is a heterocyclic or biheterocyclic ring with each ring having from 5 to 7 atoms of which up to 2 atoms can be S, O or N, or a combination thereof A is N, or CH, and R1 is H, alkoxy-alkyl in which the alkoxy and alkyl group contain up to 5 carbon atoms each, or alkoxy of 1 to 5 carbon atoms, R2 is azido, acyloxy of 2 to 6 carbon atoms, arylcarboxy of 7 to 10 carbon atoms unsubstituted or halogen substituted, arylalkoxy of 7 to 10 carbon atoms, or alkoxy of 1 to 10 carbon atoms, R3, and R4 are independently ydroxy, acyloxy of 2 to 6 carbon atoms, arylcarboxy of-7 to 10 carbon atoms unsubstituted or halogen substituted, arylalkoxy of 7 to 10 carbon atoms, or alkoxy of 1 to 10 carbon atoms, R5 is independently hydroxy.

In a further development the invention is directed to an improved process of nucleoside synthesis comprising reaction of a donor selected from O-pyranosyl and O-furanosyl glycosides, with an acceptor including a trialkylsilyl pyrimidine ether, or a corresponding 5 or 6 position analog having an N thereat, in the presence of a promoter and a solvent, the improvement lies in selecting the donor from the group consisting of glycosides substituted by leaving groups of formula VIII:

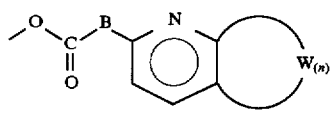

FORMULA VIII where B is O or S, n is 0 or 1, and W is a heterocyclic or biheterocyclic ring with each ring having from 5 to 7 atoms of which up to 2 atoms can be S, O or N, or a combination thereof. The promoter is selected from the group consisting of TMSOTf, MeOTf, TfOH, $BF_3$, AgOTf, Cu(OTf)$_2$, $ZnCl_2$, and other acids, Lewis acids and chelating metals. The solvent is selected from the group consisting of toluene, THF, and other solvents of like polarity and dipole moment and mixtures thereof. When the donor is an O-pyranosyl or O-furanosyl glycoside, of formulae IX, X, or XI, and the trialkyl silyl pyrimidine ether (or a corresponding 5 or 6 position analog having an N thereat) has formula VII

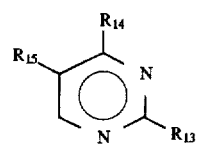

FORMULA VII

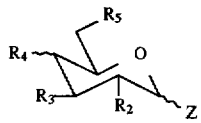

FORMULA IX

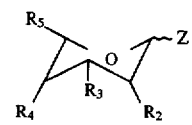

FORMULA X

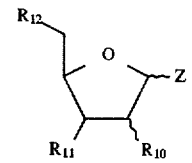

FORMULA XI wherein R2, R3, R4, and R5 are arylalkoxy of 7 to 10 carbon atoms, or alkoxy of 1 to 10 carbon atoms, R10, is hydrogen or arylalkoxy of 7 to 10 carbon atoms, or alkoxy of 1 to 10 carbon atoms, R11 and R12 are arylalkoxy of 7 to 10 carbon atoms, or alkoxy of 1 to 10 carbon atoms, R13 is trialkyl-siloxy wherein the alkyls are independently of 1 to 5 carbon atoms, R14 is trialkylsiloxy wherein the alkyls are independently of 1 to 5 carbon atoms, or acylamino of 7 to 10 carbon atoms, R15 is hydrogen, or alkyl of 1 to 5 carbon atoms, and Z has formula VIII.

In a further development the invention is directed to an improved process of nucleoside synthesis comprising reaction of a donor selected from O-pyranosyl and O-furanosyl glycosides, with an acceptor including an acylated purine in the presence of bromine or a like oxidiser, and a solvent, the improvement comprising the donor is selected from the group consisting of glycosides substituted by leaving groups of formula VIII:

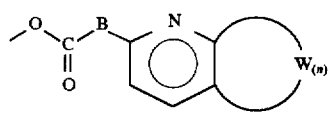

FORMULA VIII where B is O or S and where n is 0 or 1, and W is a heterocyclic or biheterocyclic ring with each ring having from 5 to 7 atoms of which up to 2 atoms can be S, O or N, or a combination thereof. The solvent is-selected from the group consisting of DMF and other solvents of like polarity and dipole moment and mixtures thereof. Preferably the purine is 6-benzoyl adenine.

Having just generally described the invention, reference will be made to the accompanying examples describing preferred embodiments.

GLYCOSIDE SYNTHESIS WITH UNPROTECTED GLYCOSYL DONORS 2-PYRIDYLOXYGLYCOSYL DONORS AND VARIANTS

Unprotected 2-pyridyloxy beta-D-glycosyl donor was treated with iPrOH (acceptor):$CH_3NO_2$ (solvent) 1:1, at room temperature with Hg(NO$_3$)$_2$, TMSOTf and MeOTf (promoter), Table I, followed by acetylation in pyridine. Hg(NO$_3$)$_2$ gave no reaction, TMSOTf 6:1 alpha:beta, 81%, MeOTf 9:1 alpha:beta, 78%.

TABLE I

[Reaction scheme: triol-pyridyloxy sugar → tetraacetate isopropyl glycoside + β-anomer; conditions: 1. Promoter, rt, CH₃NO₂/iso-PrOH (1:1); 2. Py/Ac₂O]

| Promoter (equiv.) | Time | α:β | Yield(%) |
|---|---|---|---|
| Hg(NO₃)₂ (1.0) | 1 day | No Reaction | |
| TMSOTf (1.0) | 3.5 hrs | 6:1 | 81 |
| MeOTf (1.1) | 45 min | 9:1 | 78 |

Variation of solvent in the same process using MeOTf promoter, Table VIII, CH₃NO₂, CH₂Cl₂, CH₃CN, THF, iPrOH, DMF (as solvent and acceptor) gave good yields (78–85%) and ratios (11:1 to 6:4).

[Reaction scheme: same as above with Solvent/iso-PrOH (1:1)]

| Solvent | MeOTf(equiv.) | Time | α:β | Yield(%) |
|---|---|---|---|---|
| CH₃NO₂ | 1.1 | 45 min | 9:1 | 78 |
| CH₂Cl₂ | 1.0 | 45 min | 5:1 | 79 |
| CH₃CN | 1.0 | 45 min | 4:1 | 84 |
| THF | 1.0 | 45 min | 6:4 | 81 |
| iso-PrOH | 1.0 | 15 min | 11:1 | 85 |
| DMF | 1.0 | 10 min | >10:1 | 87 |

Variation of leaving groups in the same process, demonstrated that 2-pyridyloxy and 6-pyrimidinyloxy gave satisfactory yields and ratios, while phenoxy, thiophenyl, 2-pyridylthio, 2-naphthyridinyloxy, and 2-2-bipyridyl-2-thio were not reactive, under these conditions.

3-METHOXYPYRIDYL-2-OXY (MOP) GLYCOSYL DONORS

Further testing of 3- and 4-methoxypyridyl-2-oxy leaving groups, in the same process, Table II, gave excellent yields (78–88%) and ratios (8 to 9:1 or higher). The time factor was significantly less for the 3-methoxy radical (hereafter MOP) <5 minutes, as opposed to 2.5 hours for the 4-methoxy radical, while the 2-pyridyloxy radical took 45 minutes.

TABLE II

[Reaction scheme: triol-X sugar → tetraacetate isopropyl glycoside + β-anomer; conditions: 1. MeOTf, rt, CH₃NO₂/iso-PrOH (1:1); 2. Py/Ac₂O]

| X | MeOTf(equiv.) | Time | α:β | Yield(%) |
|---|---|---|---|---|
| 2-pyridyloxy | 1.1 | 45 min | 9:1 | 78 |
| 3-OMe-2-pyridyloxy | 1.0 | >5 min | 8:1 | 79 |
| 4-OMe-2-pyridyloxy | 1.0 | 2.5 h | 8:1 | 88 |

The donor results so far can be convincingly partially correlated with basicity (pKa) of the equivalent pyridine, the reactivity time, and the ¹³CNMR (ppm) of the anomeric carbon atom.

Reactivity:

| 3-OMe-MOP | 2-pyridyloxy | 4-OMe-pyridyloxy |
|---|---|---|
| few min. | 45 min. | >2h |
| 97.81 (C-1) | 98.21 (C-1) | 98.71 (C-1) |

¹³CNMR(ppm)

Having established the superiority of the MOP donor, it was tested in the same process against a variety of promoters, Table III. Time considerations militated against $ZnCl_2$, yields against $ZnCl_2$, PTS, ratios against NBS, PTS, ZnCl2, and especially $Cu(OTf)_2$, $BF_3$, and even more so MeOTf gave excellent results.

TABLE III

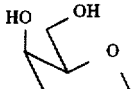

| Promoter (equiv.) | Time | α:β | Yield(%) |
|---|---|---|---|
| MeOTf (1.0) | <5 min | 8:1 | 79 |
| PTS (1.0) | 5 min | 1:1 | 65 |
| BF₃ (1.0) | 5 min | 8:1 | 77 |
| Cu(OTf)₂ (1.0) | 5 min | 7:1 | 82 |
| ZnCl₂ (1.0) | 3 days | 4:1 | 61 |
| NBS (1.0) | <5 min | 6:4 | 78 |

The proportion of MeOTf was varied in the same process, 1.0, 0.2 and 0.016 eq. gave closely similar results 76 to 79% yield ratio 8:1. Only 0.016 eq. gave a longer time 40 min. as opposed to <5 min, which was felt to indicate catalytic rather than reactant nature of the MeOTf promoter.

The process was repeated using beta MOP D-glucopyranoside donor, with methanol, isopropanol, transbut-2-en-1-ol, and cyclohexanol as acceptors, and 0.2 or 0.1 eq. of MeOTf, gave yields (62 to 82%) and ratios (5 to 16:1) Table IV.

TABLE IV

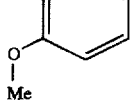

| ROH | MeOTf(equiv.) | Time | α:β | Yield(%) |
|---|---|---|---|---|
| MeOH | 0.2 | >5 min | 10:1 | 82 |
| iso-PrOH | 0.2 | >5 min | 8:1 | 76 |

TABLE IV-continued

| ROH | MeOTf(equiv.) | Time | α:β | Yield(%) |
|---|---|---|---|---|
| Me~~~OH | 0.1 | 10 min | 16:1 | 77 |
| Cyclohexanol | 0.2 | 30 min | 5:1 | 62 |

A similar process was modified using beta MOP 2-azido-2-deoxy-D-galactopyranoside donor, iPrOH acceptor, benzyl glycolate, benzyl N-t-butoxycarbonylserine transbut-2-en-1-ol in heavy equivalent excess gave reaction times of 2 to 4 hours with yields of 65 to 86% and ratios of 6 to 17:1, Table V, which are important as glycosides of 2-amino-2-deoxysugar derivatives.

TABLE V

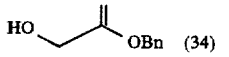

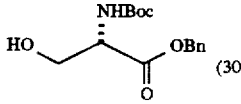

| ROH (equiv.) | Time | α:β | Yield(%) |
|---|---|---|---|
| iso-PrOH/CH₃NO₂(1:1) | 3 hrs | 12:1 | 86 |
| HO~~~C(O)OBn (34) | 2 hrs | 17:1 | 70 |
| HO~~~CH(NHBoc)C(O)OBn (30) | 4 hrs | 8:1 | 65 |
| Me~~~OH (23) | 3 hrs | 6:1 | 84 |

In summary thus far superiority of yield, ratio, time, temperature, and promoter effectiveness has been conclusively demonstrated, with the MOP group. The effective application of the process to donors including unprotected hydroxyl groups has also been shown.

The MOP gluco- and galactopyranoside donors of Tables IV and V were prepared following Schemes I and II, which would be instantly intelligible to those skilled in the art of sugar or organic chemistry.

SCHEME 1
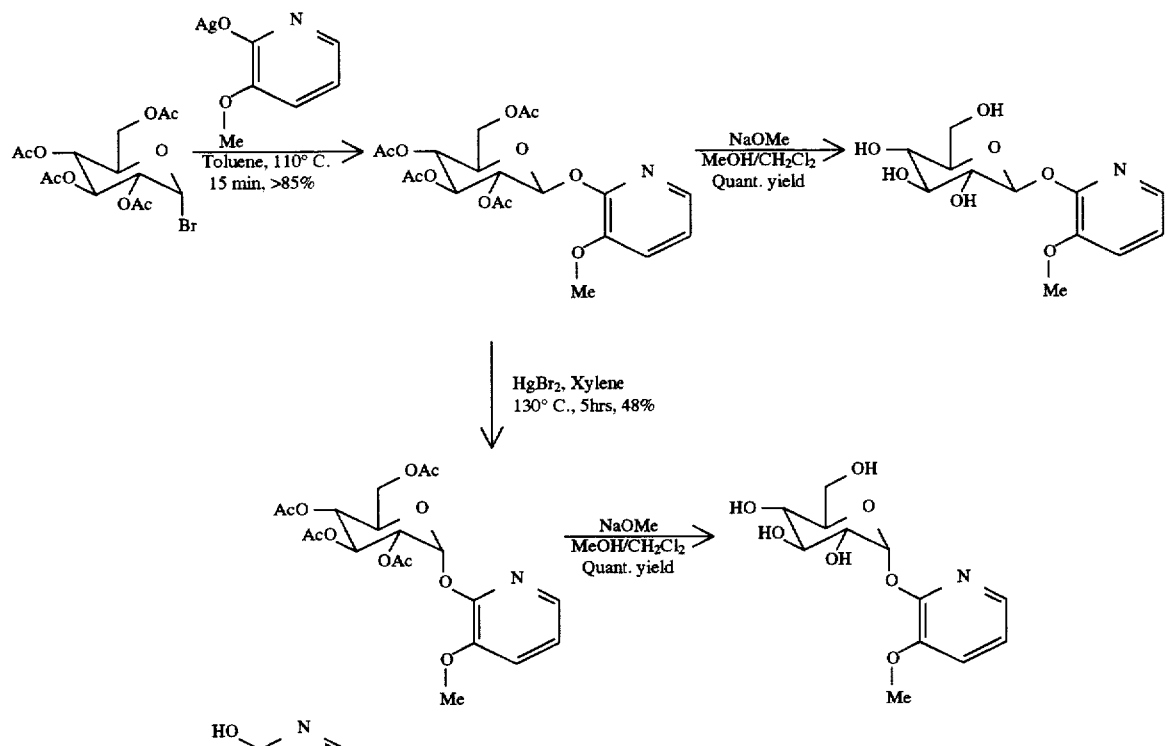
SCHEME II
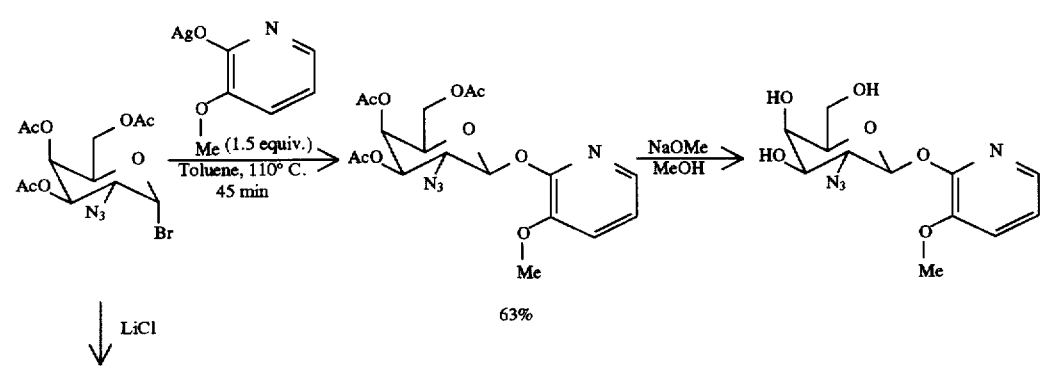

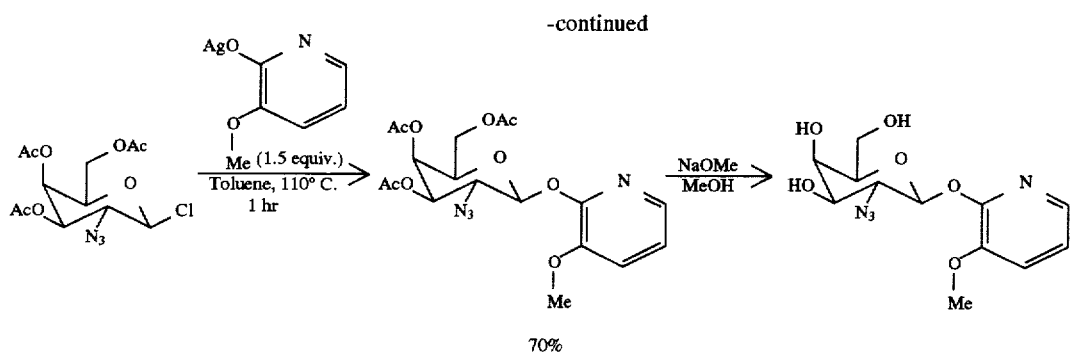

70%

The same process was applied to 2-acetamido-2-deoxy-beta-D-hexopyranoside MOP donors, with 0.1 eq. MeOTf in the gluco case and 0.2 eq. in the galacto case. Pure beta products were obtained in 83 and 88% yield respectively, Table VI.

TABLE VI

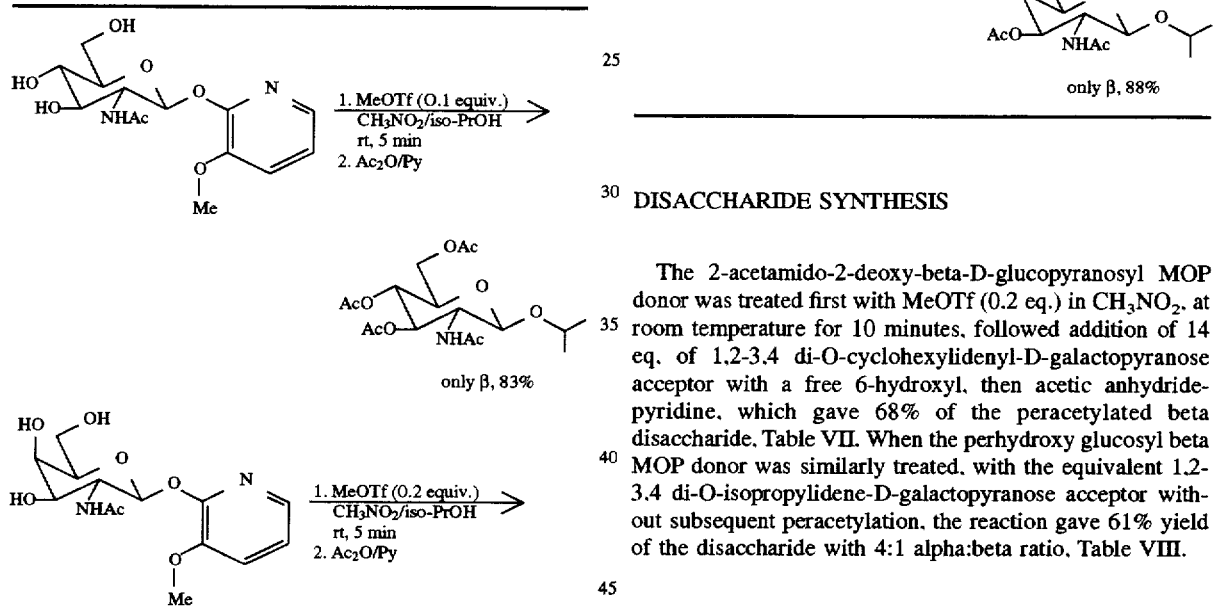

DISACCHARIDE SYNTHESIS

The 2-acetamido-2-deoxy-beta-D-glucopyranosyl MOP donor was treated first with MeOTf (0.2 eq.) in $CH_3NO_2$, at room temperature for 10 minutes, followed addition of 14 eq. of 1,2-3,4 di-O-cyclohexylidenyl-D-galactopyranose acceptor with a free 6-hydroxyl, then acetic anhydride-pyridine, which gave 68% of the peracetylated beta disaccharide, Table VII. When the perhydroxy glucosyl beta MOP donor was similarly treated, with the equivalent 1,2-3,4 di-O-isopropylidene-D-galactopyranose acceptor without subsequent peracetylation, the reaction gave 61% yield of the disaccharide with 4:1 alpha:beta ratio, Table VIII.

TABLE VII

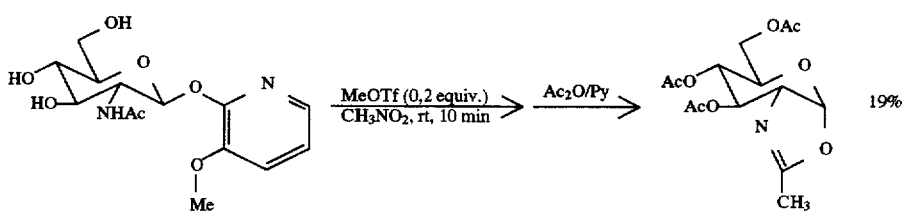

TABLE VII-continued

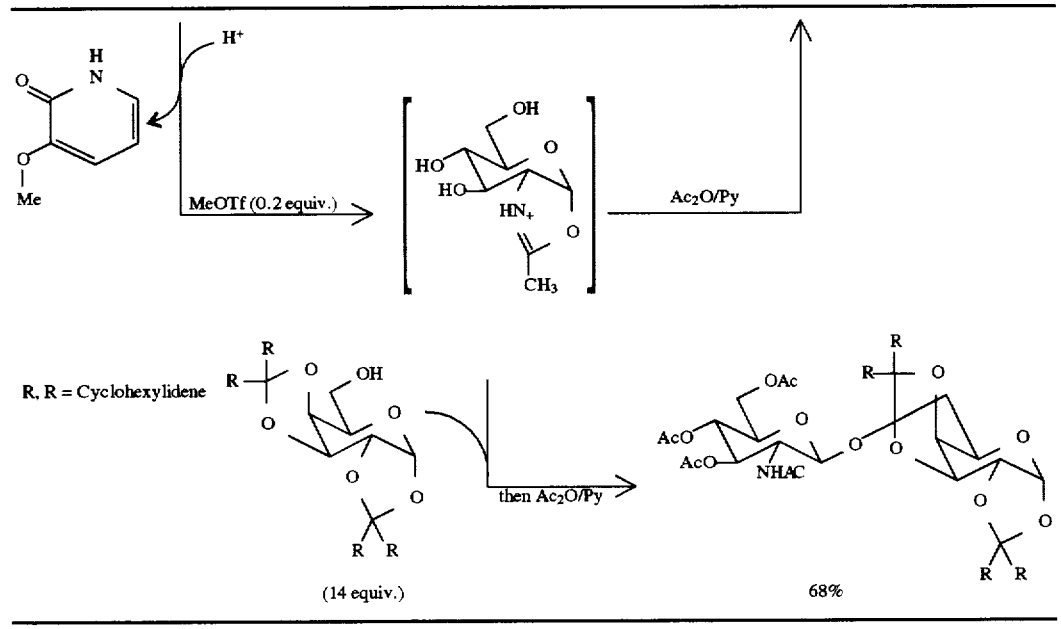

In the absence of the acceptor the oxazoline derivative can be isolated. Table VIII.

TABLE VIII

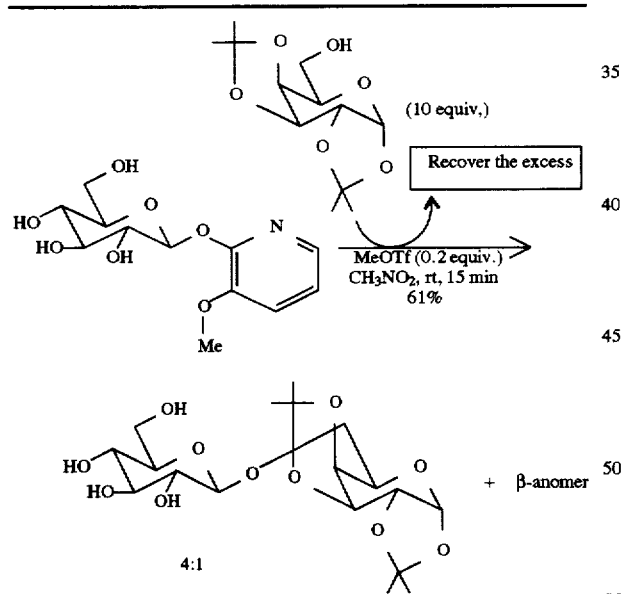

Treating unprotected and peracetylated beta MOP acceptors in the presence of MeOTf (0.2 eq.) in CH₃NO₂/iPrOH for 5 minutes, Table IX, showed the unprotected gluco-, galacto- and 2-azido-2-deoxygalacto donors gave alpha products, while peracetylated donors gave no observable products, and were considered unreactive.

TABLE IX

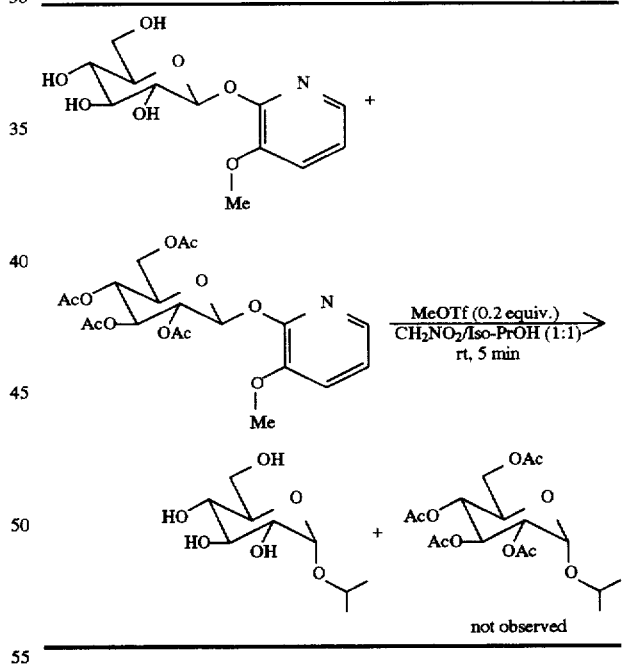

Consideration of the results so far led to three proposed schemes for iterative oligosaccharide synthesis. Scheme III, in which an active donor is coupled with an inactive donor as acceptor to give a disaccharide. The latent donor is then activated either by change of leaving group (1), activation of leaving group (3), or change of substituent (2), and the process repeated with another acceptor. As shown only beta linkages are present, although as those skilled in the art would understand alpha linkages can be generated routinely in such syntheses.

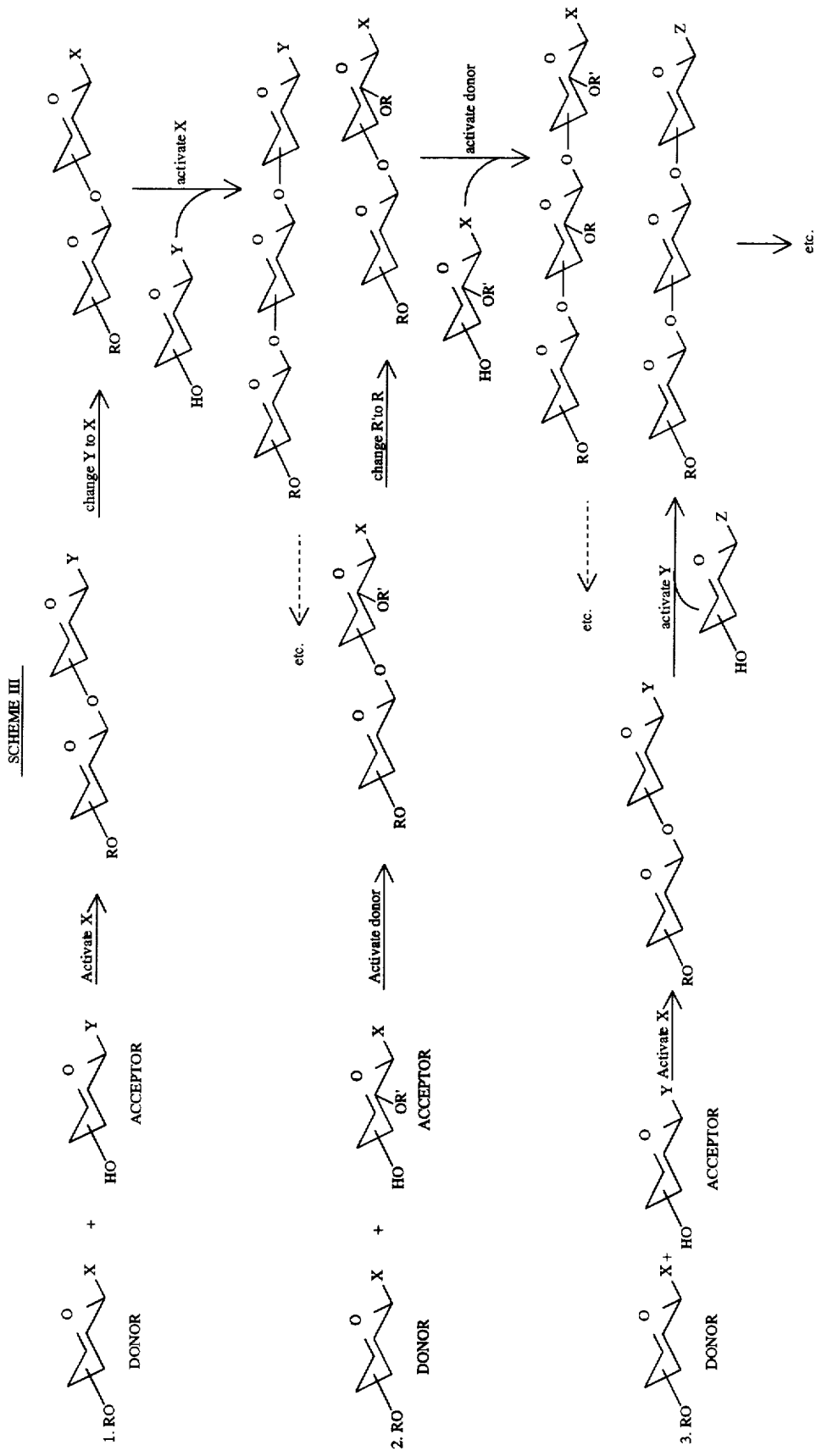

One such synthesis is indicated. Table XI starting using the 2-acetamido-2-deoxy-D-glucopyranosyl MOP donor of Table X, and forming the same beta disaccharide in 70% yield, which is then reduced peracetylated to its diacetamidohomolog, deprotected to form an active donor and coupled with 10 eq. of the same acceptor, in the presence of 2 eq. TfOH in DMF, for 20 minutes at room temperature, then peracetylated to give the beta trisaccharide in 34% yield, which can be further optimized.

TABLE X

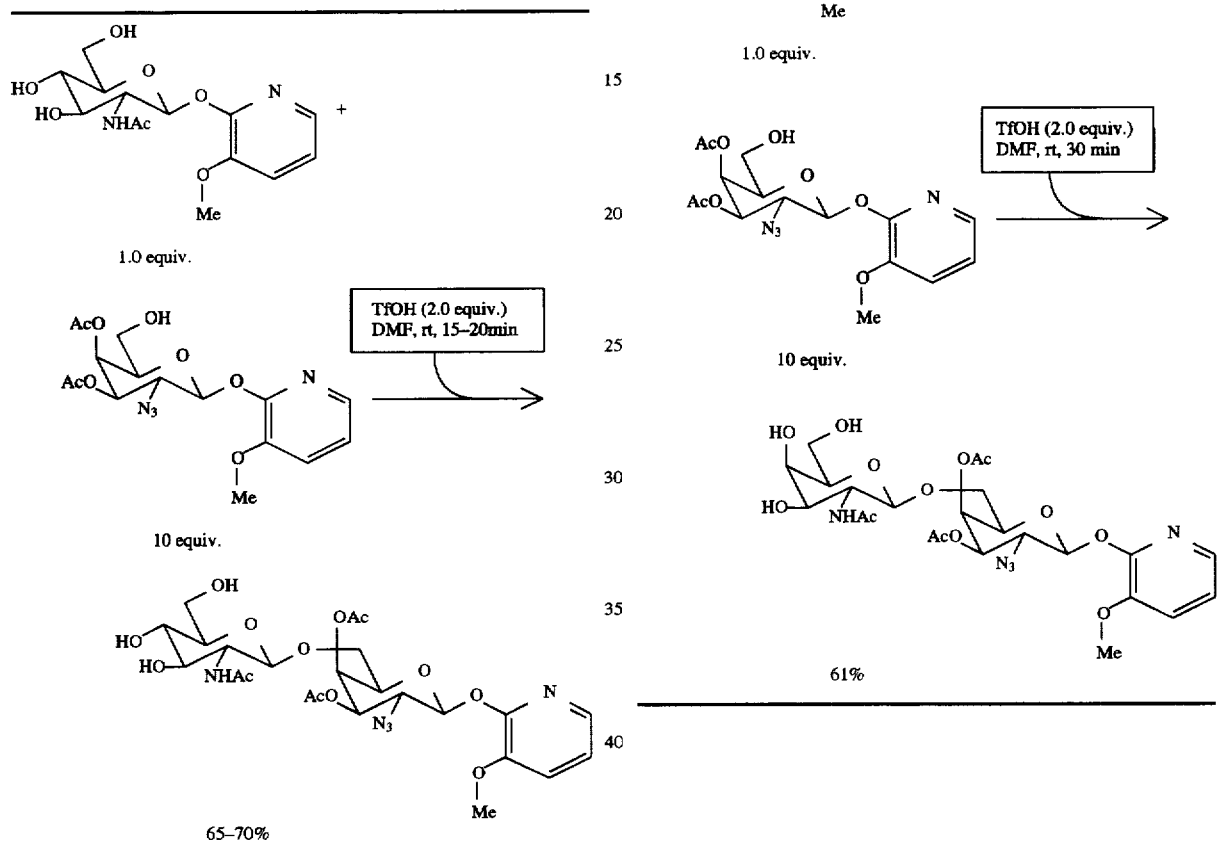

TABLE X-continued

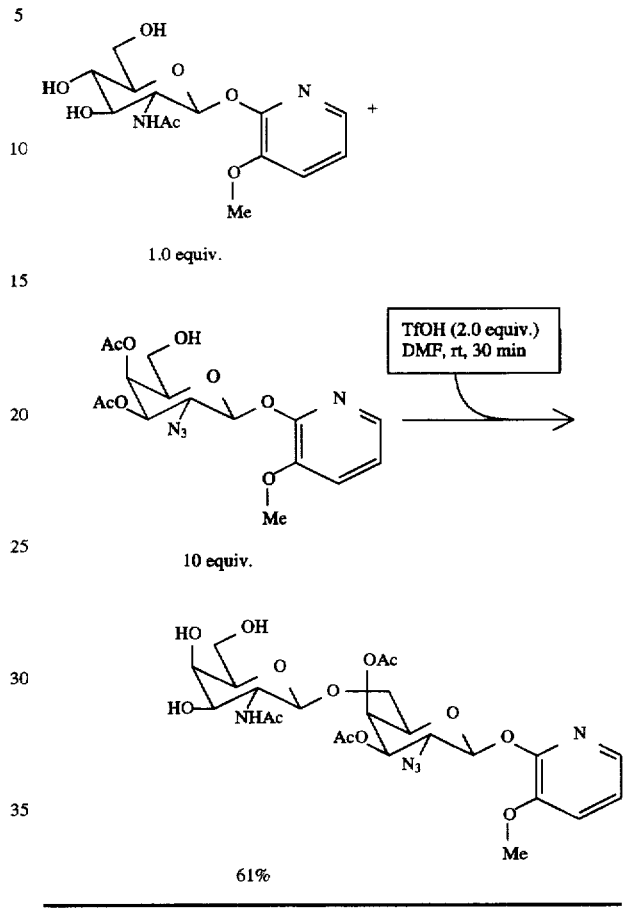

TABLE XI

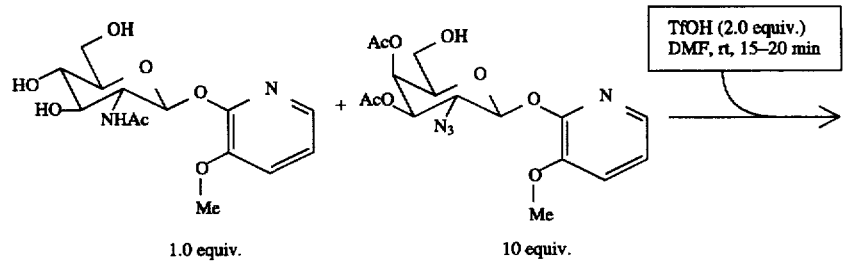

TABLE XI-continued
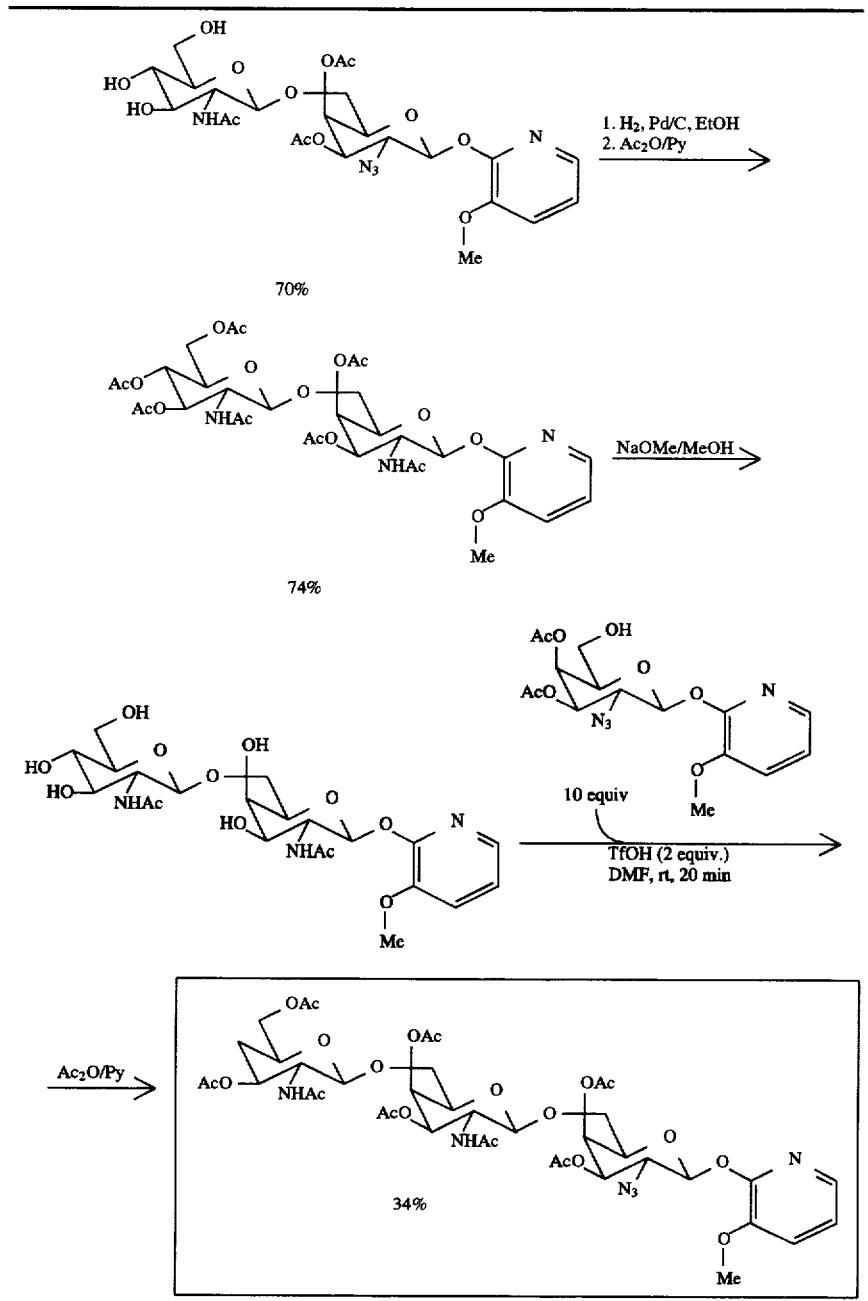
In a close variation on the immediately preceding synthesis, the identical disaccharide is prepared, deprotected and treated with 0.5 eq. MeOTf, CH₃NO₂/iPrOH, at room temperature for 9 hours followed by peracetylation, to give the isopropyl derivative of the disaccharide in 66% yield, alpha:beta 17:1, Table XII.

TABLE XII

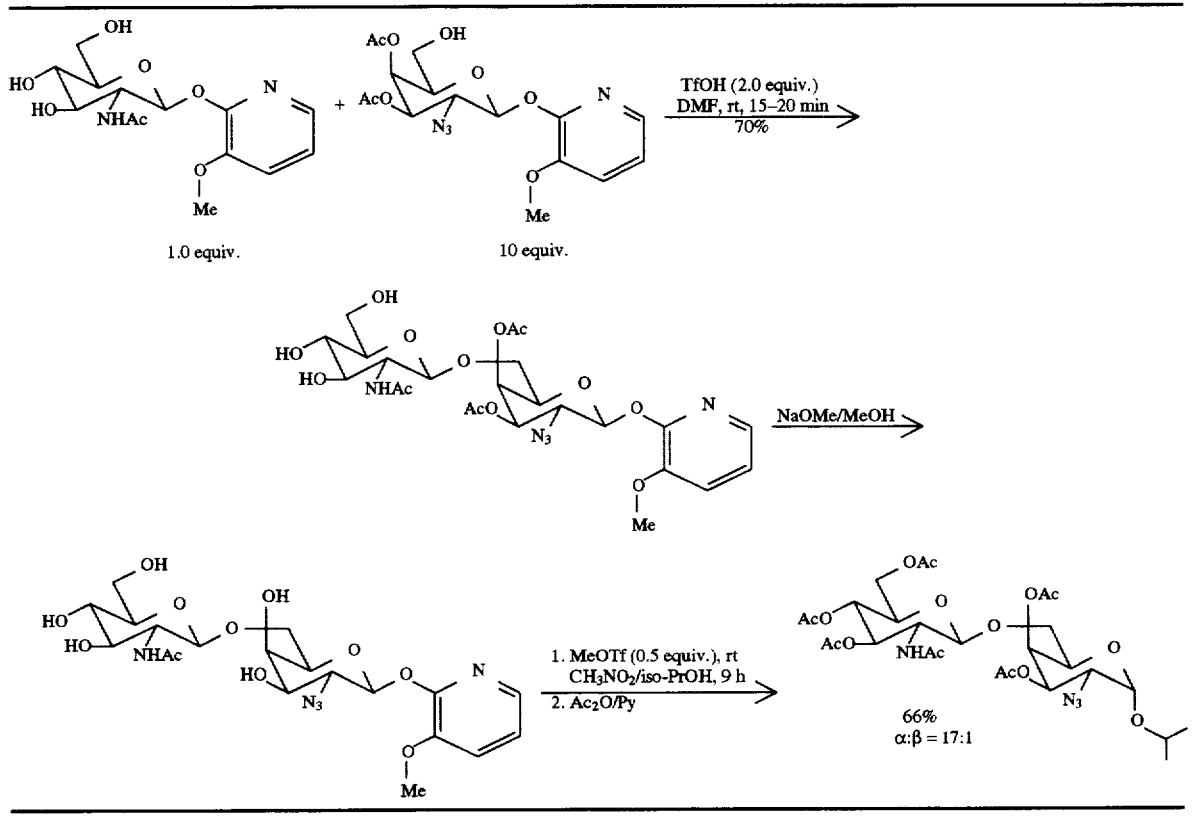

ACTIVATION OF O-ACYL PROTECTED GLYCOSYL MOP DONORS FOR BETA-GLYCOSIDE SYNTHESIS-COPPER TRIFLATE ACTIVATOR

O-acyl protected 1,2-trans MOP glycosyl donors are coupled with glycoside acceptors containing a single free hydroxyl, using $Cu(OTf)_2$ (2 eq.), $CH_2Cl_2$ solvent at room temperature for 2 to 8 h, gave beta linked D-glycopyranosyl disaccharides in 60–85% yield, Table XIII.

TABLE XIII

TABLE XIII-continued

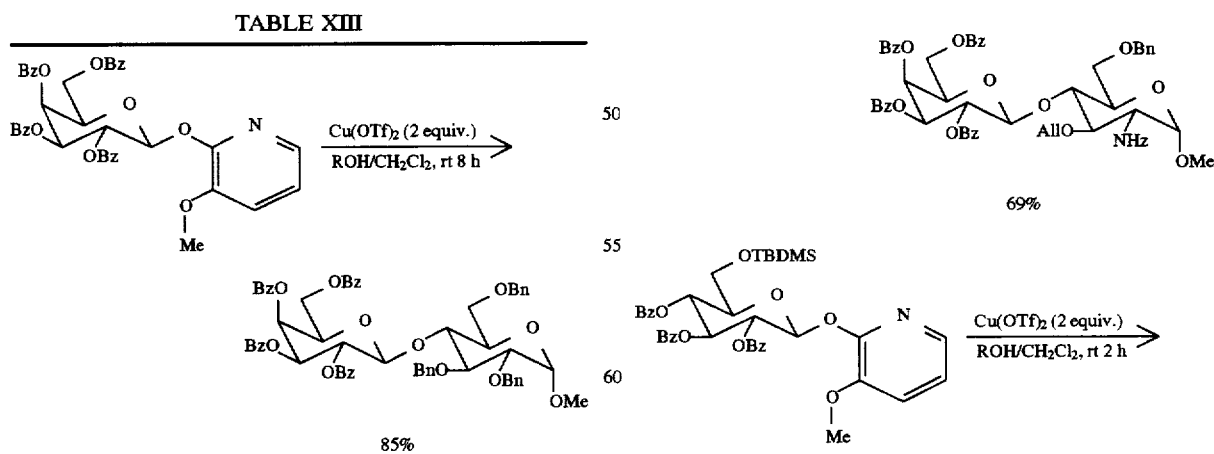

TABLE XIII-continued

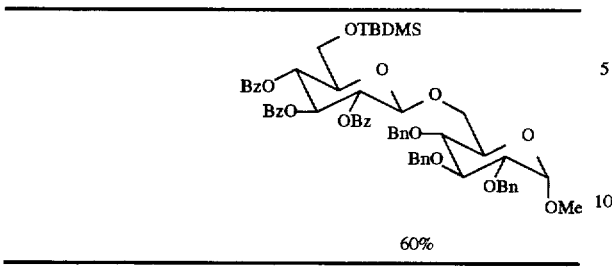

60%

A number of D-glucopyranoside beta MOP donors unprotected, protected by 6-O-TBDMS, 3,4,6-O-benzyl, 2,3,4-O-benzyl and 2,3,4,6-O-benzyl were treated with MeOTf (0.2 eq) in $CH_3NO_2$/iPrOH, at room temperature, the yields varied from 76-95%, with alpha:beta ratios from 5:1 to 100% alpha. Reaction time and alpha proportion tended to increase with total bulk of protecting groups.

GLYCOSIDE SYNTHESIS WITH O-ETHER PROTECTED GLYCOSYL MOP DONORS

Perbenzylated glucopyranosyl beta MOP donor was treated in the presence MeOTf 0.2 eq., in ether at room temperature with 1.5 eq. of 6-hydroxy acceptors protected with isopropylidene, and acetyl groups, for 24 and 20 hours respectively to give 66% yield of 5.7:1 alpha:beta and 64% yield of 5:1 alpha:beta Table XIV.

TABLE XIV

Perbenzylated glucopyranosyl beta MOP donor was treated in the presence of MeOTf 0.5 eq., in ether at room temperature, 15 h, with 1.5 eq. of 6-hydroxy diacetyl azidodeoxy glucopyranosyl beta MOP latent donor as acceptor, to give 55% yield of 4.5:1 alpha:beta. The same donor was treated in the presence MeOTf 0.5 eq., in ether/$CH_2Cl_2$ at room temperature, 3 h, with 1.5 eq. of 6-hydroxy tribenzoyl glucopyranosyl beta MOP latent donor as acceptor, to give 52% yield of disaccharide alpha:beta 6:1. The same donor was treated in the presence MeOTf 0.5 eq., in ether/$CH_2Cl_2$ at room temperature, 3 h, with 1.5 eq. of 6-hydroxy tri-p-fluorobenzoyl glucopyranosyl beta MOP latent donor as acceptor, to give 60% yield of disaccharide alpha:beta 6:1 Table XV. Not shown in this table but but related thereto treatment of the galactopyranosyl beta MOP donor in the presence of MeOTf 1 eq., in $CH_3NO_2$/DMF, 15 m, with 0.5 eq. of 6-hydroxy tri-p-fluorobenzoyl galactopyranosyl beta MOP latent donor as acceptor, to give 62% yield of disaccharide alpha:beta 6:1. The identical procedure was used for glucopyranosyl beta MOP donor with 6-hydroxy tri-p-fluorobenzoyl glucopyranosyl beta MOP latent donor as acceptor, to give 68% yield of disaccharide alpha:beta 4:1; galactopyranosyl beta MOP donor with 6-hydroxy tri-p-fluorobenzoyl glucopyranosyl beta MOP latent donor as acceptor, to give 65% yield of disaccharide (after acetylation) alpha:beta 6:1.

TABLE XV

TABLE XV-continued

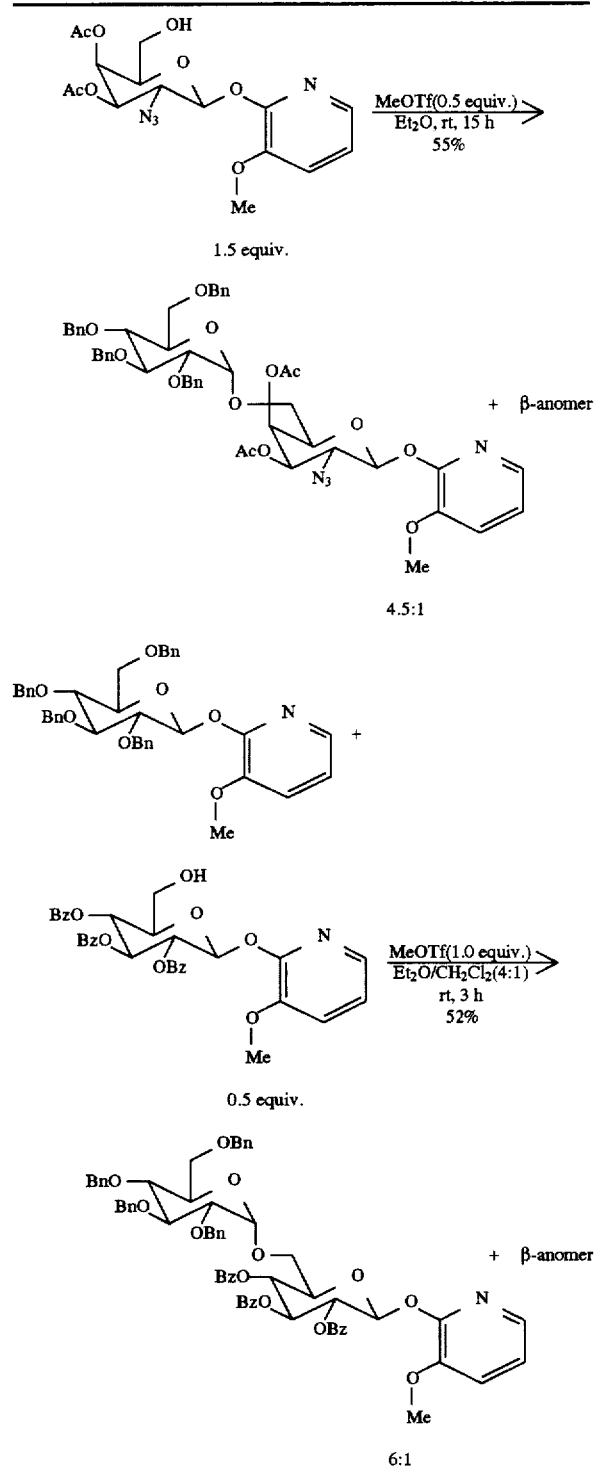

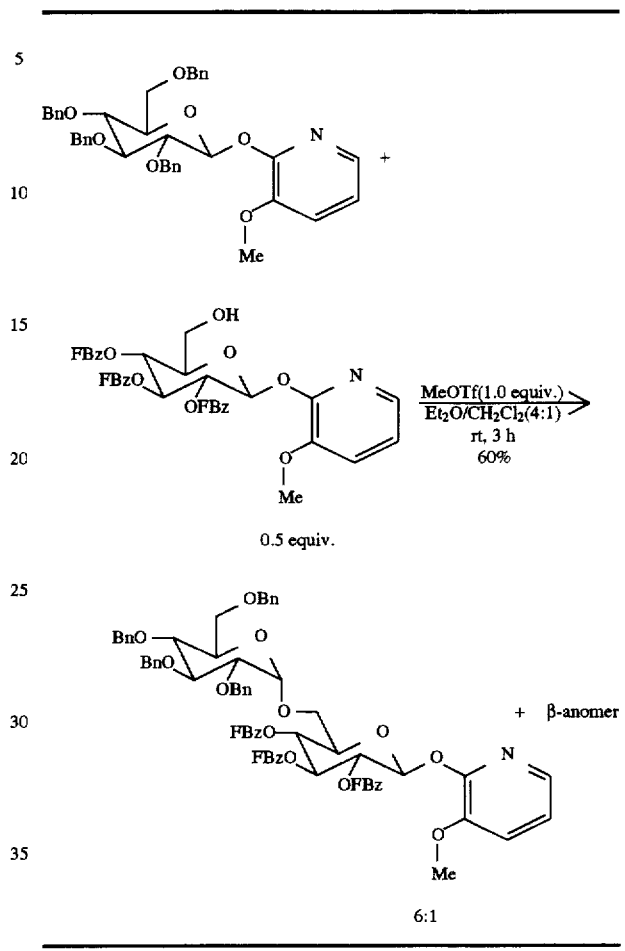

Perbenzylated glucopyranosyl beta MOP donor was treated in the presence of Cu(OTf)$_2$ 1.0 eq., in ether at room temperature, 12 h, with methyl 2,3,4, tri-O-acetyl beta-D-glucopyranoside as acceptor, to give 75% yield of disaccharide, alpha:beta 5.8:1. The same reaction in CH$_3$CN in 15 minutes gave 67% yield alpha:beta 1:2.6, favoring a beta-glycosidic linkage in this solvent. Perbenzylated glucopyranosyl beta MOP donor was treated with Cu(OTf)$_2$ 1.0 eq., in ether at room temperature, 3.5 h, with cholesterol acceptor, to give 78% yield, alpha:beta 4:1. Perbenzylated glucopyranosyl alpha MOP donor was treated with Cu(OTf)$_2$ 1.0 eq., in ether at room temperature, 20 min, 4A MS, with methyl 2,3,4-tri-O-acetyl-alpha-D-glucopyranoside as acceptor, to give 73% yield of disaccharide alpha:beta 4.3:1, Table XVI.

TABLE XVI
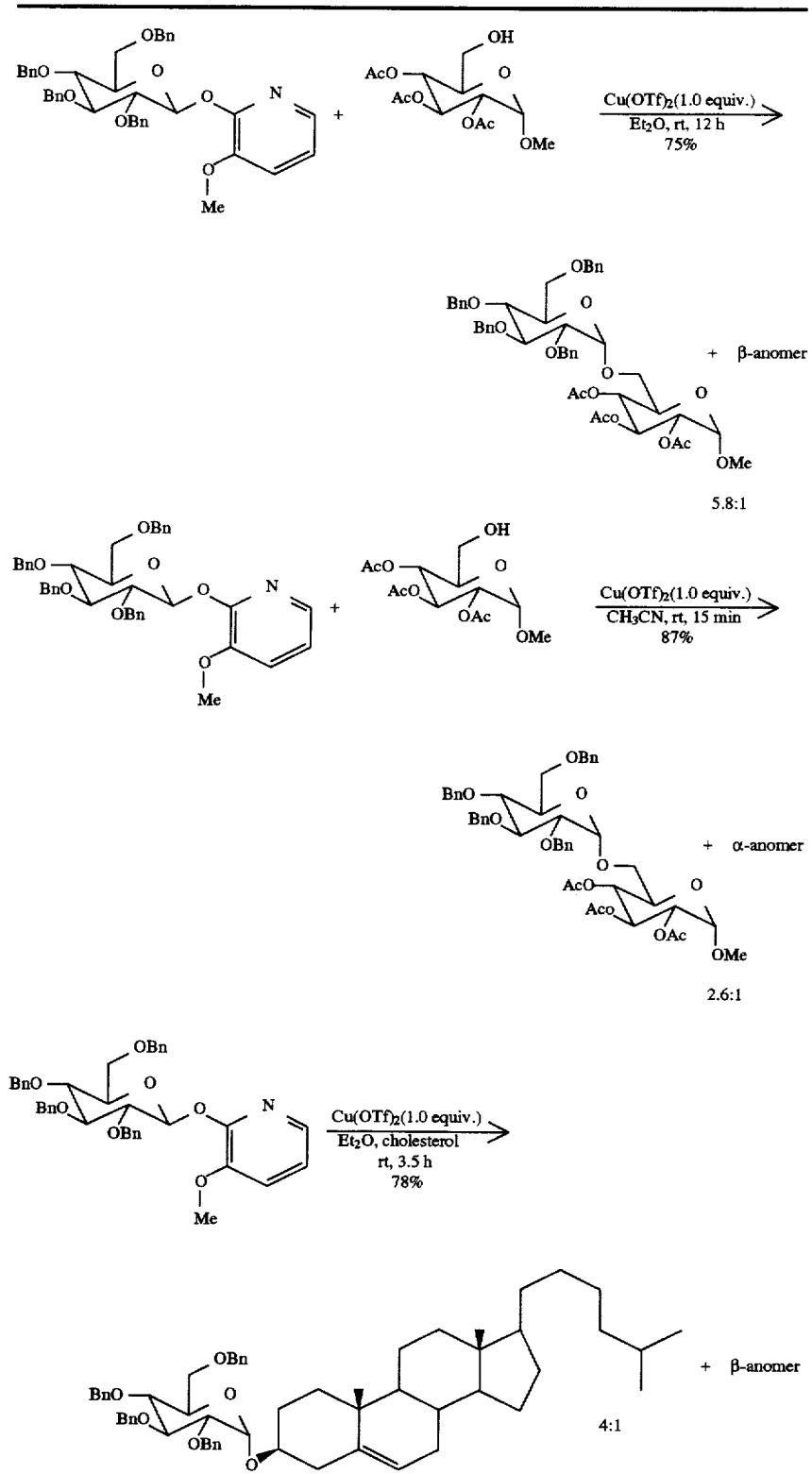

TABLE XVI-continued

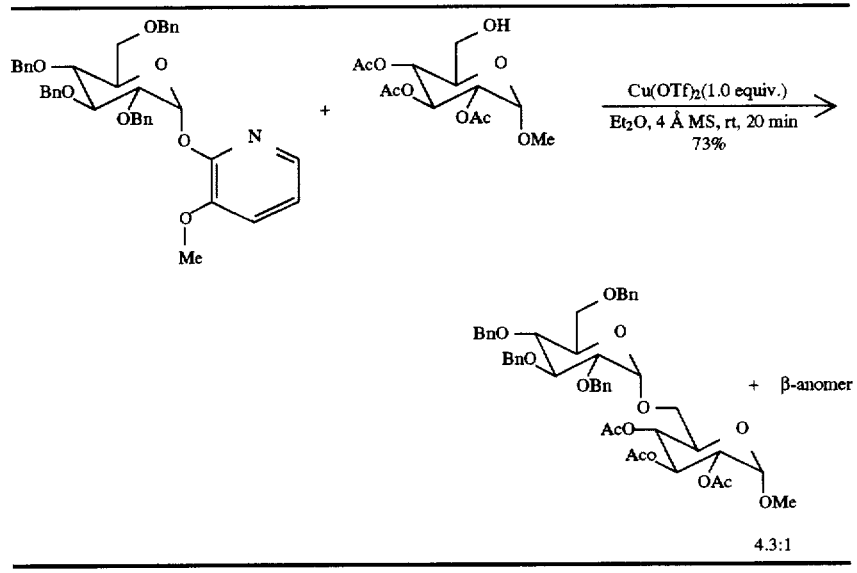

Perbenzylated 2-azido-2-deoxy-galactopyranosyl beta MOP donor was treated with $Cu(OTf)_2$ 1.2 eq., in $CH_2Cl_2$ at room temperature, 6 h, with methyl 2,3,4-tri-O-acetyl-alpha-D-glucopyranoside acceptor, to give 90% yield of disaccharide, alpha:beta 3.2:1. The same reaction with $Cu(OTf)_2$ 2.2 eq., in $CH_3CN$ in 12 h gave 60% yield of disaccharide, alpha:beta 1:2.6 Table XVII.

TABLE XVII

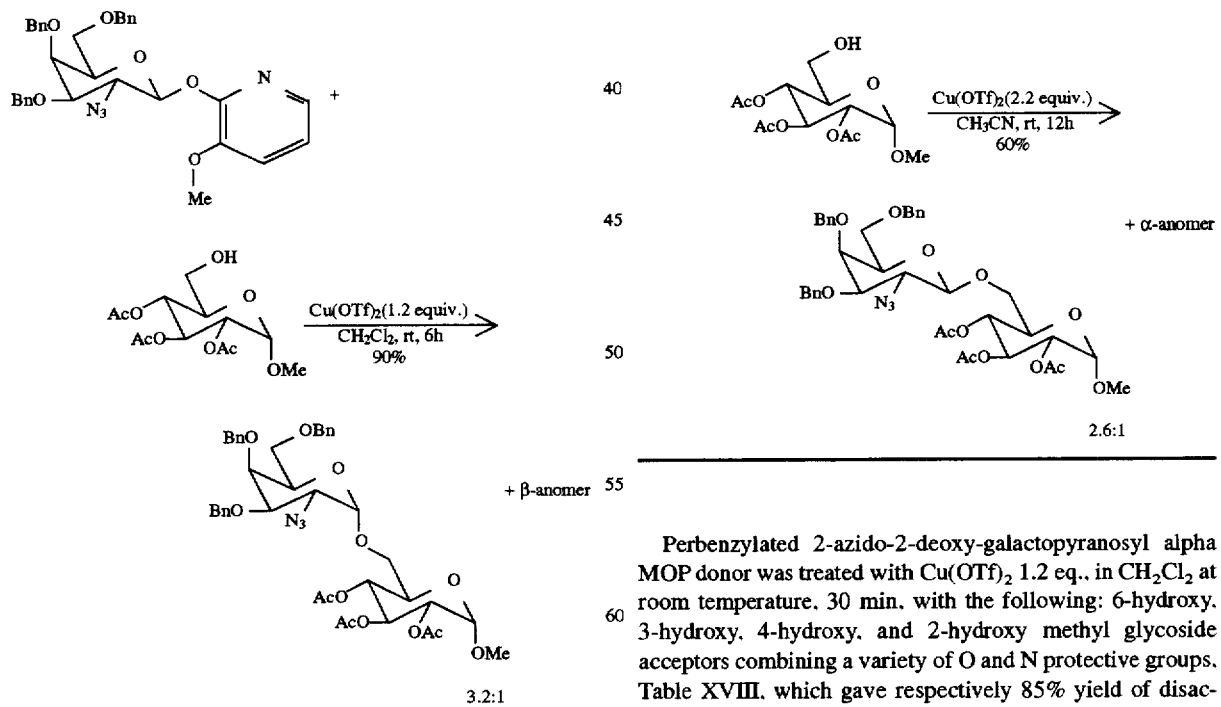

TABLE XVII-continued

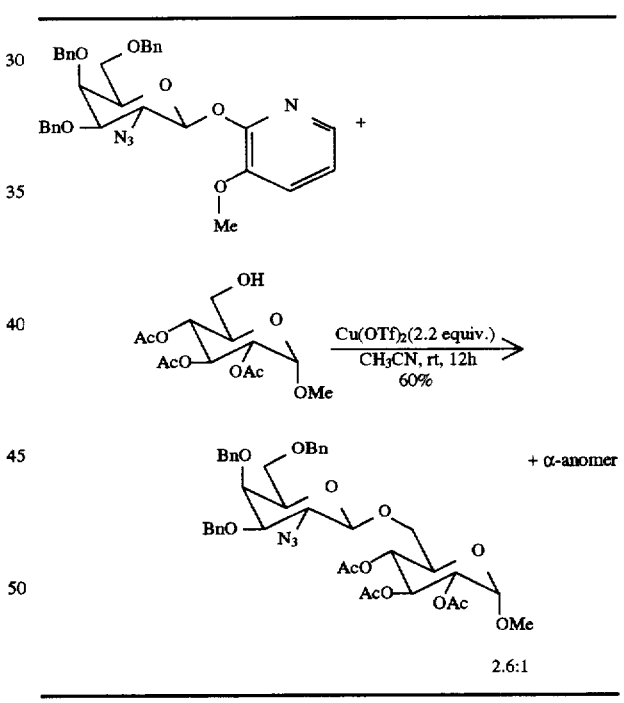

Perbenzylated 2-azido-2-deoxy-galactopyranosyl alpha MOP donor was treated with $Cu(OTf)_2$ 1.2 eq., in $CH_2Cl_2$ at room temperature, 30 min, with the following: 6-hydroxy, 3-hydroxy, 4-hydroxy, and 2-hydroxy methyl glycoside acceptors combining a variety of O and N protective groups, Table XVIII, which gave respectively 85% yield of disaccharide (alpha:beta 3:1), 53% yield (100% alpha), 63% yield (alpha:beta 6:1), and 48% yield (alpha:beta 4.2:1).

TABLE XVIII

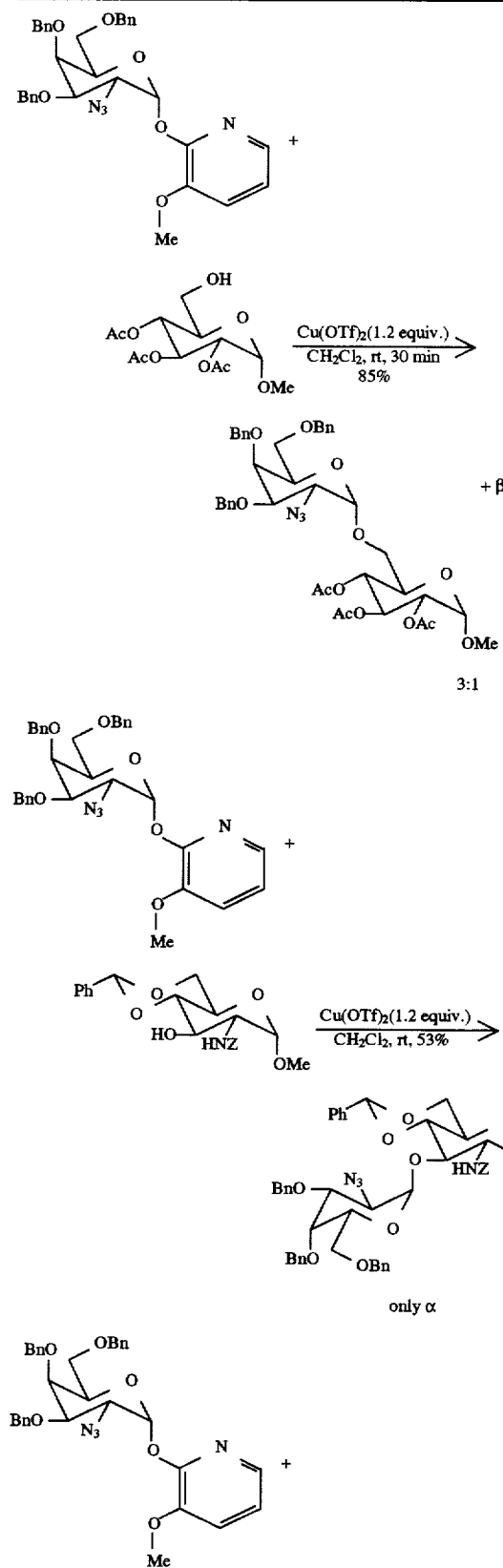

TABLE XVIII-continued

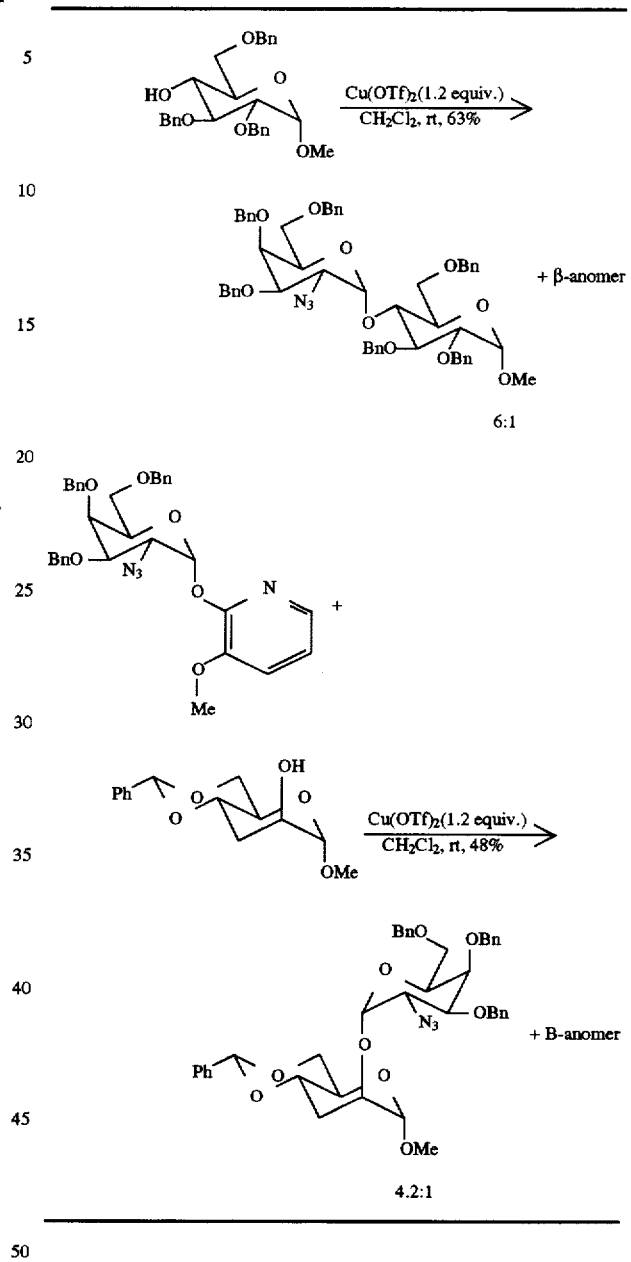

Perbenzylated glucopyranosyl beta MOP donor (1.5 eq.) was treated with $Cu(OTf)_2$ 1 eq., in $CH_2Cl_2$ at room temperature, 8 h, with methyl 3-O-acetyl-4,6-O-benzylidene-alpha-D-glucopyranoside as acceptor to give yield 45% of disaccharide, alpha:beta 2.4:1. Perbenzylated glucopyranosyl beta MOP donor (1.5 eq.) was treated with Cu(OTf)2 1 eq., in $CH_2Cl_2$/ether (1:4) at room temperature, 15 h, and methyl 2-O-acetyl-4,6-O-benzylidene-alpha-D-glucopyranoside acceptor to give yield 60% of disaccharide, alpha:beta 10:1. Perbenzylated glucopyranosyl beta MOP donor (1.5 eq.) was treated with $Cu(OTf)_2$ 1 eq., in $CH_2Cl_2$ at room temperature, 9 h, with methyl 2,3,6 tri-O-benzyl alpha-D-glucopyranoside acceptor to give yield 50% of disaccharide, alpha:beta 2:1, Table XIX.

TABLE XIX

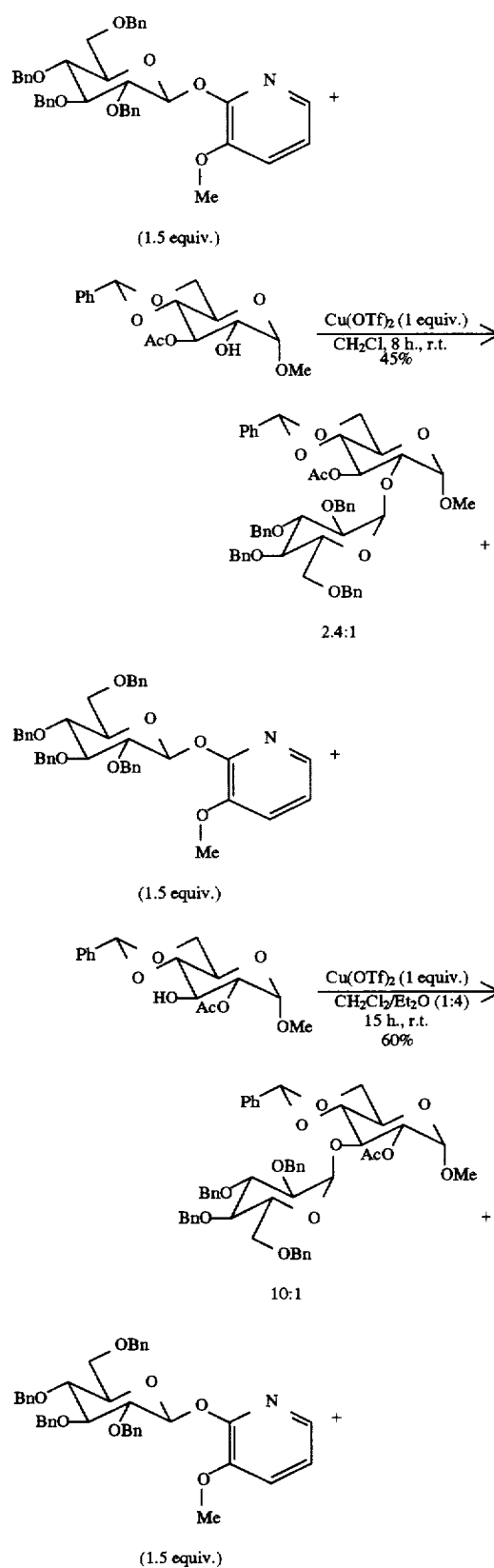

TABLE XIX-continued

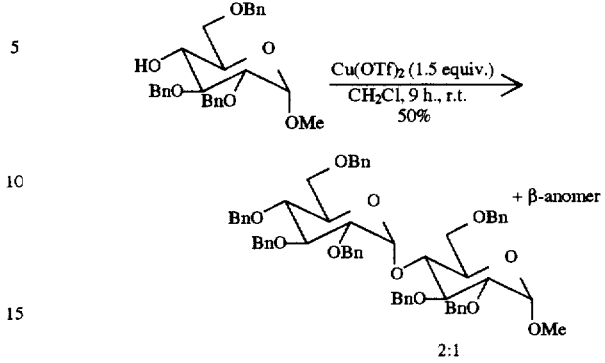

Perbenzylated galactopyranosyl beta MOP donor (1.5 eq.) was treated with Cu(OTf)₂ 1 eq., in CH₂Cl₂ at room temperature, 6 h, with 3-O-acetyl 4,6-O-benzylidene-alpha-D-glucopyranoside acceptor to give yield 85% of disaccharide, alpha 100%. Perbenzylated galactopyranosyl beta MOP donor (1.5 eq.) was treated with Cu(OTf)₂ 1 eq., in CH₂Cl₂ at room temperature, 7 h, and methyl 2-O-acetyl-4,6-benzylidene-alpha-D-glucopyranoside acceptor to give yield 60% of disaccharide, alpha 100%. Perbenzylated galactopyranosyl beta MOP donor (1.5 eq.) was treated with Cu(OTf)₂ 1 eq., in CH₂Cl₂ at room temperature, 24 h, with methyl 2,3,6 tri-O-benzyl alpha-D-glucopyranoside as acceptor to give yield 60% of disaccharide, alpha 100% Table XX. Perbenzylated galactopyranosyl beta MOP donor (1.5 eq.) was treated with Cu(OTf)₂ 1 eq., in CH₂Cl₂ at room temperature, 9 h, and methyl 4,6-O-benzylidene-2-benzyloxycarbonylamino-2-deoxy-alpha-D-glucopyranoside acceptor to give yield 45% of disaccharide, alpha 100%. Perbenzylated galactopyranosyl beta MOP donor (1.5 eq.) was treated with Cu(OTf)₂ 1 eq., in CH₂Cl₂ at room temperature, 15 h, and methyl 2,3,4-tri-O-acetyl alpha-D-glucopyranoside acceptor to give yield 85% of the disaccharide, alpha:beta 3:1, Table XXI. In the same table is shown treatment of the MOP 1,4 2,3,4,6-O-tetracetyl-beta-D-galactopyranosyl-4,6-O-isopropylidenyl-2-azido-2-deoxy-alpha-galactopyranoside with benzyl-N-benzoylserine, in CH₂Cl₂, 4A MS, in the presence of Cu(OTf)₂ to give 82% yield, alpha:beta 4:1.

TABLE XX

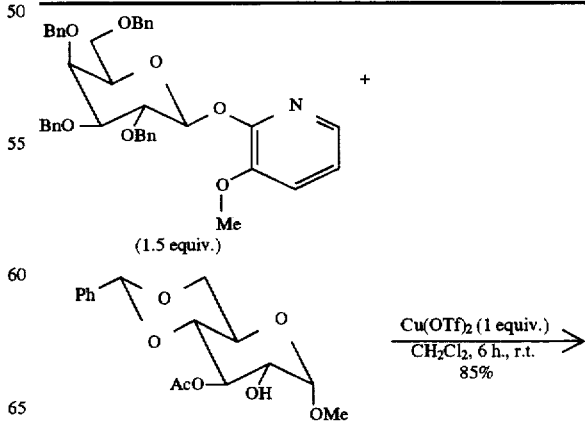

TABLE XX-continued
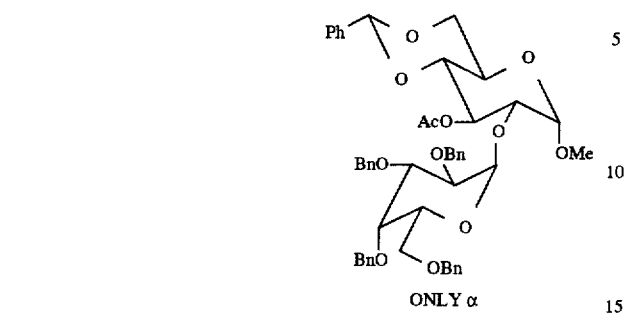
ONLY α
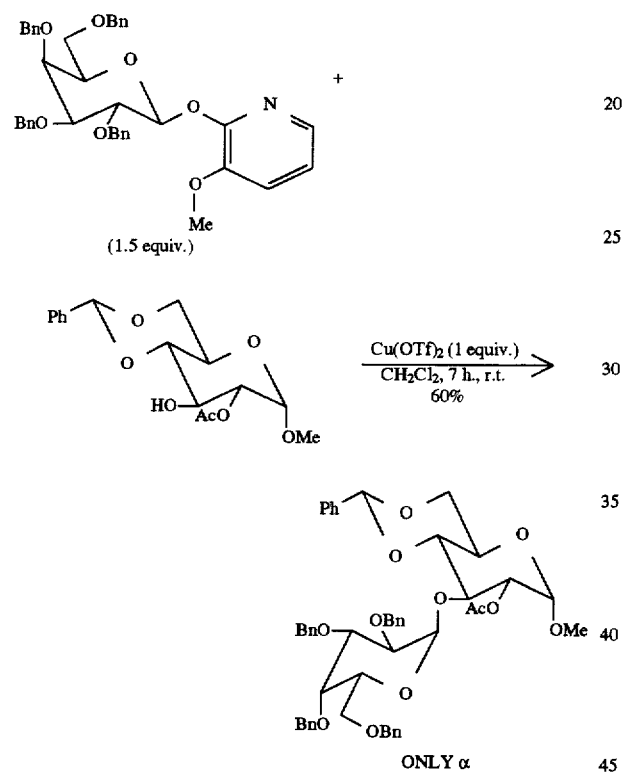
ONLY α
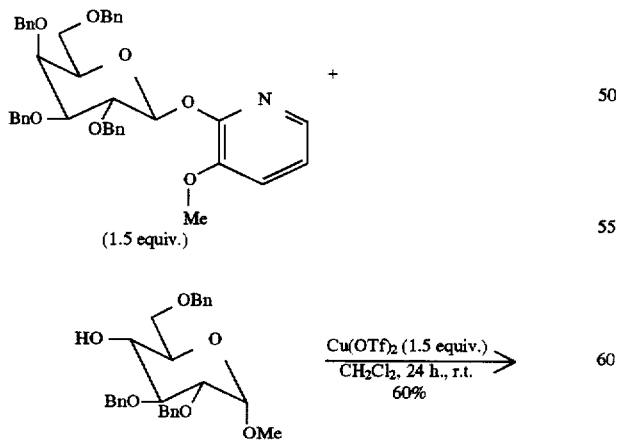
TABLE XX-continued
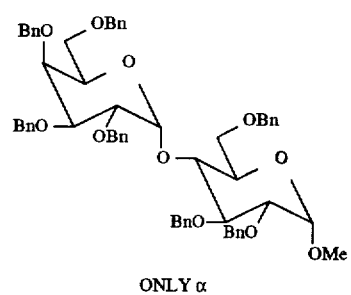
ONLY α
TABLE XXI
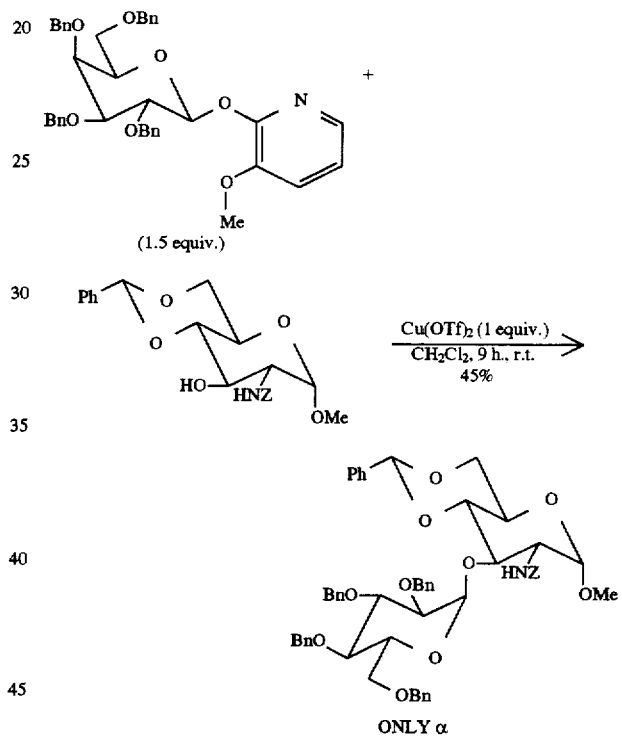
ONLY α
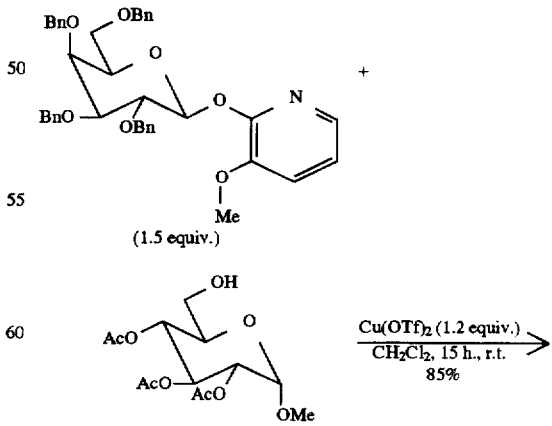

TABLE XXI-continued

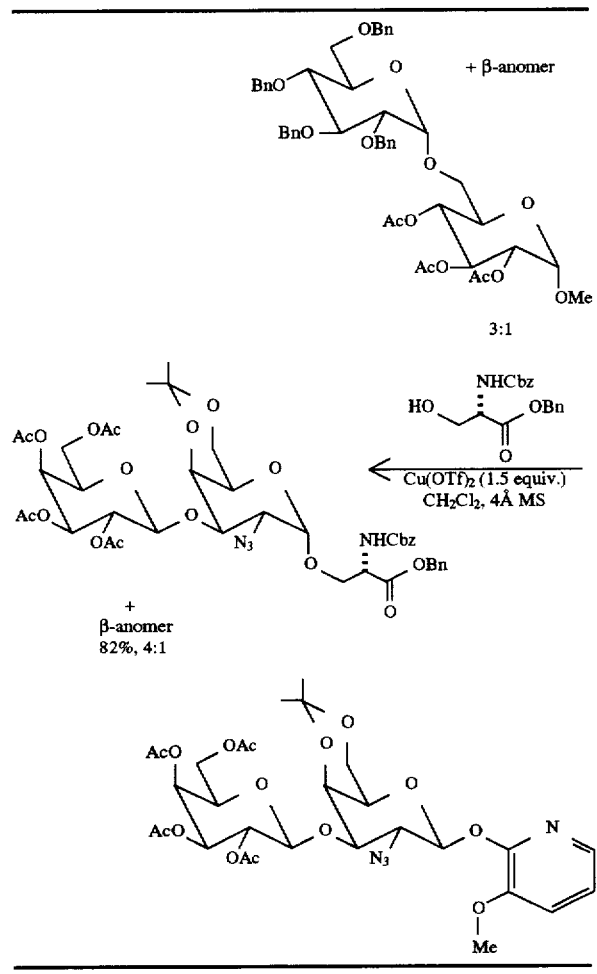

In summary the 2-(3-methoxy)-pyridyl MOP beta-D-hexopyranosides, exemplified by analogs in the D-gluco-, D-galacto- and their 2-azido-2-deoxy variants (1,2-trans MOP glycosides) with hydroxyl acceptors, (alcohols and carbohydrates) in suitable solvents give primarily alpha products (1,2-cis products) in the presence of MeOTf as promoter, in catalytic proportion, five other related leaving groups did not. MOP (3-methoxypyridyl-2-oxy) was shown superior (shorter) in reaction time to 2-oxypyridyl, and 4-methoxypyridyl-2-oxy, although closely similar in yield and alpha proportion. The unprotected beta 2-acetamido MOP glycosides gave exclusively beta products under similar conditions. The peracetylated MOP glycosides were unreactive as glycosyl donors. Ether protected equivalents were reactive as donors to give alpha products, in the presence of Cu(OTf)$_2$. Increasing degree of protection lengthened reaction time and increased alpha proportion. Perbenzylated beta MOP glycosides gave alpha disaccharide products. Solvent dependency was noted, water miscible alcohols may be used as solvent and donor with excellent results, apart from this coincidence, the solvent is fairly critical CH$_3$NO$_2$, CH$_2$Cl$_2$, and ether, gave satisfactory to excellent results for alpha glycosides while CH$_3$CN, favored the formation of beta-glycosides. For benzylated MOP glycosides, in the formation of C-glycosides, for example C-acyl, C-allyl, C-alkyl, etc., can be used.

NUCLEOSIDE SYNTHESIS USING MOP GLYCOSYL DONORS

In a further development MOP leaving groups have been utilized to prepare nucleosides. Clinically relevant nucleosides including AZT, used in the treatment of AIDS are known in the art. Prior syntheses of 1,2 cis-pyrimidine nucleosides, using hemiacetal sugar acetates with trimethylsilyl substituted ethyl and butyl uracils, and of 1,2 trans-pyrimidine nucleosides, and thymine derivatives are similarly prepared from thiophenyl hemiacetals, U. Niebdala and H. Vorbruggen, J. Org. Chem. 39, 3654 (1974), H. Sugimura, I. Muramolo, T. Nakamura, K. Osuml, Chem. Lett., 169 (1993). Perbenzylated galactopyranosyl beta MOP donor is allowed to react with trimethylsilyl uracil, thymine and cytosine in THF and toluene at room temperature using TMSOTf promote r, Table XXII, to give the expected beta-D-galactopyranosyl nucleosides in 55 to 95% yield with alpha:beta ratios of 6 to 9:91 to 94, showing excellent stereocontrol. Perbenzylated furanosyl nucleosides were prepared from trimethylsilyl thymine, Table XXIII, uracil, Table XXIV, and cytosine, Table XXV, and MOP perbenzylated furanosides, from inspection generally best yields and highest alpha proportion are obtained using toluene. Table XXVI shows a synthetic route to thymidines.

TABLE XXII

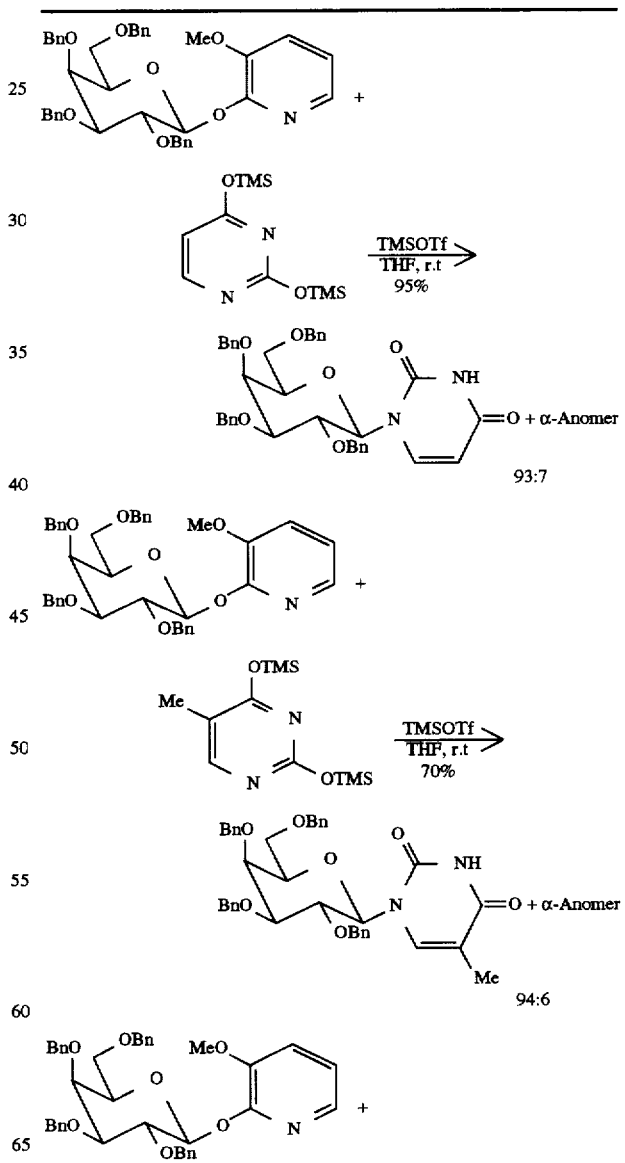

TABLE XXII-continued
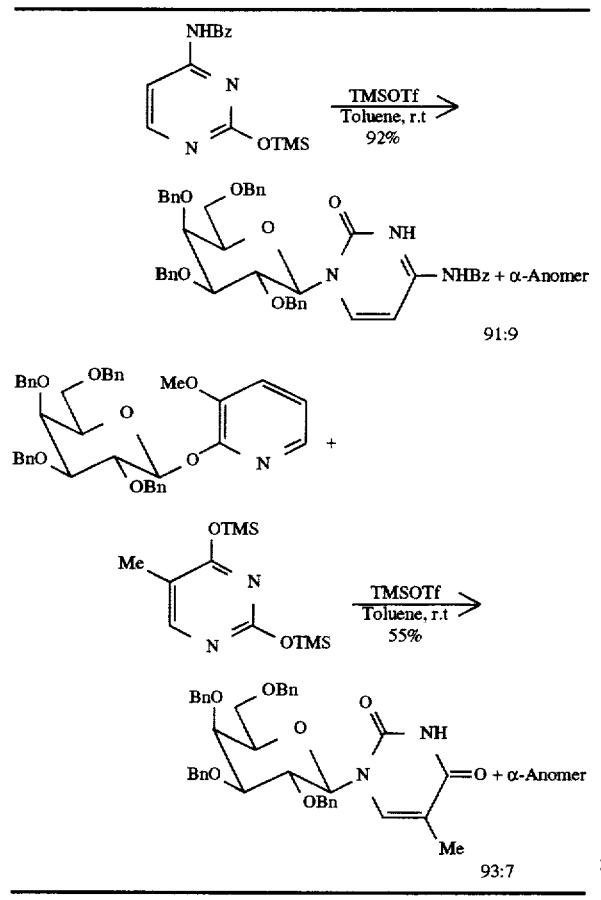
TABLE XXIII
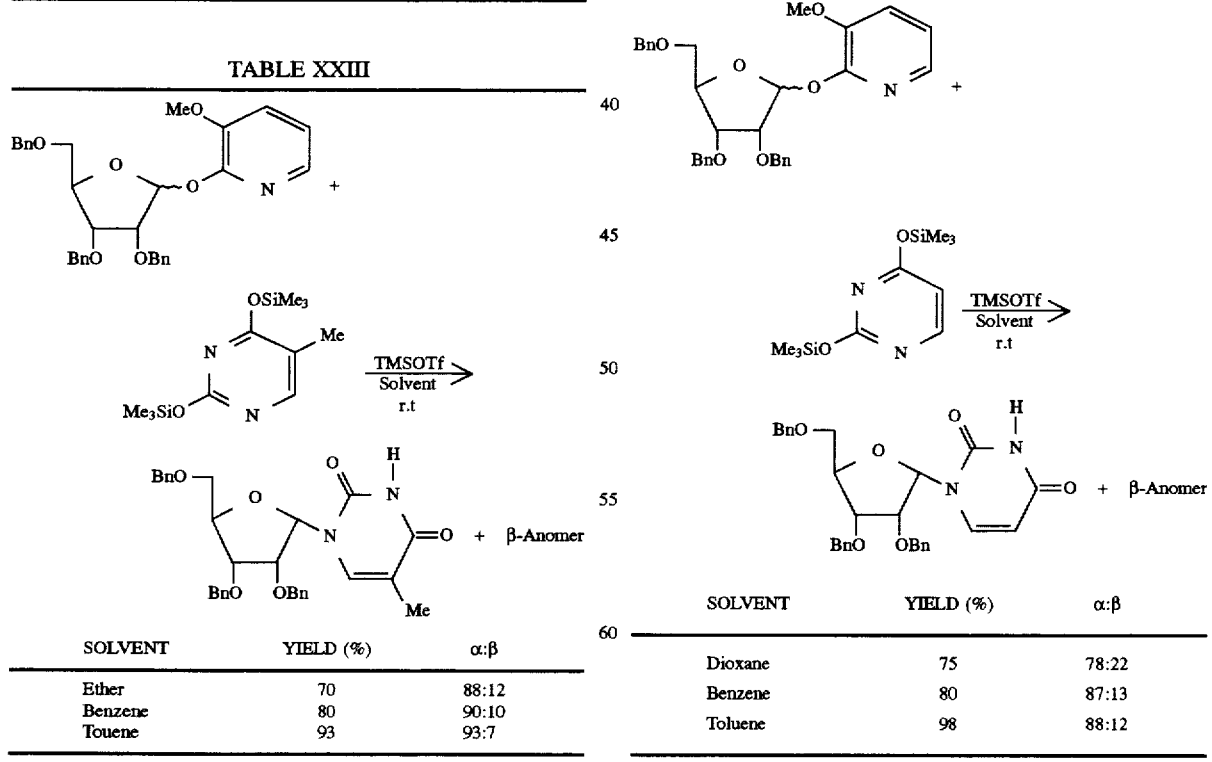
| SOLVENT | YIELD (%) | α:β |
|---|---|---|
| Ether | 70 | 88:12 |
| Benzene | 80 | 90:10 |
| Touene | 93 | 93:7 |
TABLE XXIII-continued
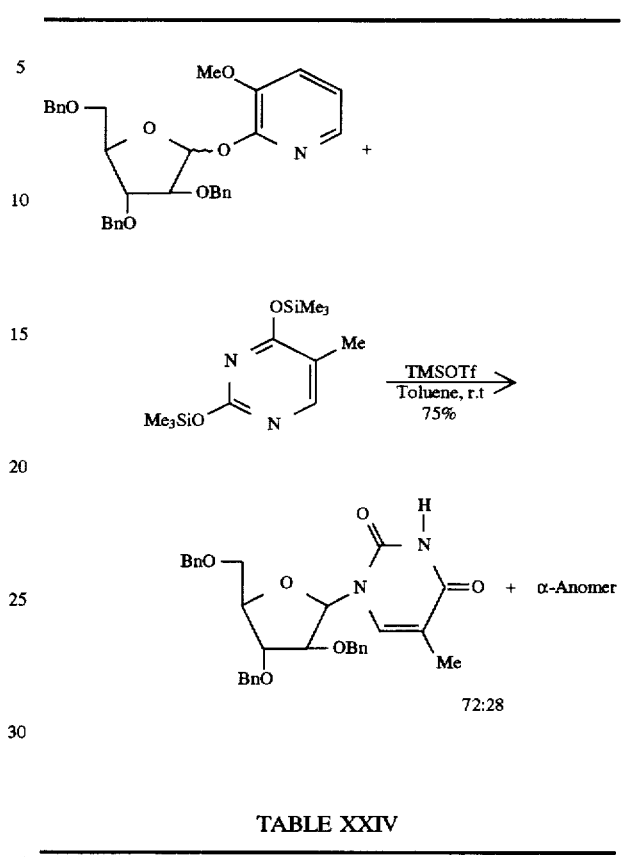
TABLE XXIV
| SOLVENT | YIELD (%) | α:β |
|---|---|---|
| Dioxane | 75 | 78:22 |
| Benzene | 80 | 87:13 |
| Toluene | 98 | 88:12 |

TABLE XXV
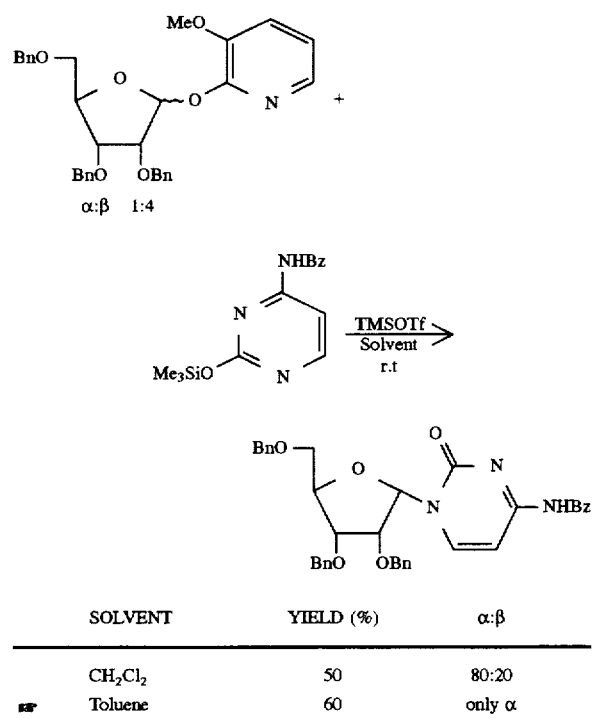
| SOLVENT | YIELD (%) | α:β |
|---|---|---|
| CH$_2$Cl$_2$ | 50 | 80:20 |
| ☞ Toluene | 60 | only α |
TABLE XXVI
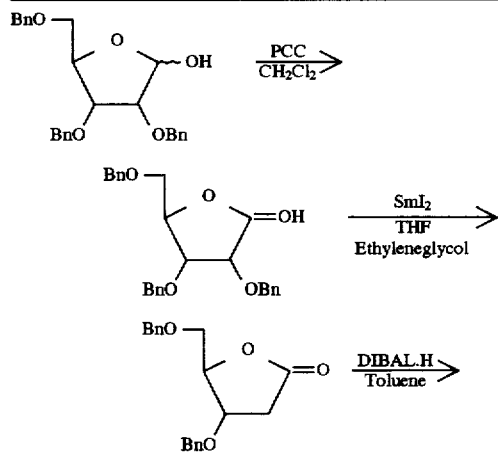
TABLE XXVI-continued
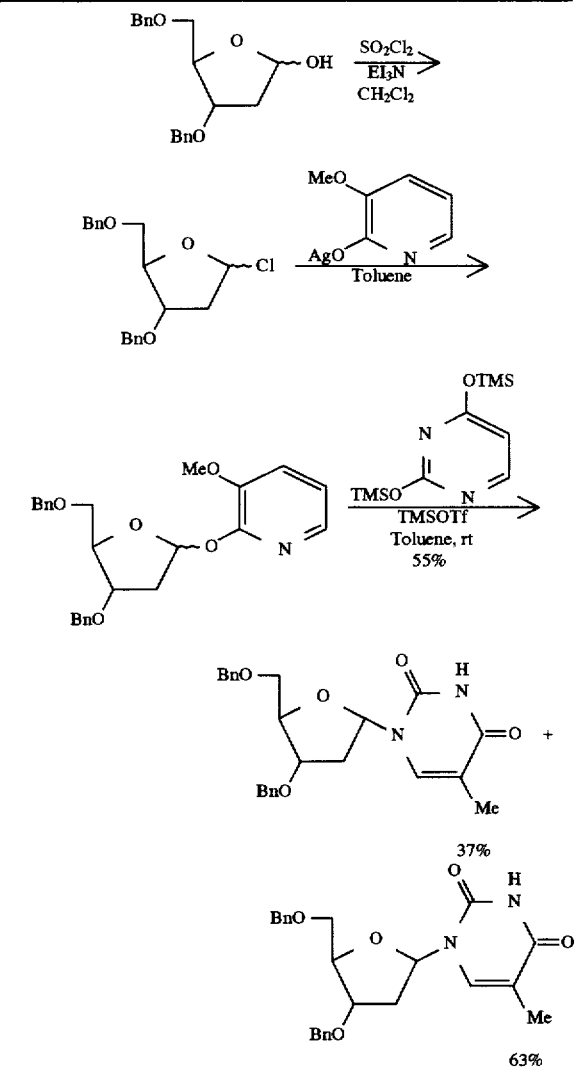
2-PYRIDYL CARBONATE DONORS
The idea of using 2-pyridyl carbonate as donor, was tested, showing reasonable yields and alpha-beta ratios, while the equivalent phenyl carbonate was inactive under similar conditions, Table XXVII.

TABLE XXVII
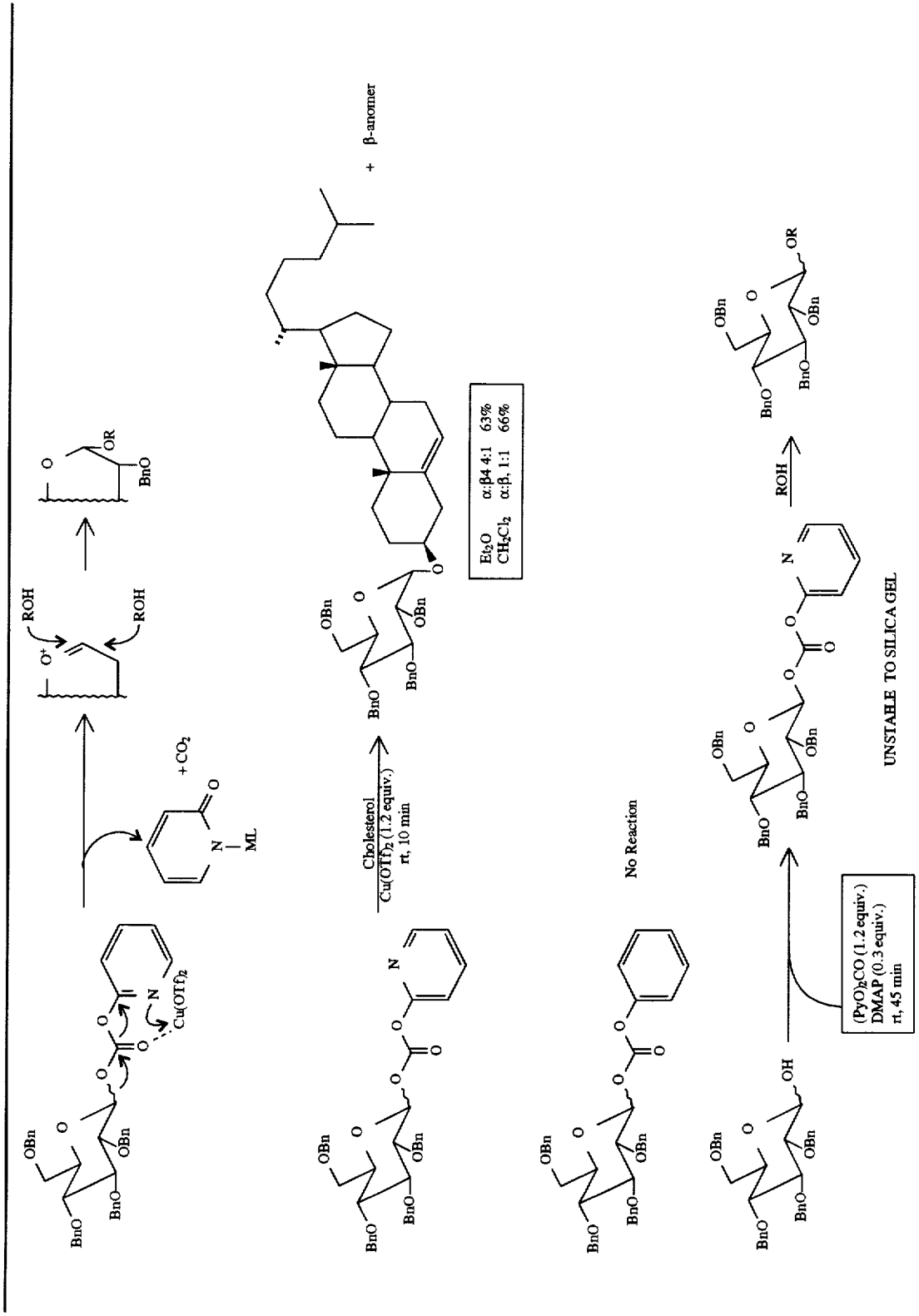

TABLE XXVII-continued
| ROH | Promoter(equiv.) | Solvent | Temp. (°C.) | Time | α:β | Yield (%) |
|---|---|---|---|---|---|---|
| 1 | Cu(OTf)$_2$(3) | Et$_2$O | −20–0 | 10 min | 3.6:1 | 60 |
| 1 | Cu(OTf)$_2$(3) | Et$_2$O | −20 | 4 hrs | 3.5:1 | 64 |
| 2 | Cu(OTf)$_2$(2.5)/HOTf(0.5) | Et$_2$O | −20–0 | 10 min | 2.5:1 | 63 |
| 2 | Cu(OTf)$_2$(2.5)/HOTf(0.5) | Et$_2$O | −20 | 3 hrs | 2:1 | 66 |
| 2 | Cu(OTf)$_2$(2.5)/HOTf(0.5) | CH$_3$CN | −20–0 | 1 hrs | 1:6 | 60 |
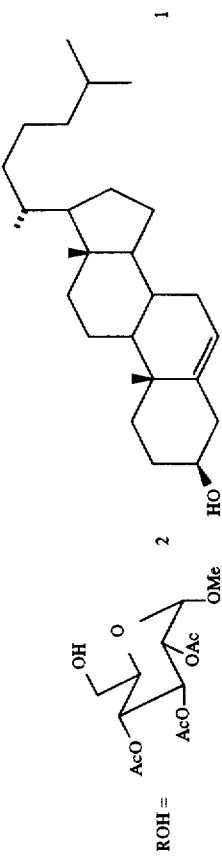
ROH =

2-PYRIDYL THIOCARBONATE DONORS

The concept of using the equivalent thiocarbonate relies on remote activation (S. Hauissian et al Carbohydrate Res.1 8v, CIF (1980)). The preparation of three of such thiocarbonate donors, hereinafter TOPCAT, and yields of others is shown, Table XXVIII, these compounds are all crystalline, stable, 1,2-trans isomers. TOPCAT perbenzyl alpha-D-glucopyranoside donor was tested with methyl 2,3,4-tri-O-acetyl alpha-d-glucopyranose, using as promoters 1.2 eq. Cu(OTf)$_2$ and 2 eq. AgOTf in ether and CH$_2$Cl$_2$, and then reacted in excess (1.5 eq.) with various glycosides and AgOTf (3' eq.). Table XXIX, yields of 40 to 80% with alpha:beta ratios of 4:1 to 1.5:1 were noted. The concept was further explored using TOPCAT alpha-D-galactopyranosyl, alpha-L-fucopyranosyl, and 1,2-trans glycosyl donors, the promoter was AgOTf, the solvent CH$_2$Cl$_2$, effectuated by 4 A MS, yields from 46 to 83% were obtained with alpha:beta ratios of 8:1 to 100% alpha, Table XXX.

TABLE XXVIII

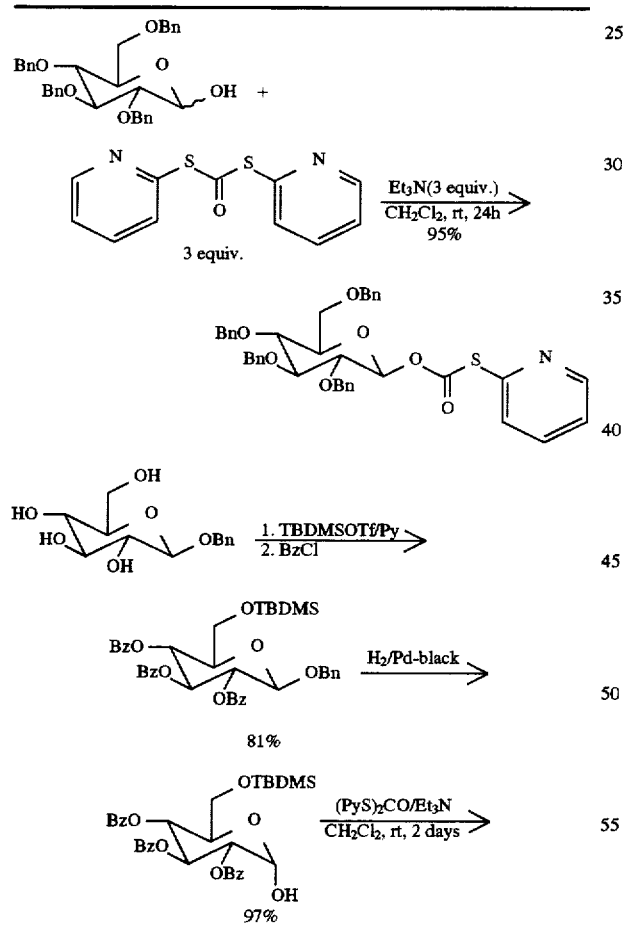

TABLE XXVIII-continued

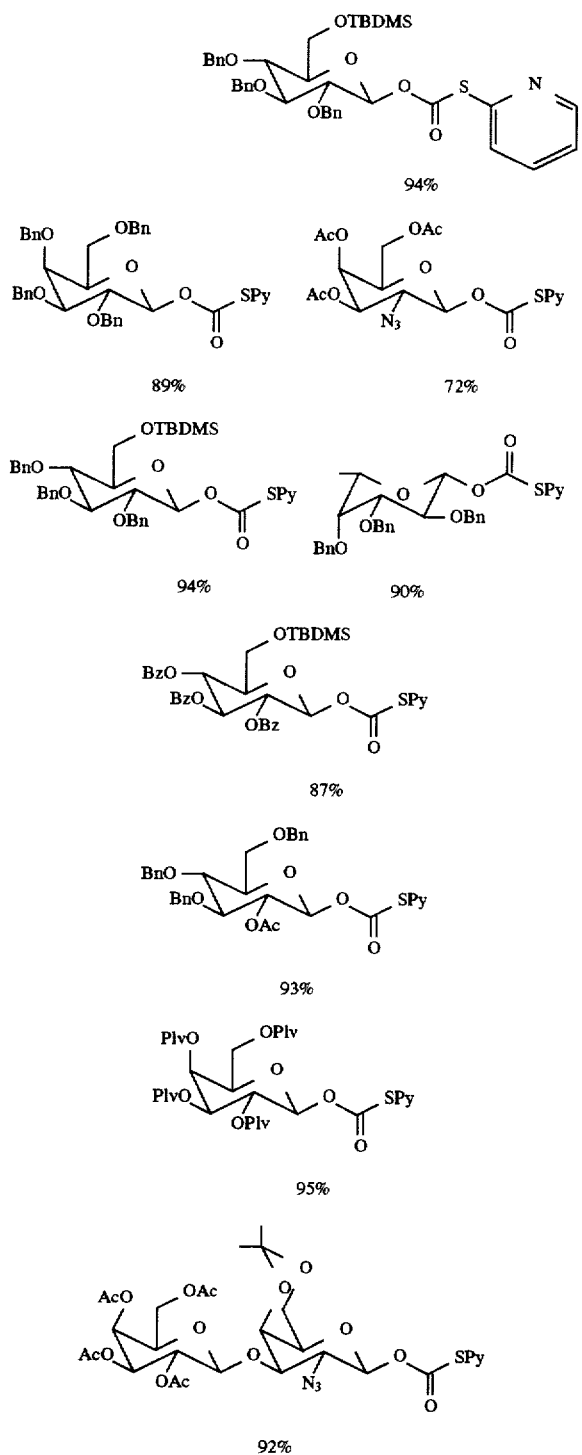

TABLE XXIX
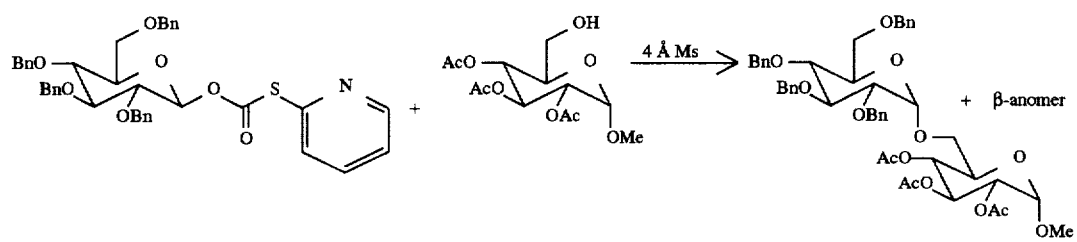
| Promoter(equiv.) | Solvent | Temp. (0° C.) | Time | α:β | Yield(%) |
|---|---|---|---|---|---|
| Cu(OTf)$_2$ (1.2) | ether | −20–0 | 2 hrs | 5.5:1 | 65 |
| Cu(OTf)$_2$ (1.2) | CH$_2$Cl$_2$ | −20–0 | 2 hrs | 3:1 | 69 |
| AgOTf(2.0) | ether | 0 | 15 min | 2.5:1 | 80 |
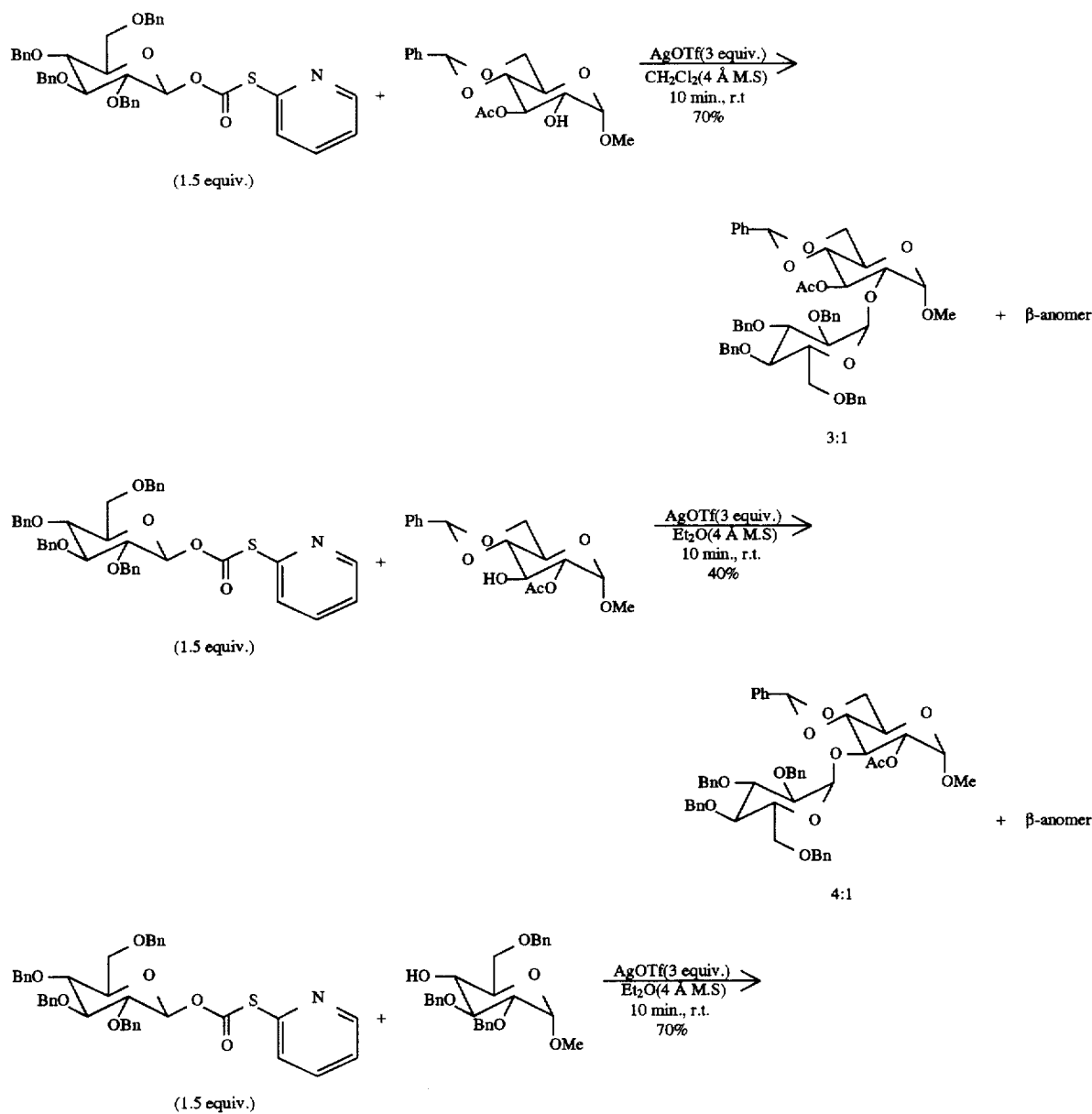

TABLE XXIX-continued
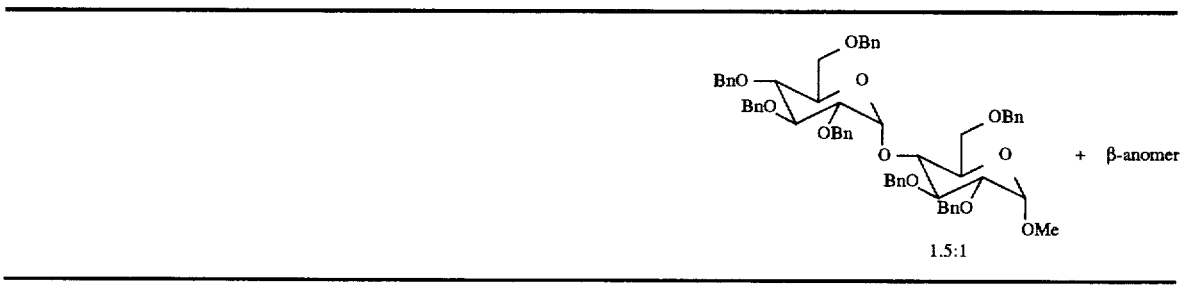
1.5:1
TABLE XXX
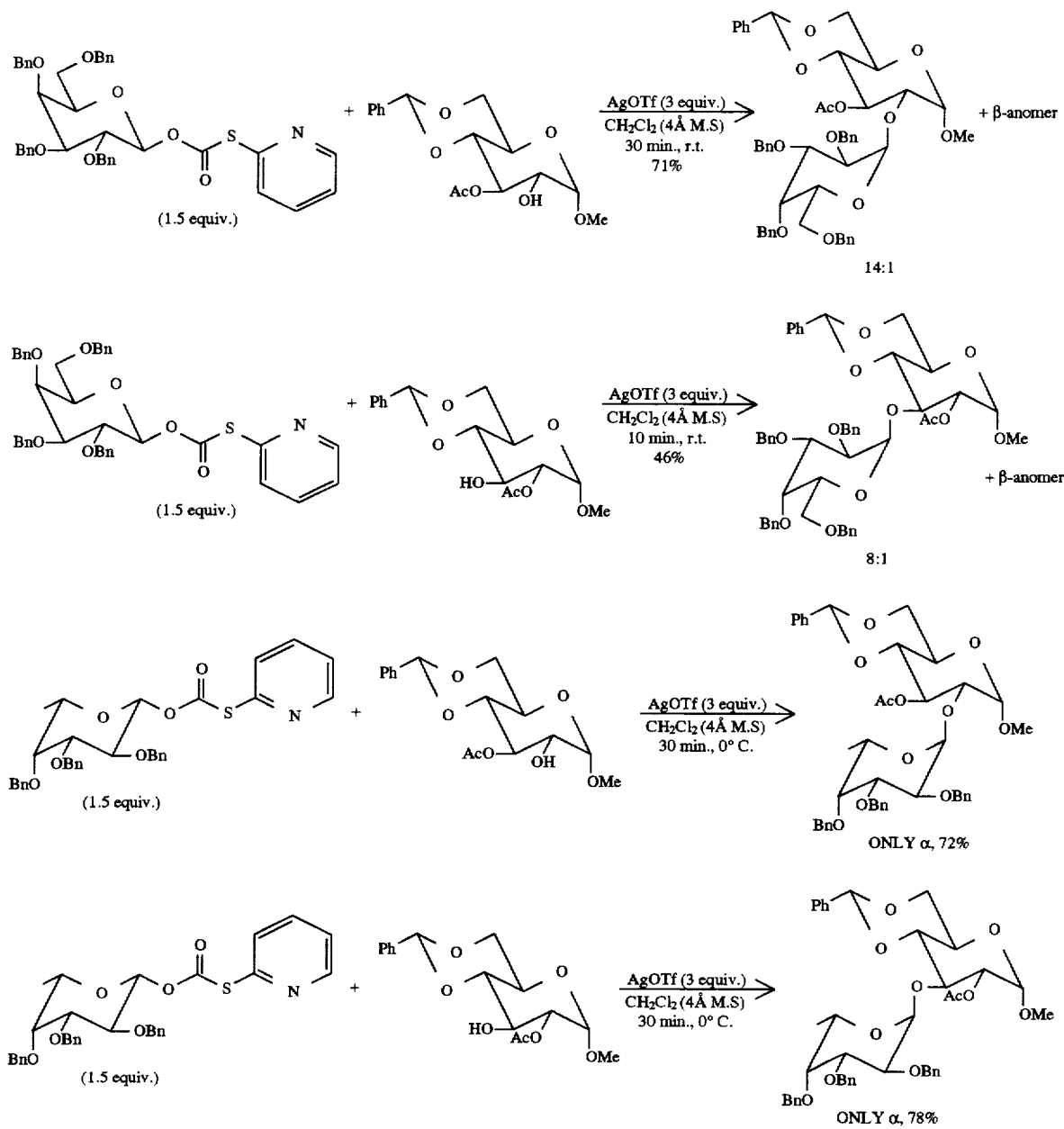

TABLE XXX-continued

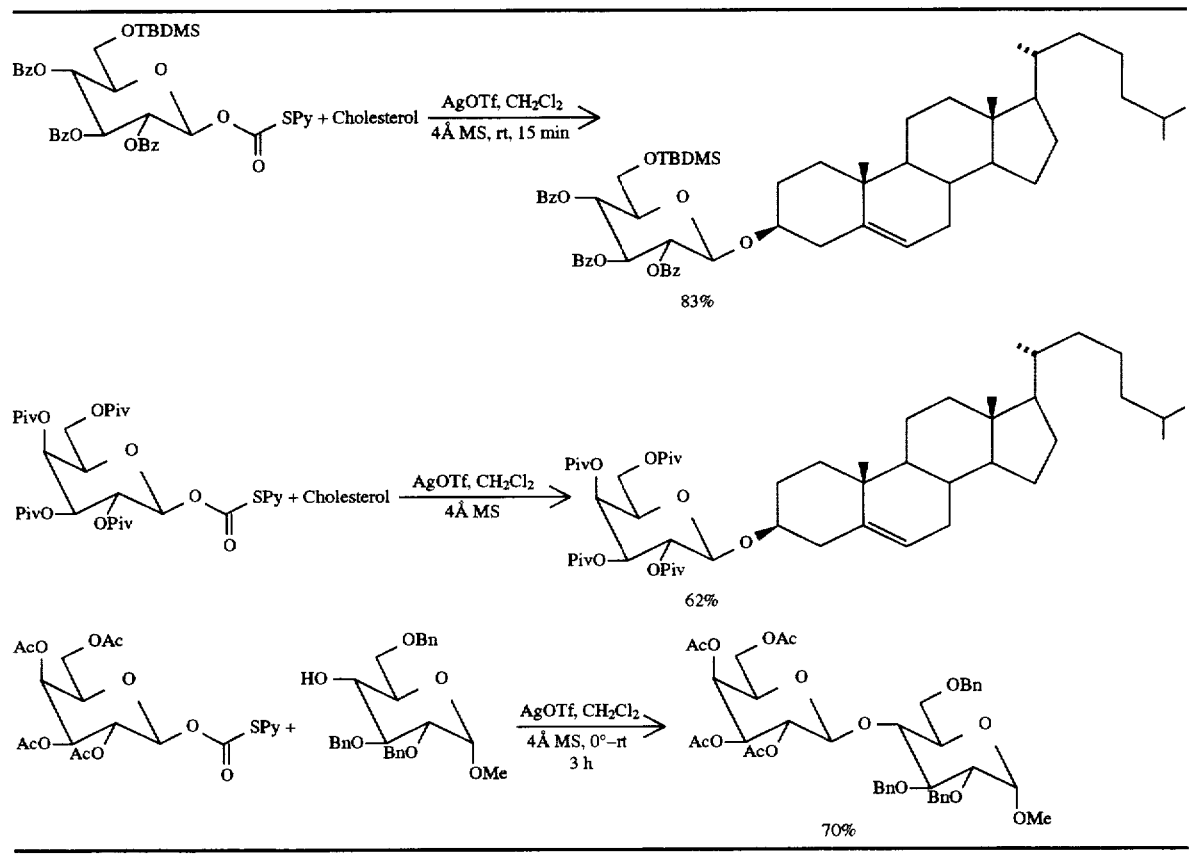

Pursuing the concept further, it was demonstrated that it was possible to couple TOPCAT glycosyl donors, to a variety of MOP glycosyl donors, as acceptors, to produce potential disaccharide MOP donors, with AgOTf promoter, and either $CH_2Cl_2$ or $CH_2Cl_2$-ether, yields from 54 to 74%, with alpha-beta ratios of 3:1 to 11:1, Table XXXI. The products can obviously be utilized both as themselves and as precursors in later syntheses.

TABLE XXXI

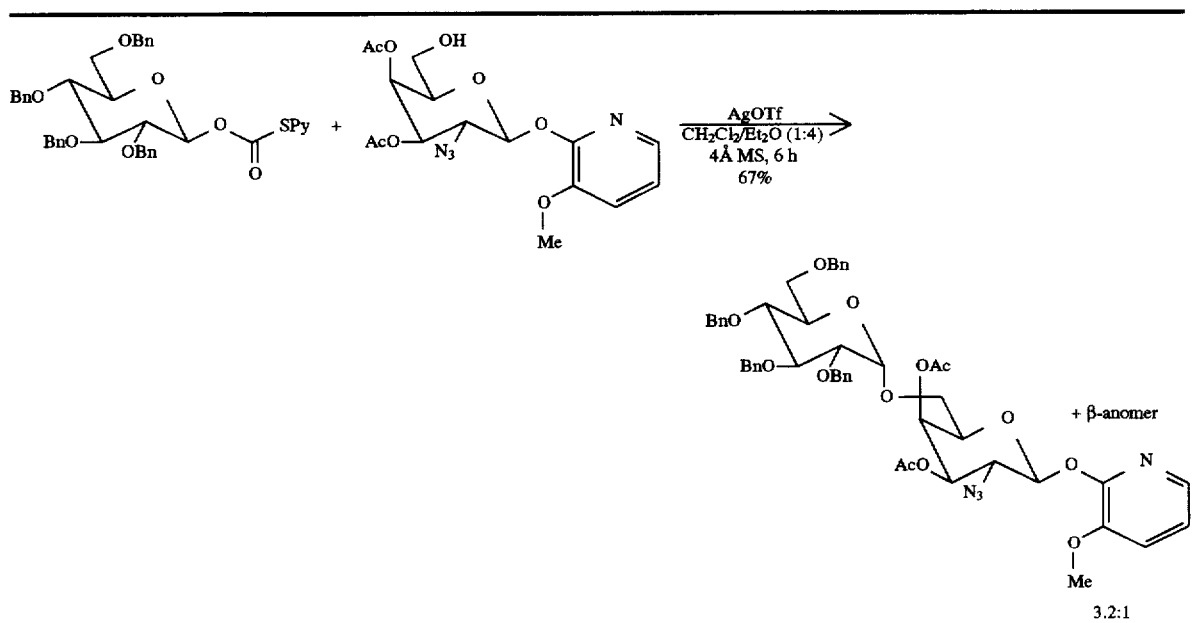

TABLE XXXI-continued
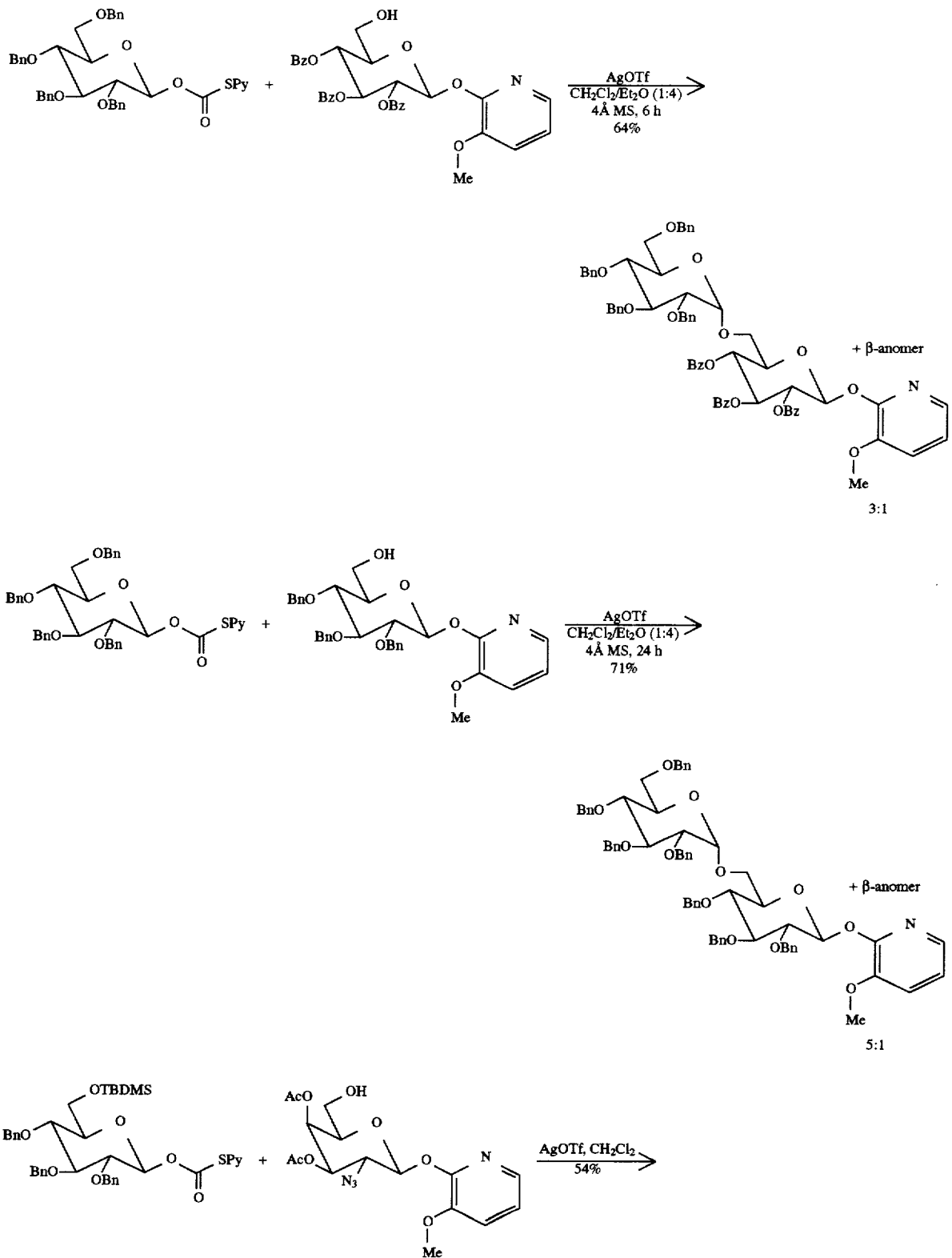

TABLE XXXI-continued
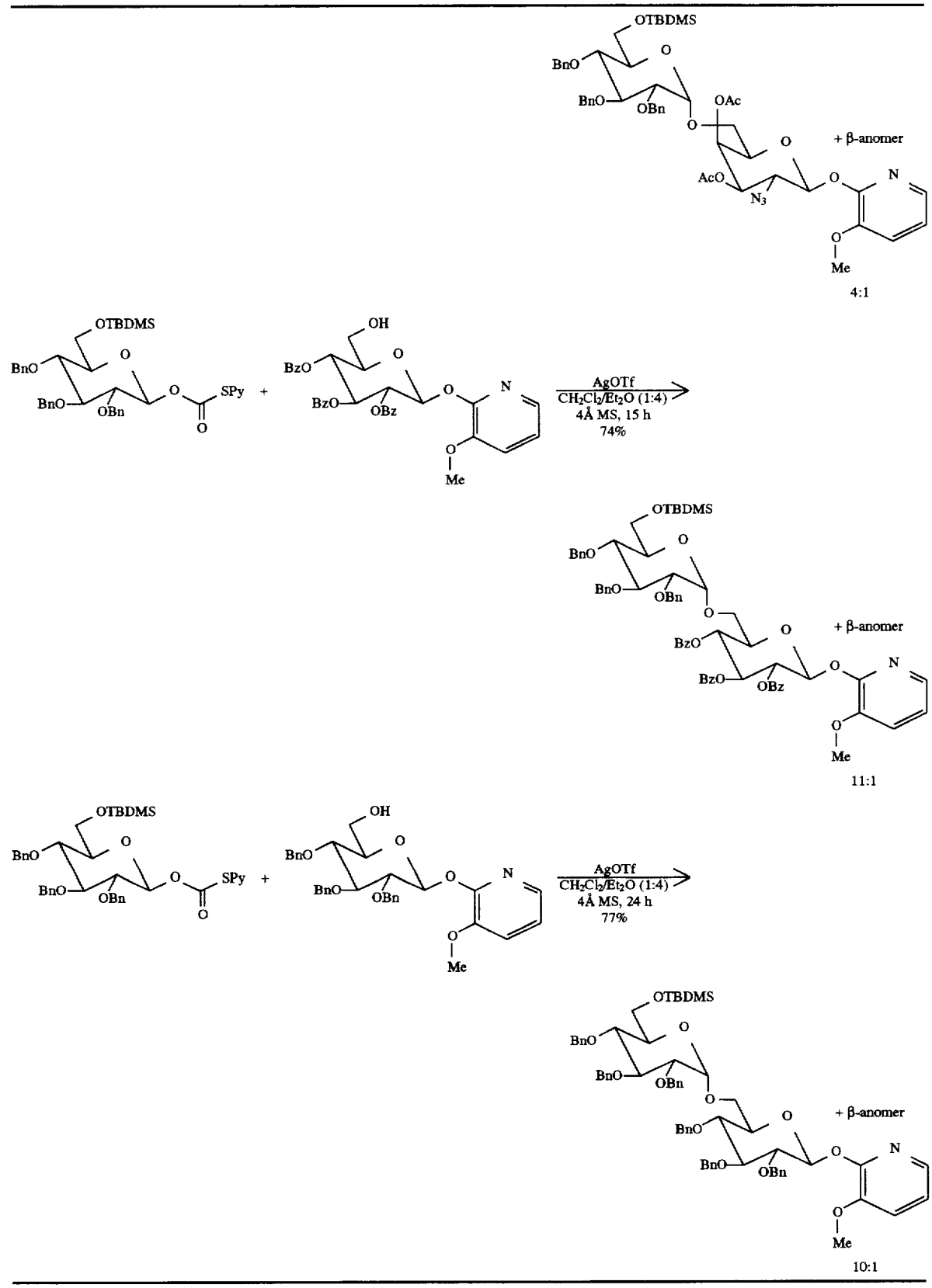

A scheme for such synthetic is indicated, wherein PG means protecting group, showing coupling of TOPCAT donor with MOP acceptor, and further reactions, specific details of oligosaccharides of interest are also shown, Table XXXII.

TABLE XXXII
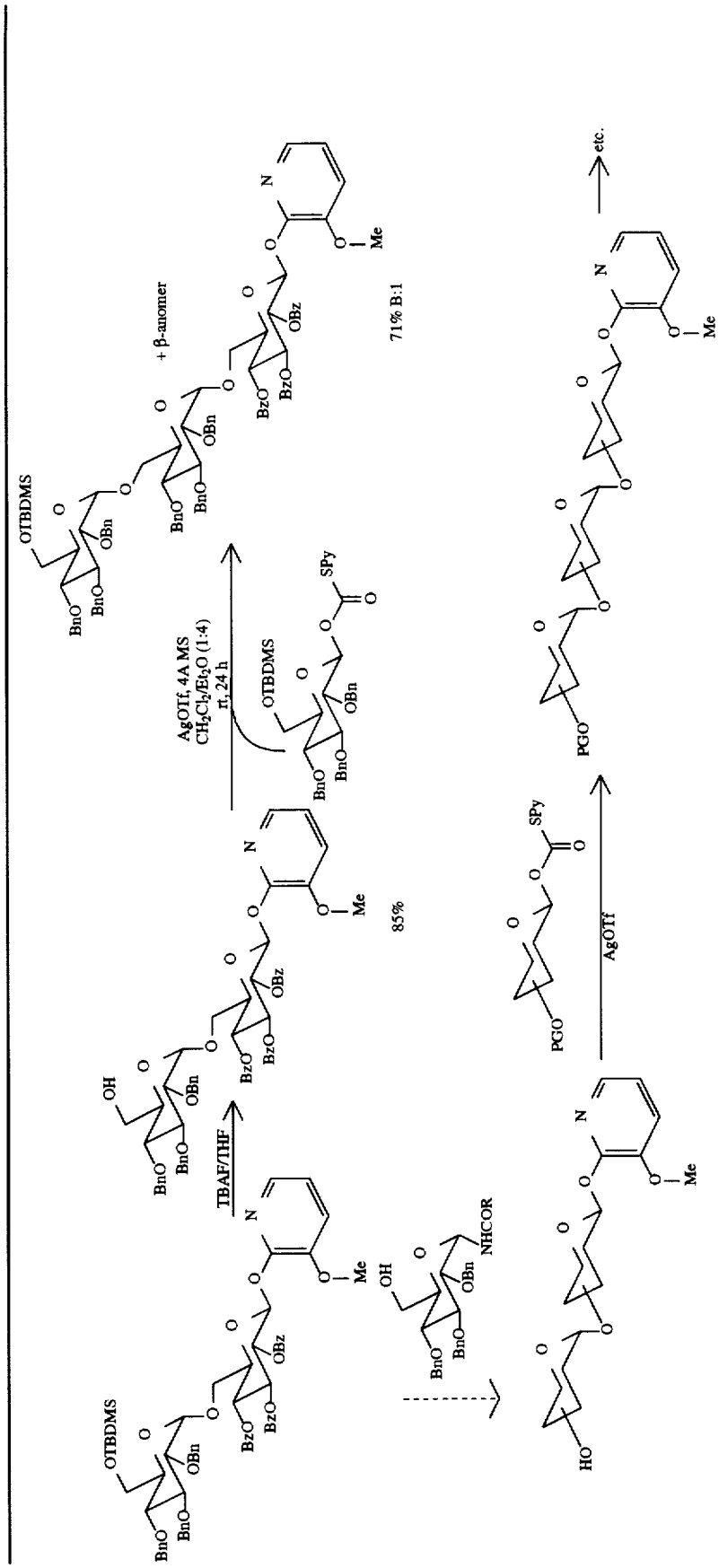

TABLE XXXII-continued
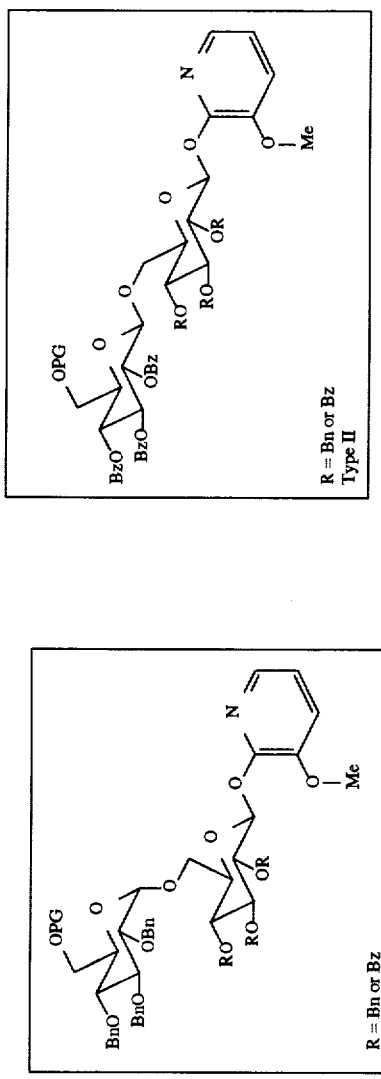
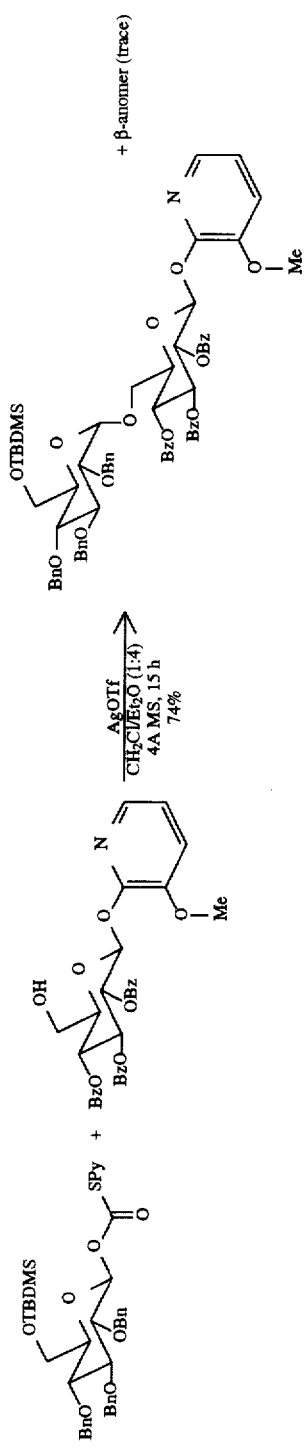

TABLE XXXII-continued
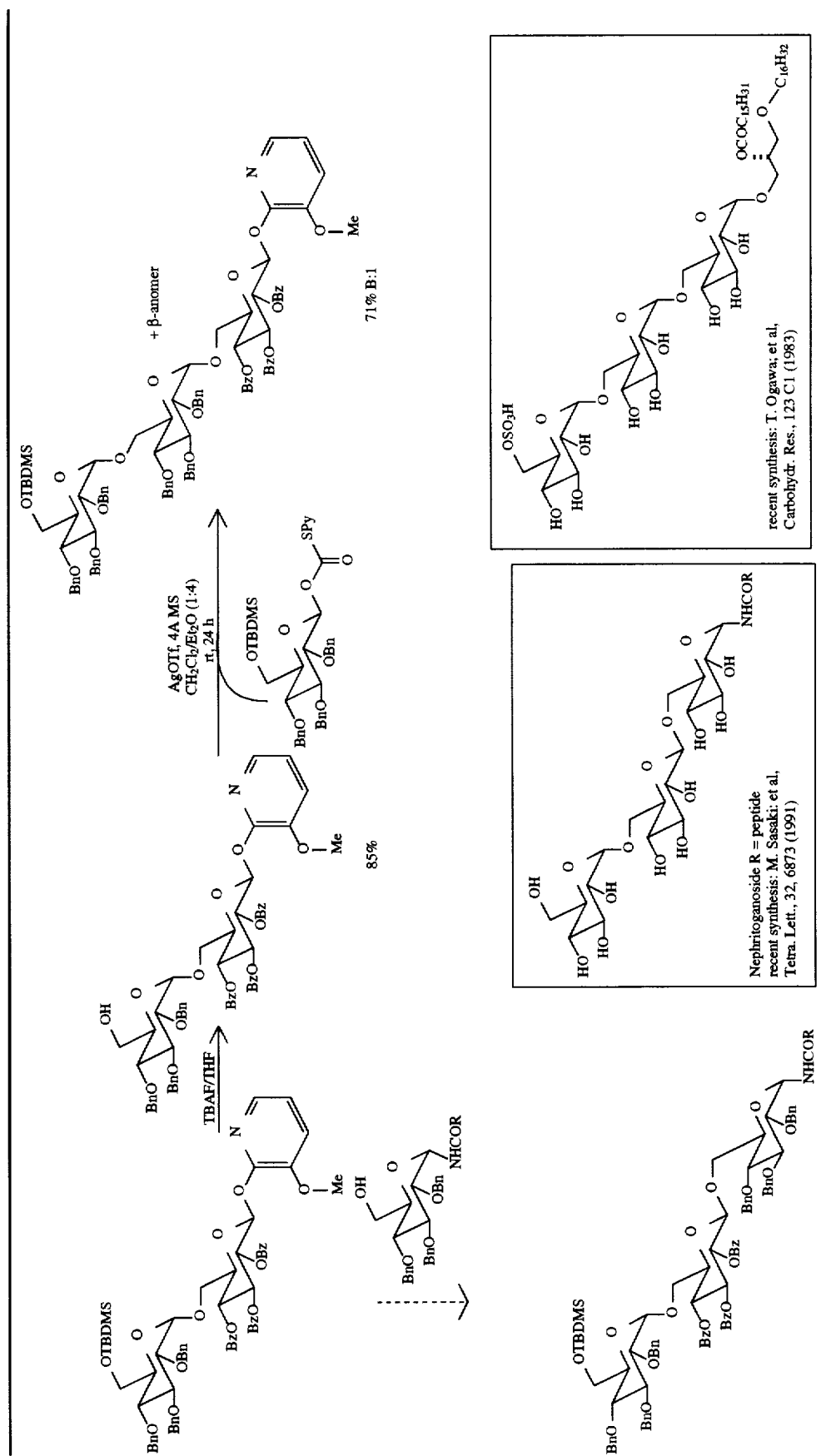

Practical employment of such approaches are shown indicating preparation of $T_N$-antigen type O-serine glycoside using TOPCAT and a related MOP synthesis, preparation of T-antigen type O-serine glycoside via a TOPCAT disaccharide, and a similar but different MOP approach, for comparison the conventional approach is also shown, with its inferior qualitative yield of alpha stereoisomer. Table XXXIII.

TABLE XXXIII

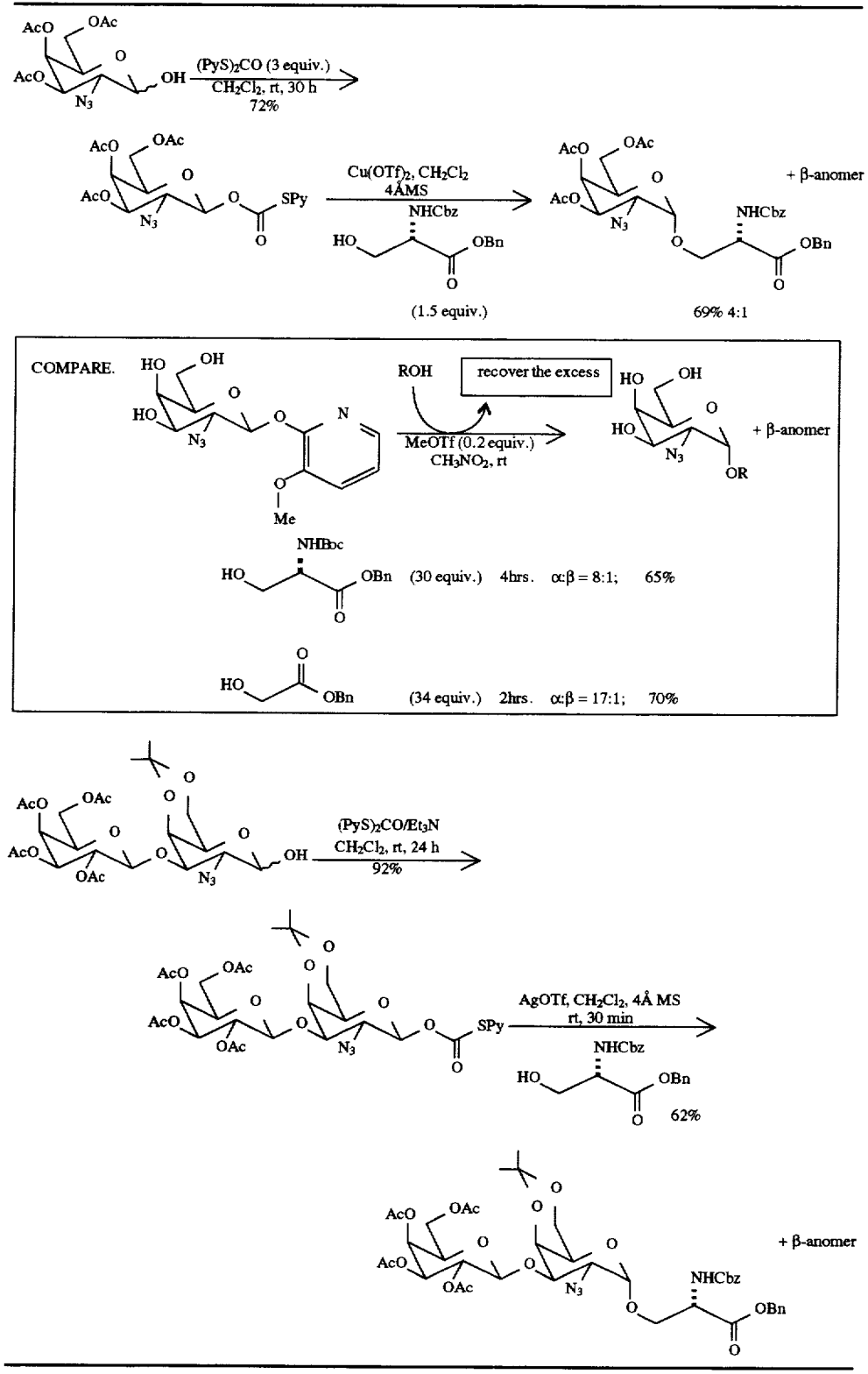

NUCLEOSIDES USING 2-PYRIDYL THIOCARBONATE DONORS

An additional development reacting trimethylsilyl pyrimidine acceptors with TOPCAT pyranosyl donors produces pyranosyl nucleosides, in good yield and alpha:beta ratios of 1:1 or better, Table XXXIV, and with a purine acceptor, Table XXXV. Arabinofuranosyl nucleoside preparation is detailed, Table XXXVI, while ribofuranosyl nucleoside preparation is similarly detailed, Table XXXVII. By inspection those skilled in the art can appreciate that both yields and stereospecificity are more than satisfactory.

TABLE XXXIV

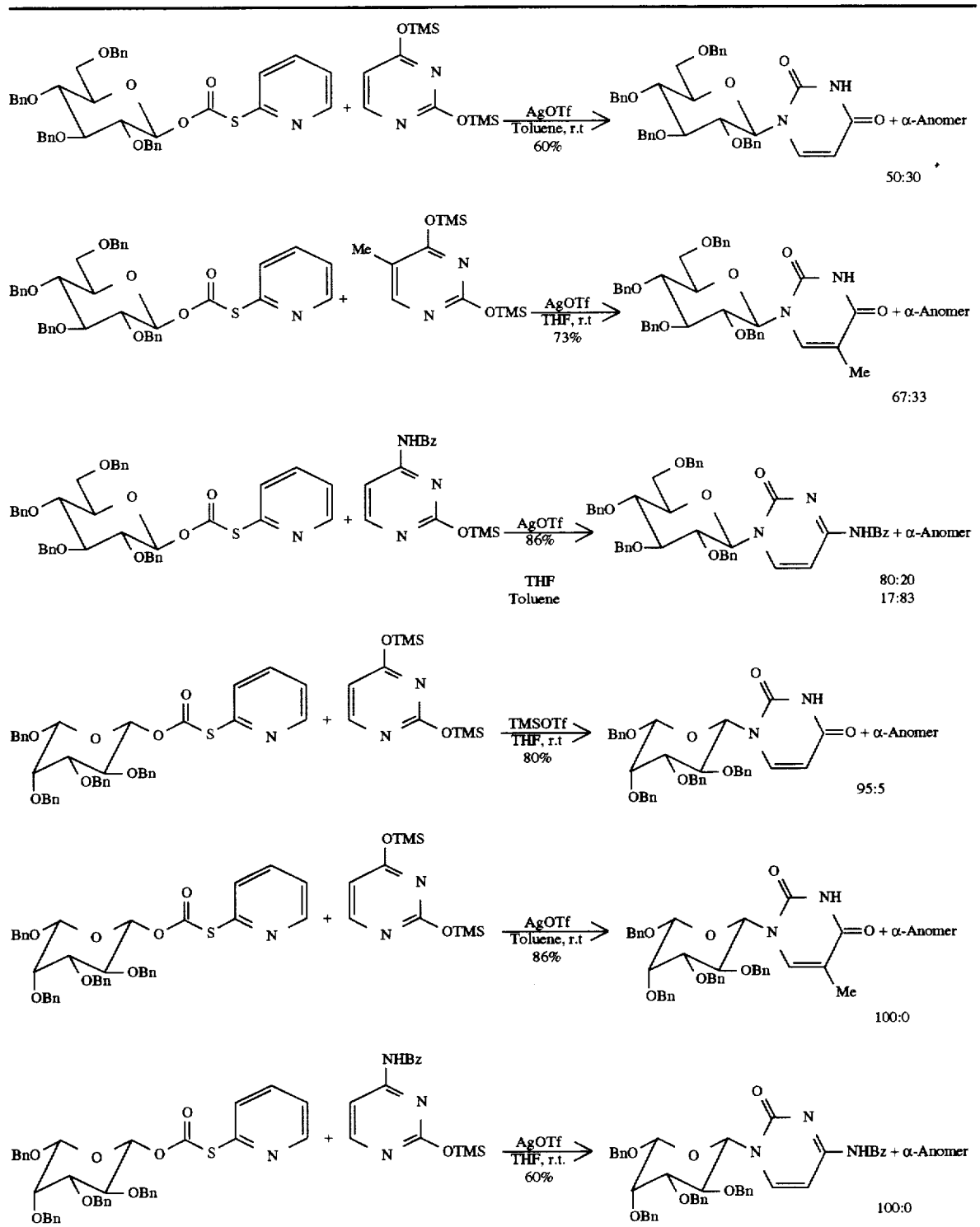

TABLE XXXIV-continued
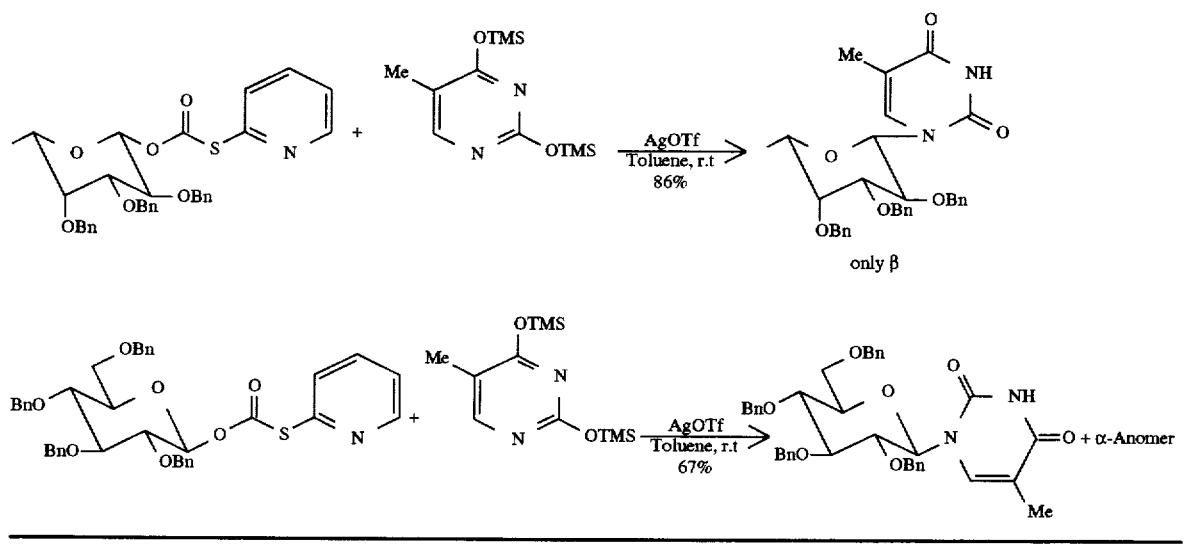
TABLE XXXV
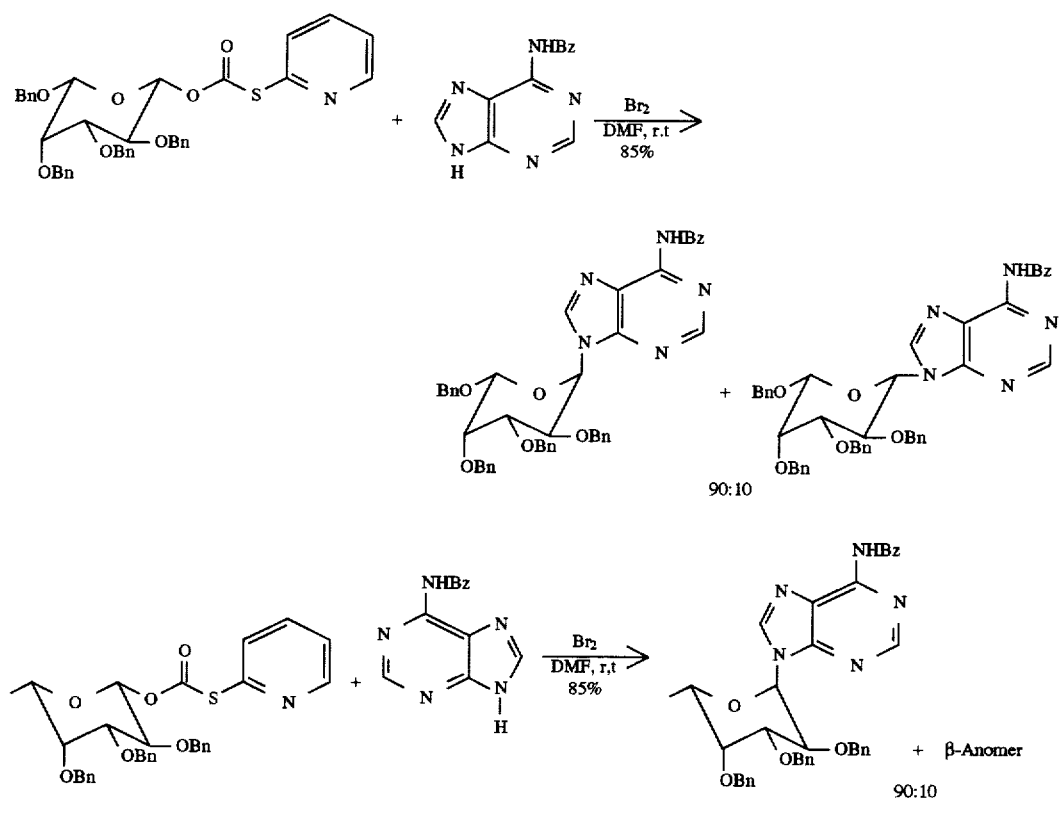

TABLE XXVI
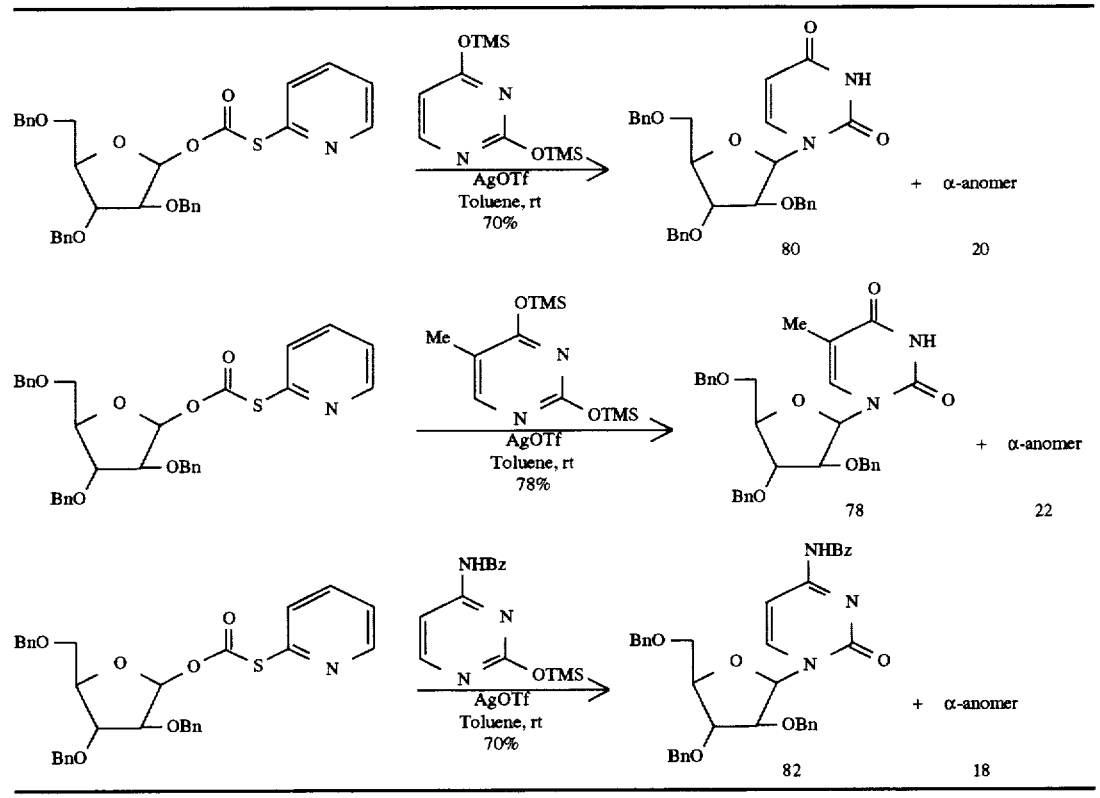
TABLE XXXVII
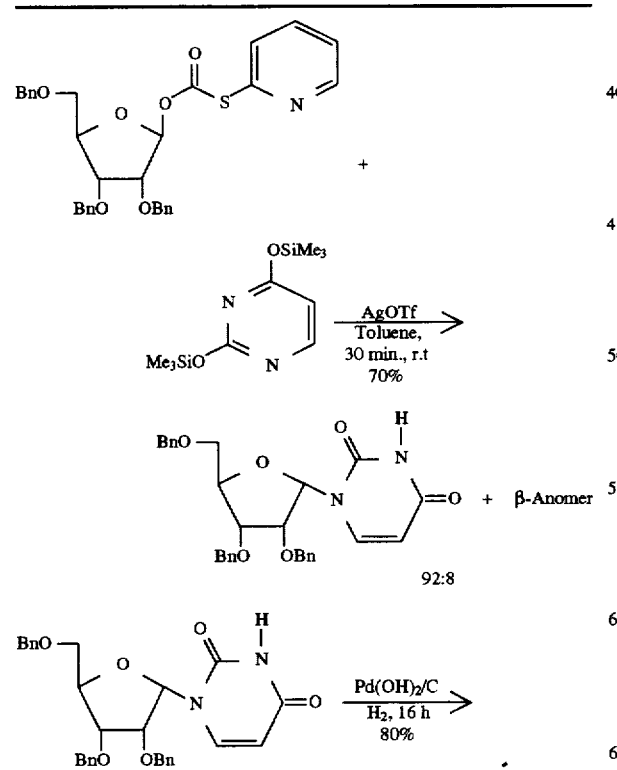
TABLE XXXVII-continued
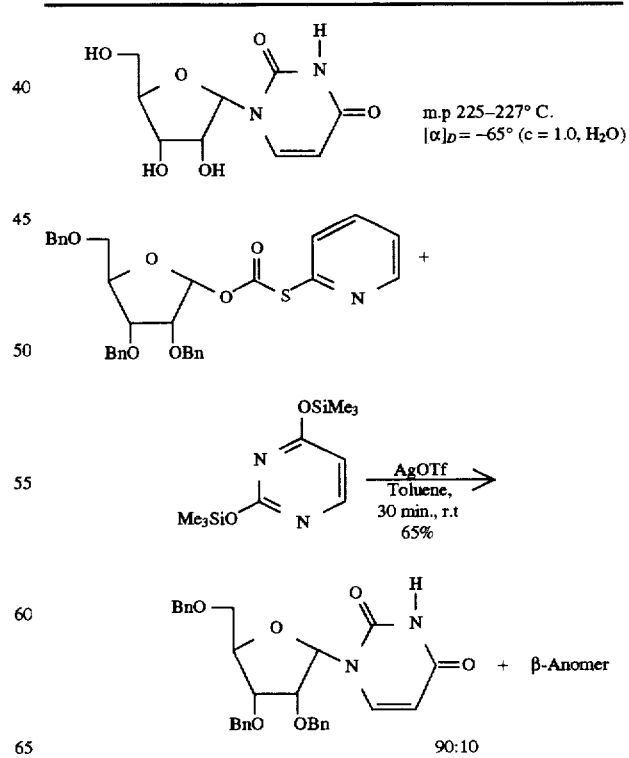

TABLE XXXVII-continued

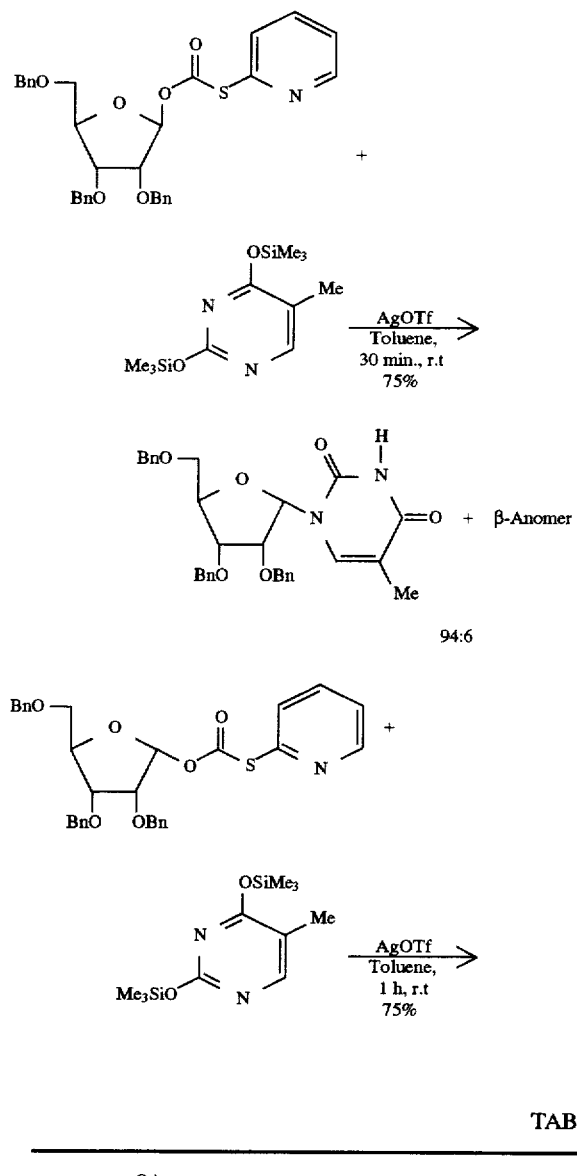

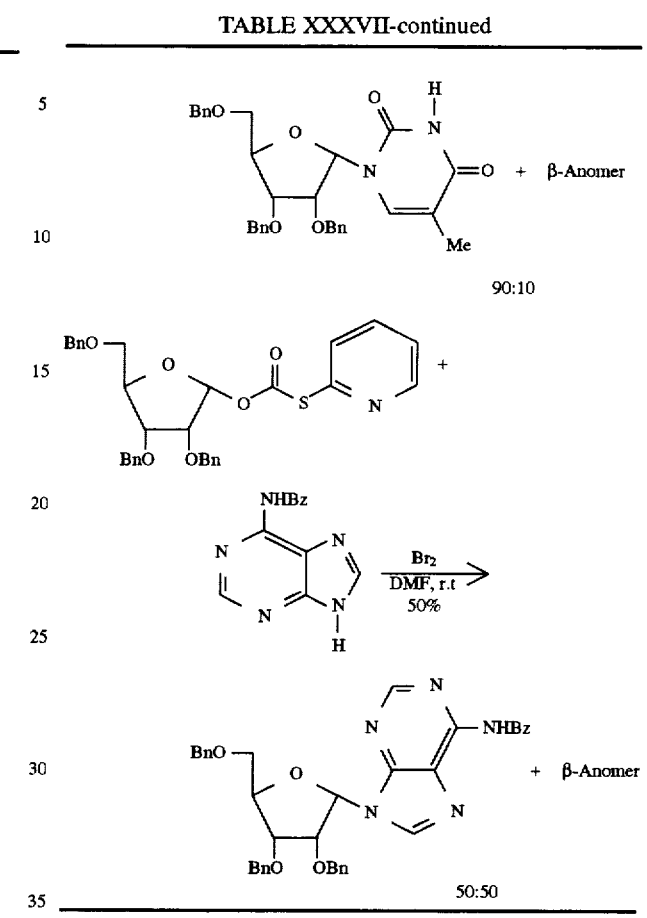

SYNTHESES OF SIALYL LEWIS$^x$ AND LEWIS$^x$

A further demonstration of MOP and TOPCAT versatility and elegance, is shown by the syntheses of Lewis$^x$ structures by MOP, Table XXXVIII, and TOPCAT, Table XXXIX, both showing excellent yield and stereospecificity. Further exploitation of this line of syntheses are shown in Tables XL to XLI, wherein OSE merely indicates the presence of a generic protective silyl moiety.

TABLE XXXVIII

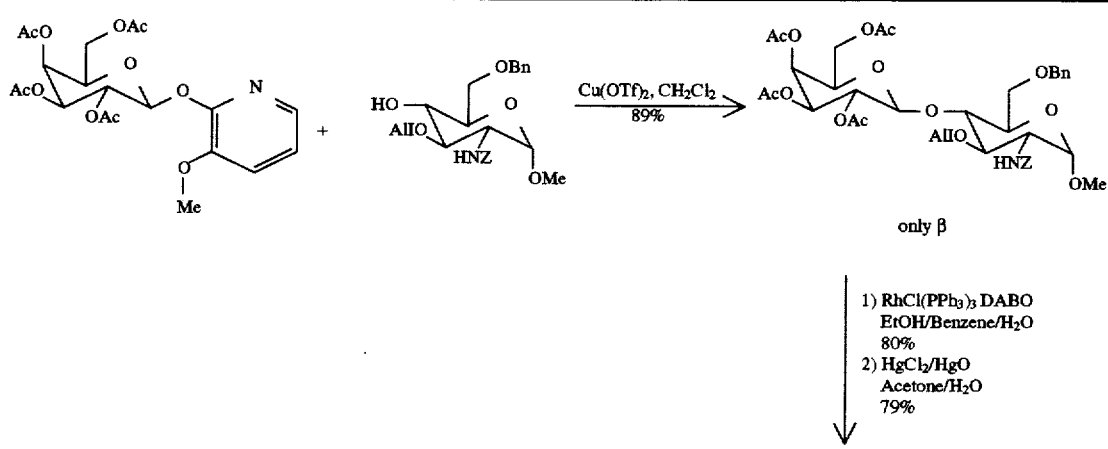

1) RhCl(PPh$_3$)$_3$ DABO
   EtOH/Benzene/H$_2$O
   80%
2) HgCl$_2$/HgO
   Acetone/H$_2$O
   79%

TABLE XXXVIII-continued
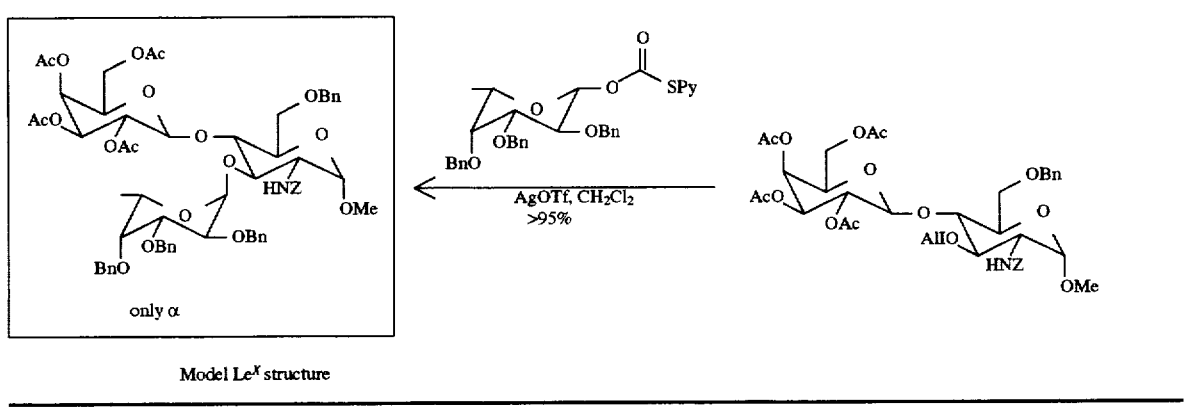
Model Le$^x$ structure
TABLE XXXIX
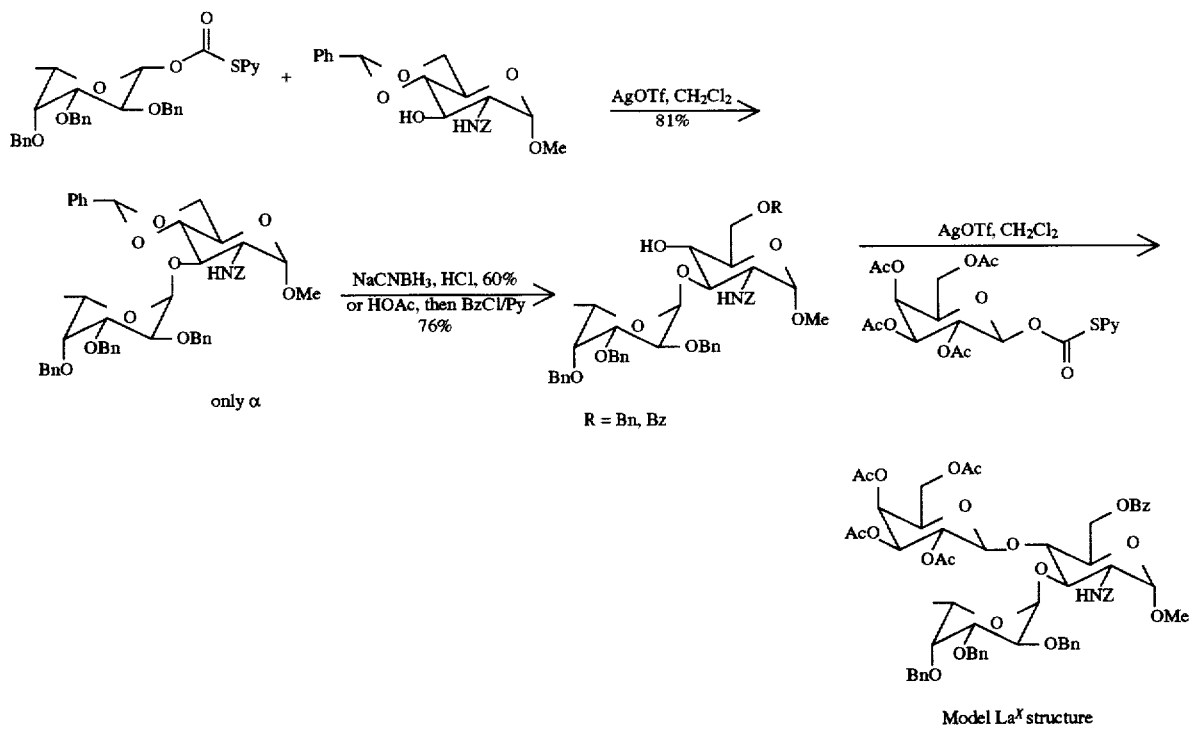
Model La$^x$ structure
TABLE XL
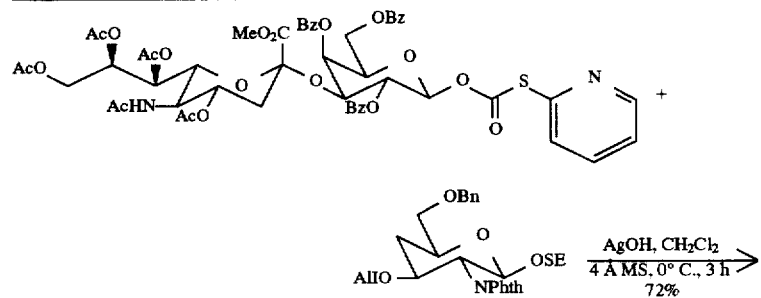

TABLE XL-continued
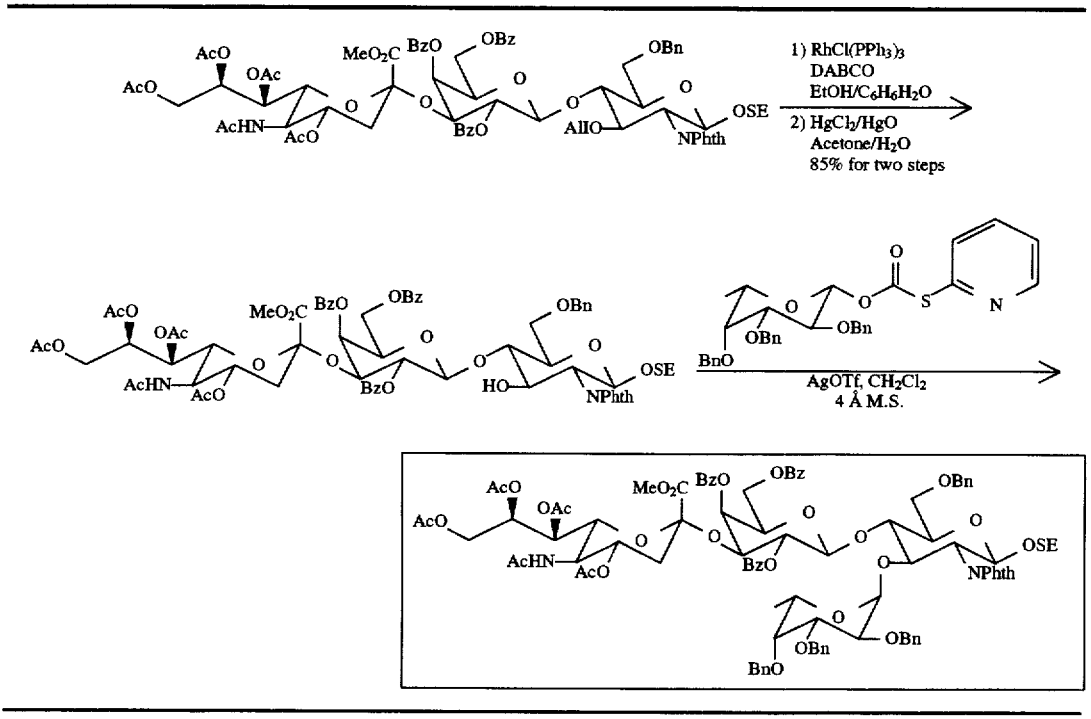
TABLE XLI
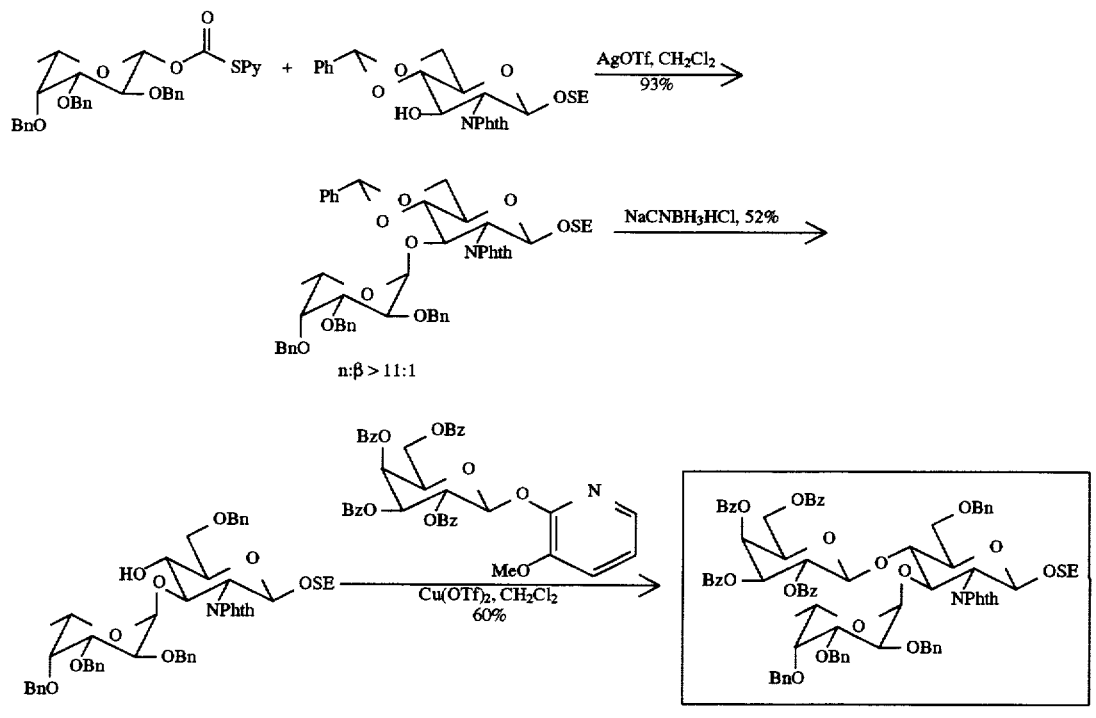

TABLE XLII
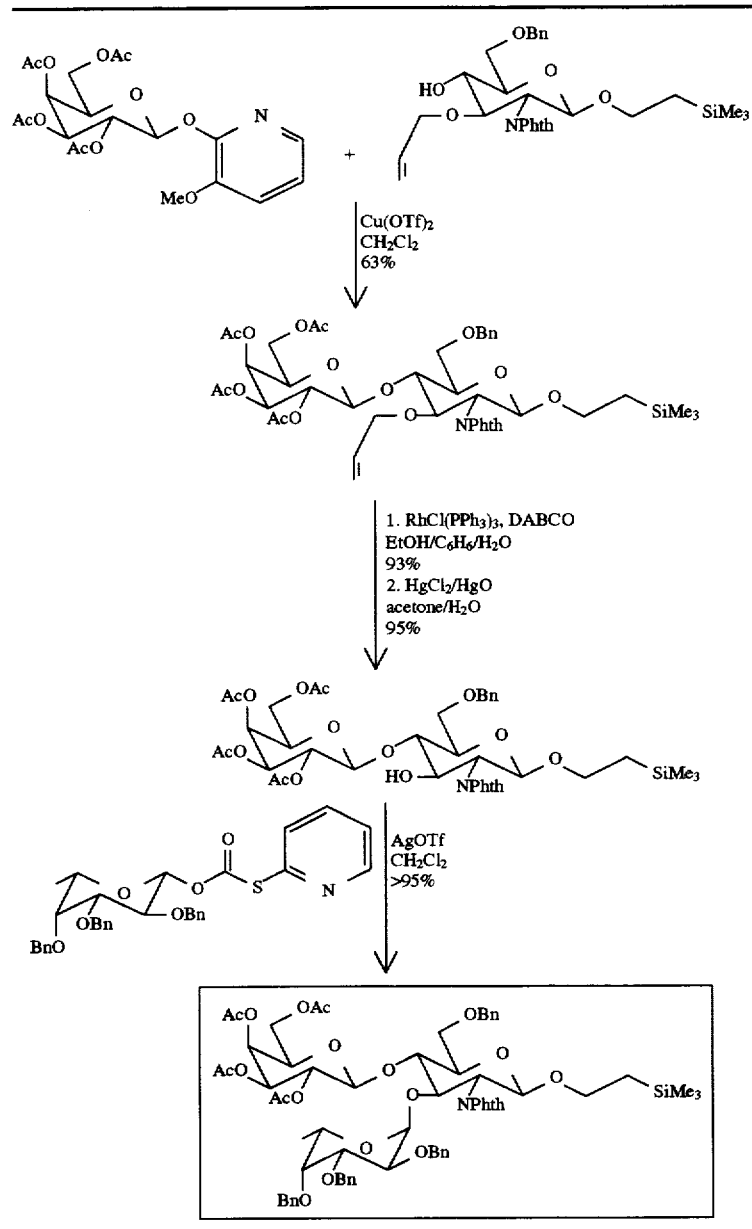
TABLE XLIII
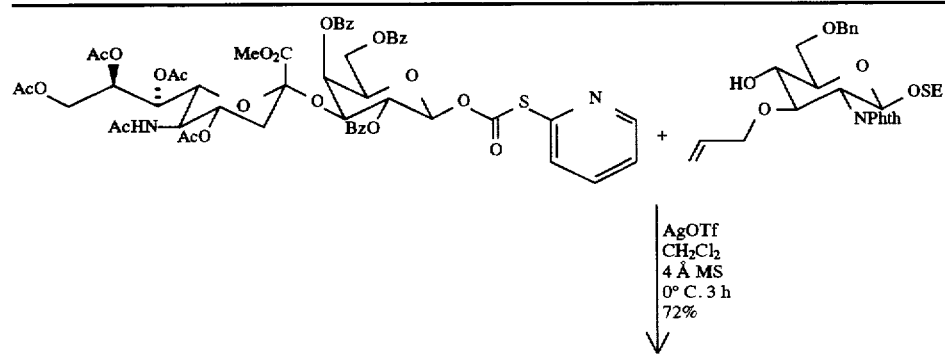

TABLE XLIII-continued

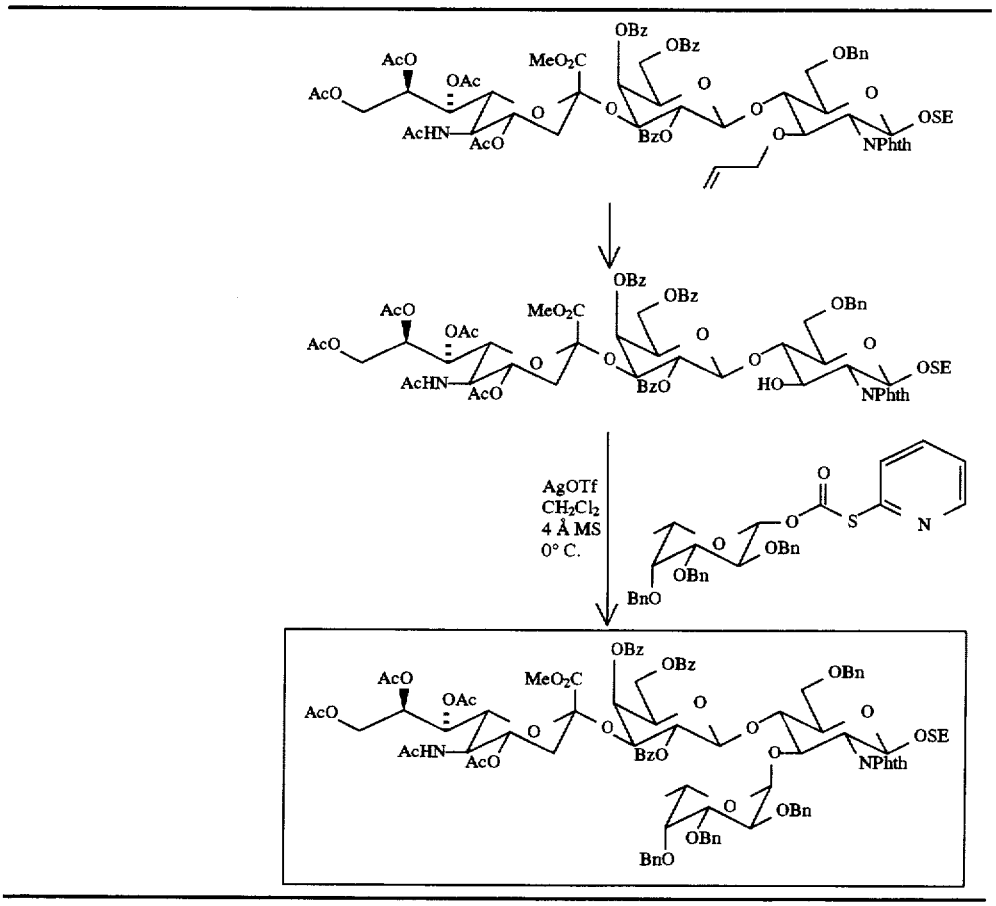

SOLID PHASE ASPECT

In a related development solid phase oligosaccharides can prepared via MOP glycosides. The process involves bonding of a MOP glycoside to a benzyl moiety on a resin support, the fixed glycoside is then allowed to react with an acetylated (inactive) MOP glycoside forming a stereospecific linkage. The acetate is then saponified and the process repeated. Table XLIV. Details of the base strategy, Table XLV. first experiment, Table XLVI, and test recovery of unchanged MOP glycoside, Table XLVII are shown. Test effects using coupled glucopyranosyl MOP donor, $CH_3NO2$/iPrOH acceptor and MeOTf promoter, and changing the solvent are shown in Table XLVIII, yields vary from 40 to 100%, while alpha:beta ratios vary from 7.6 to 5:1. Preparation of a disaccharide using a similar process is shown, Table XLIX. An enhanced coupling procedure using S-pyridyl thioester, is demonstrated, Table L, while preparation of the resin-sugar linking precursor is indicated, Table LI.

TABLE XLIV

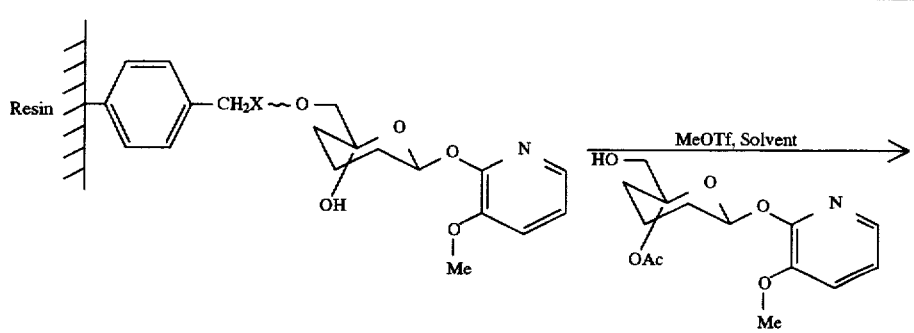

TABLE XLIV-continued
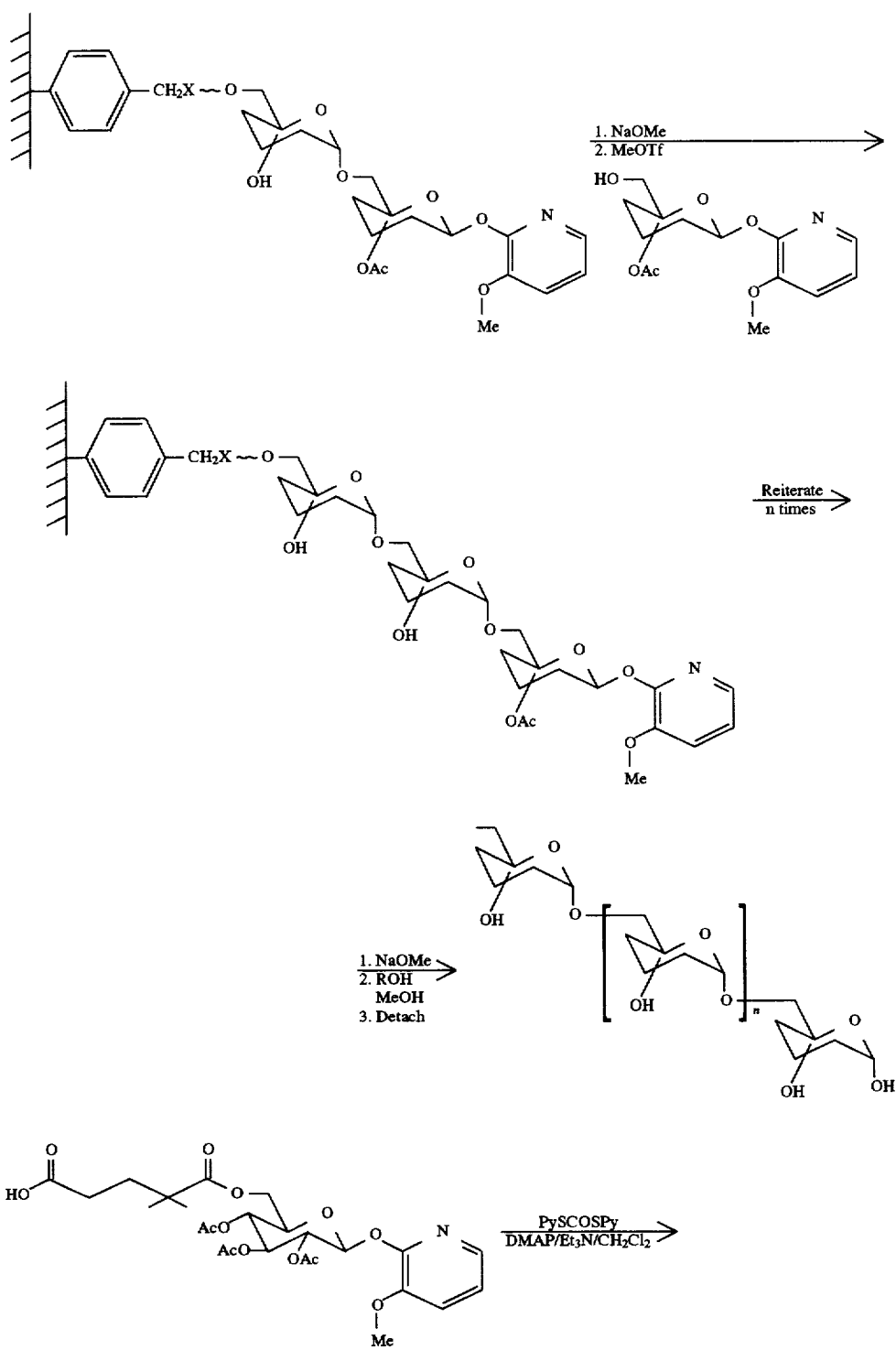

TABLE XLIV-continued

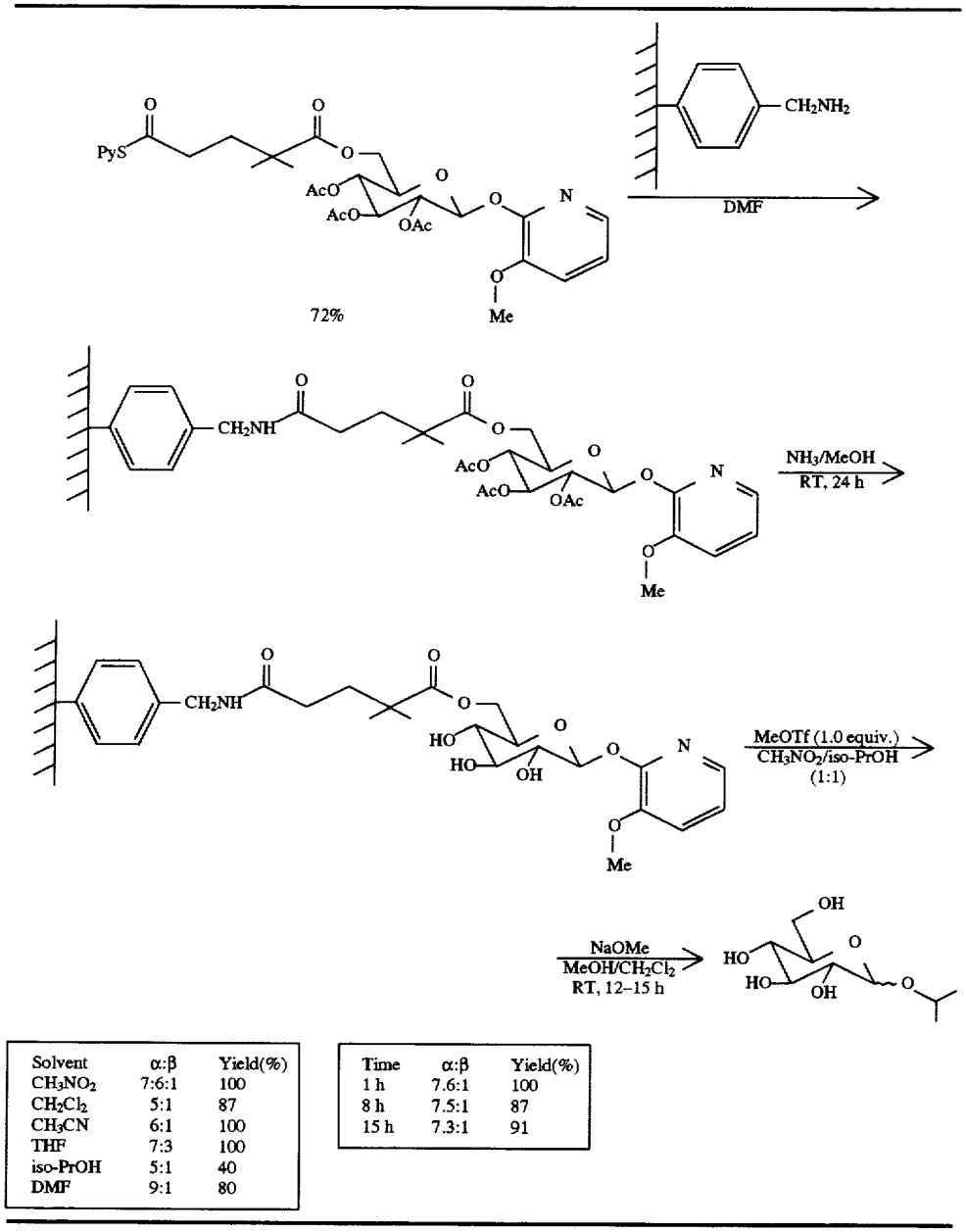

| Solvent | α:β | Yield(%) |
|---|---|---|
| CH₃NO₂ | 7:6:1 | 100 |
| CH₂Cl₂ | 5:1 | 87 |
| CH₃CN | 6:1 | 100 |
| THF | 7:3 | 100 |
| iso-PrOH | 5:1 | 40 |
| DMF | 9:1 | 80 |

| Time | α:β | Yield(%) |
|---|---|---|
| 1 h | 7.6:1 | 100 |
| 8 h | 7.5:1 | 87 |
| 15 h | 7.3:1 | 91 |

(Solid-Phase Oligosaccharides Synthesis)
2,2-dimethyl-4-benzyloxycarbonylbutyric acid To a mixture of 3 g (0.021 mol) of 2,2-dimethylglutaric anhydride, 2.0 ml (0.019 mol) of benzyl alcohol in 10 ml of $CH_2Cl_2$ was added 100 mg of DMAP and 3.4 ml of pyridine. The resulting solution was stired at room temperature for 4 h. After additional 2,2-dimethyl-glutaric acid (0.7 g, 4.9 mmol) was added, the mixture continued to be stirred overnight, then poured into 0.5M $H_2SO_4$ (aq.) solution and extracted with $CH_2Cl_2$. The organic layer was washed with brine, dried over $Na_2SO_4$ and filtered. Concentration followed by purification by flash chromatography on silica gel using EtOAc/hexane (1:1) as the irrigant gave 3.5 g of desired product in 66% yield and 1.2 g of isomer in 23% yield.

$^1$HNMR (CDCl₃): δ=7.37 (s, 5H, Ph), 5.12 (s, 2H, $CH_2$ Ph), 2.42 (t,2H, J=8.1 Hz $CH_2$), 1.94 (t, 2H, J=8.1 Hz, $CH_2$), 1.22 (S, 6H, 2Me).

2,2-dimethyl-4-allylcarbonylbutyric acid

The same procedure described above for the preparation of 2,2-dimethyl-4-benzyloxy-carbonylbutyric acid was followed using allyl alcohol in the place of benzyl alcohol.

$^1$HNMR (CDCl₃): d=5.85–5.98, 5.22–5.36 (m, 3H, olefine-H), 4.58 (dt, 2H, J=1.5 Hz, 6.0 Hz, $CH_2$), 2.39 (m, 2H, $CH_2$), 1.23 (s, 6H, 2Me).

$^{13}$CNMR (CDCl₃): δ=183.38, 172.89, 131.99, 118.25, 65.12, 41.39, 34.68, 29.99, 24.70.

2,2-dimethyl-4-benzyloxycarbonylbutyryl chloride

A mixture of 3.1 g of 2,2-dimethyl-4-benzyloxycarbonylbutyric acid and 3.3 ml of oxalyl chloride was refuxed for 1 h. After being cooled to room temperature, the solution was concentrated in vacuo and dried overnight The obtained oil was not further purified for the next reaction.

2,2-dimethyl-4-allylcarbonylbutyryl chloride

The same procedure described above was followed for the preparation of 2,2dimethyl-4-allylcarbonylbutyryl chloride. 3'-methoxy-2'-pyridyl 2,3,4-tri-O-acetyl-6-O-(2,2-dimethyl-4-benzyloxycarbonylbutyryl)-β-D-glucopyranoside

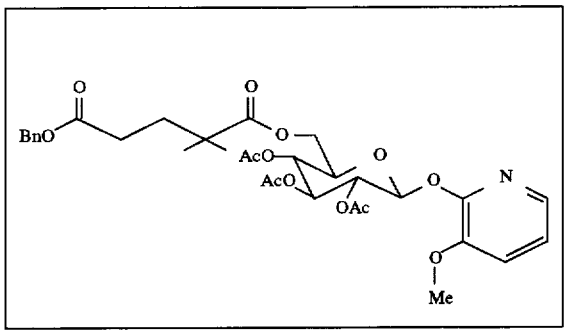

To a solution cooled at 0° C. of 1.0 g (3.48 mmol) of 3'-methoxy-2'-pyridyl-β-D-glucopyranoside in 14 ml of dry pyridine was added dropwise 1.12 g of acyl chloride over 10 min. The resulting mixture was kept at this temperature for 1 h, then additional portion of acyl chloride (0.5 g) was added. After the completion of the reaction (monitored by TLC), acetylation was accomplished by treatment with 1.3 ml of Ac$_2$O for 4 h. The mixture was poured into cold sat. NaHCO$_3$, extracted with CH$_2$Cl$_2$. The organic layer was washed with brine, dried over Na$_2$SO$_4$, filtered and concentrated. The residue was purified by flash chromatography on silica gel column using EtOAc/hexane/CH$_2$Cl$_2$ (1:1:1) to provide 1.4 g of desired product as colourless syrup in 62% yield. [α]$_D$=+20.3° (c 4.93, CHCl$_3$).

$^1$HNMR (CDCl$_3$): δ=7.68 (dd, J$_{5',6}$=4.8 Hz, J4',6'=1.5 Hz, Py-H-6'), 7.34 (m, 5H, Ph), 7.09 (dd, 1H, J$_{4',6}$=1.5 Hz, J$_{4',5}$=7.8 Hz, Py-H-4'), 6.92 (dd, J$_{5',6}$=4.8 Hz, J$_{4',5}$=7.8 Hz, Py-H-5'), 6.21 (d, 1H, J$_{1,2}$=7.8 Hz, H-1), 5.35 (m, 2H, H-4, H-2), 5.13 (t, 1H, J=9.6 Ha, H-3), 5.09 (s, 2H, CH$_2$Ph), 4.18 (br.d, 2H, J=3.9 Hz, 2H-6), 3.92 (m, 1H, H-5), 3.80 (S, 3H, OMe), 2.27 (m, 2H, CH$_2$), 2.03, 2.02, 1.98 (3S, 9H, 3Ac), 1.82–1.89 (m, 2H, CH$_2$), 1.14, 1.13 (2s, 6H, 2Me).

$^{13}$CNMR (CDCl$_3$): δ=176.63, 173.10, 170.17, 169.25, 169.21, 93.41 (C-1)

HRMS (FAB): m/z calc. for C$_{32}$H$_{40}$NO$_{13}$ (M+H$^+$) 646.2499, found 646.2481.

3'-methoxy-2'-pyridyl 2,3,4-tri-O-acetyl-6-O-(2,2-dimethyl-4-benzyloxycarbonybutyryl)-β-D-galactopyranoside The same procedure described above was followed in 56% yield. [α]$_D$=+17.4° (c 3.0, CHCl$_3$).

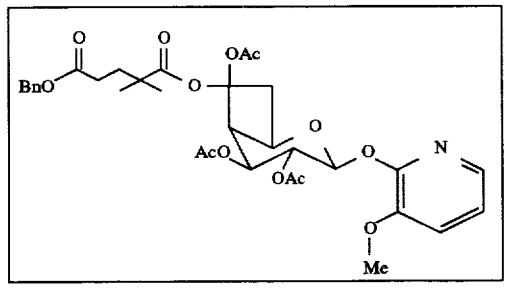

$^1$HNMR (CDCl$_3$): δ=7.67 (dd, 1H, J$_{5',6}$=4.8 Hz, J$_{4',6}$=1.5 Hz, Py-H-6'), 7.34 (br.S, 5H, Ph), 7.08 (dd, 1H, J$_{4',6}$=1.5 Hz, J$_{4',5}$=7.8 Hz, Py-H-4'), 6.91 (dd, 1H, J$_{5',6}$=4.8 Hz, J$_{4',5}$=7.8 Hz, Py-H-5'), 6.20 (d, 1H, J$_{1,2}$=8.4 Hz, H-1), 5.57 (dd, 1H, J$_{1,2}$=8.4 Hz, J$_{2,3}$=10.3 Hz, H-2), 5.43 (d, 1H, J$_{3,4}$=3.3 Hz, H-4), 5.17 (dd, 1H, J$_{3,4}$=3.3 Hz, J$_{2,3}$=10.3 Hz, H-3), 5.08 (S, 2H, CH$_2$Ph), 4.13 (m, 3H, H-5, 2H-6), 3.80 (s, 3H, OMe), 2.29 (m, 2H, CH$_2$), 2.12, 1.99, 1.97 (3s, 9H, 3Ac), 1.85 (m, 2H, CH$_2$), 1.11 (2s, 6H, 2Me).

$^{13}$CNMR (CDCl$_3$): δ=176.28, 172.89, 169.98, 169.87, 169.21, 93.68 (C-1).

HRMS (FAB): m/z calc. for C$_{32}$H$_{40}$NO$_{13}$ (M+H$^+$) 646.2499, found 646.2467.

3'-methoxy-2'-pyridyl 3,4-di-O-acetyl-6-O-(2,2-dimethyl-4-allyloxycarbonylbutyryl)-2-azido-2-deoxy-β-D-galactopyranoside The same procedure described above was followed in 87% yield. [α]$_D$=+13.0° (c 0.43, CHCl$_3$).

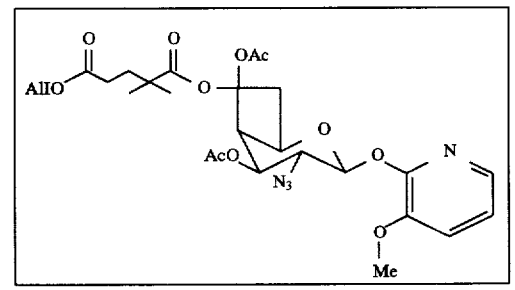

$^1$HNMR (CDCl$_3$): δ=7.67 (m, 1H, Py-H-6'), 7.12 (dd, 1H, J$_{4',6}$=1.5 Hz, J$_{4',5}$=7.8 Hz, Py-H-4'), 6.95 (dd, J$_{5',6}$=4.8 Hz, J$_{4',5}$=7.8 Hz, Py-H-5'), 6.08 (d, 1H, J$_{1,2}$=8.4 Hz, H-1), 5.88 (m, 1H, olefine-H), 5.38 (d, 1H, J$_{3,4}$=3.3 Hz, H-4), 5.19–5.32 (m, 2H, olefine-H), 4.98 (dd, 1H, J$_{3,4}$=3.3 Hz, J$_{2,3}$=10.5 Hz, H-3), 4.53 (m, 2H, CH$_2$), 4.10 (m, 4H, H-2, H-5, 2H-6), 3.86 (s, 3H, OMe), 2.20 (m, 2H, CH$_2$), 2.13, 2.06 (2s, 6H, 2Ac), 1.82 (m, 2H, CH$_2$), 1.11 (s, 6H, 2Me).

$^{13}$CNMR (CDCl$_3$): δ=176.29, 172.71, 169.80, 169.53, 94.36 (C-1).

debenylation of 3'-methoxy-2'-pyridyl 2,3,4-tri-O-acetyl-6-O-(2,2-dimethyl-4-benzyloxy-carbonylbutyryl)-β-D-glucopyranoside

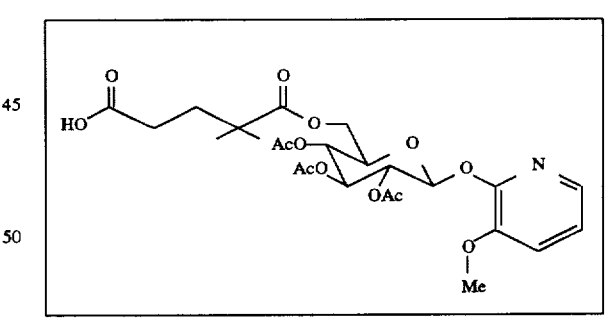

A mixture of 1.2 g of 3'-methoxy-2'-pyridyl 2,3,4-tri-O-acetyl-6-O-(2,2-dimethyl-4-benzyloxy-carbonylbutyryl)-β-D-glucopyranoside, 54 mg of 20% Pd(OH)$_2$/C and 10 ml of EtOAc was stirred under hydrogen for 3 h. After removal of catalyst by filtration over celite, concentration gave the desired product as a white solid in quantitative yield. mp., 45° C., [α]$_D$=+10.1° (c 2.4, CHCl$_3$).

$^1$HNMR (CDCl$_3$): δ=7.70 (dd, J$_{5',6}$=4.8 Hz, J4',6'=1.5 Hz, Py-H-6'), 7.12 (dd, 1H, J$_{4',6}$=1.5 Hz, J$_{4',5}$=7.8 Hz, Py-H-4'), 6.95 (dd, J$_{5',5}$=4.8 Hz, J$_{4',5}$=7.8 Ha, Py-H-5'), 6.17 (d, 1H, J$_{1,2}$=8.1 Hz, H-1), 5.35 (m, 2H, H-4, H-2), 5.14 (t, 1H, J=9.9 Hz, H-3), 4.22 (dd, 1H, J$_{5,6a}$=2.4 Hz, J$_{6a,6b}$=12.3 Hz, H-6a), 4.15 (dd, 1H, $J_{5,6b}$=4.8 Hz, $J_{6a,6b}$=12.3 Hz, H-6b), 3.95 (m, 1H, H-5), 3.82 (s, 3H, OMe), 2.27 (t, 2H, J=8.1 Hz, $CH_2$), 2.05, 2.02, 1.97 (3s, 9H, 3Ac), 1.87 (m, 2H, $CH_2$), 1.15, 1.14 (2s, 6H, 2Me).

$^{13}$CNMR ($CDCl_3$): δ=177.95, 176.58, 170.18, 169.36, 169.23, 151.53, 144.22, 136.63, 119.05, 93.59 (C-1).

IR Umax: 1755 $cm^{-1}$

HRMS (FAB): m/z calc. for $C_{25}H_{34}NO_{13}$ ($M+H^+$) 557.2030, found 557.2071.

debenylation of 3'-methoxy-2'-pyridyl 2,3,4-tri-O-acetyl-6-O-(2,2-dimethyl-4-benzyloxy-carbonylbutyryl)-β-D-galactopyranoside

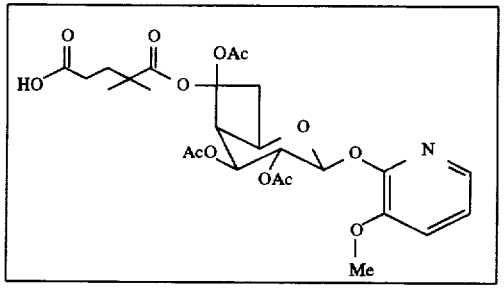

The same procedure described above was followed in quantitative yield. mp., 45° C.; $[α]_D$=+17.9° (c 2.0, $CHCl_3$).

$^1$HNMR ($CDCl_3$): δ=7.71 (dd, 1H, $J_{5',6}$=4.8 Hz, $J_{4',6}$=1.5 Hz, Py-H-6'), 7.12 (dd, 1H, $J_{4',6}$=1.5 Hz, $J_{4',5}$=7.8 Hz, Py-H-4'), 6.95 (dd, 1H, $J_{5',6}$=4.8 Hz, $J_{4',5}$=7.8 Hz, Py-H-5'), 6.15 (d, 1H, $J_{1,2}$=8.1 Hz, H-1), 5.57 (dd, 1H, $J_{1,2}$=8.1 Hz, $J_{2,3}$=10.2 Hz, H-2), 5.45 (br.d, 1H, $J_{3,4}$=3.3 Hz, H-4), 5.18 (dd, 1H, $J_{3,4}$=3.3 Hz, $J_{2,3}$=10.2 Hz, H-3), 4.19 (m, 3H, H-5, 2H-6), 3.83 (s, 3H, OMe), 2.27 (m, 2H, $CH_2$), 2.15, 2.00, 1.97 (3s, 9H, 3Ac), 1.84 (m, 2H, $CH_2$), 1.13 (s, 6H, 2Me).

$^{13}$CNMR ($CDCl_3$): δ=177.83, 176.38, 170.17, 170.05, 169.29, 151.59, 144.19, 136.50,n 119.29, 118.95, 94.01 (C-1).

HRMS (FAB): m/z calc. for $C_{25}H_{34}NO_{13}$ ($M+H^+$) 556.2030, found 556.2070.

deallylation of 3'-methoxy-2'-pyridyl 2,3-di-O-acetyl-6-O-(2,3-dimethyl-4-allyloxycarbonylbutyryl)-2-azido-2-deoxy-β-D-galactopyranoside

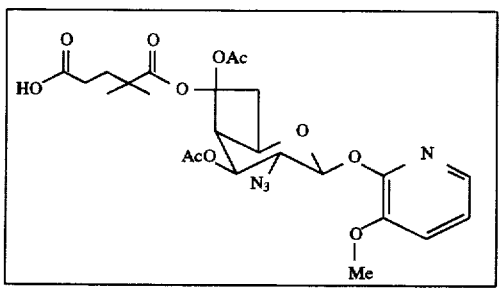

To a solution of 375 mg (0.65 mmol) 3'-methoxy-2'-pyridyl 2,3-di-O-acetyl-6-O-(2,2-dimethyl-4-allyloxycarbonylbutyryl)-2-azido-2-deoxy-β-D-galactopyranoside in 1.5 ml of dry THF was added 75 mg (0.065 mmol) of $Pd(PPh_3)_4$ and 108 μl (1.3 mmol) pyrolidine at room temperature under argon. The resulting mixture was stirred for 15 min, then concentrated in vacuo. The residue was purified by flash chomatogrphy on silica gel column using EtOAc/hexane (1:1) to $CHCl_3$/MeOH (20:1) to provide 250 mg of acid in 72% yield. $[α]_D$=−9.6° (c, 0.56, $CHCl_3$).

$^1$HNMR ($CDCl_3$): δ=7.72 (dd, 1H, $J_{5',6}$=4.8 Hz, $J_{4',6}$=1.5 Hz, Py-H-6'), 7.16 (dd, 1H, $J_{4',6}$=1.5 Hz, $J_{4',5}$=7.8 Hz, Py-H-4'), 6.98 (dd, $J_{5',6}$=4.8 Hz, $J_{4',5}$=7.8 Hz, Py-H-5'), 6.04 (d, 1H, $J_{1,2}$=8.4 Hz, H-1), 5.41 (d, 1H, $J_{3,4}$=3.3 Hz, H-4), 4.99 (dd, 1H, $J_{3,4}$=3.3 Hz, $J_{2,3}$=10.8 Hz, H-3), 4.08–4.17 (m, 4H, H-2, H-5, 2H-6), 3.88 (s, 3H, Ome), 2.28 (m, 2H, $CH_2$), 2.16, 2.08 (2s, 6H, 2Ac), 1.85 (m, 2H, $CH_2$), 1.14 (s, 6H, 2Me).

$^{13}$CNMR ($CDCl_3$): δ=94.67 (C-1)

3'-methoxy-2'-pyridyl 2,3,4-tri-O-acetyl-6-O-(2,2-dimethyl-4-thiopyridyl-carbonylbutyryl)-β-D-glucopyranoside

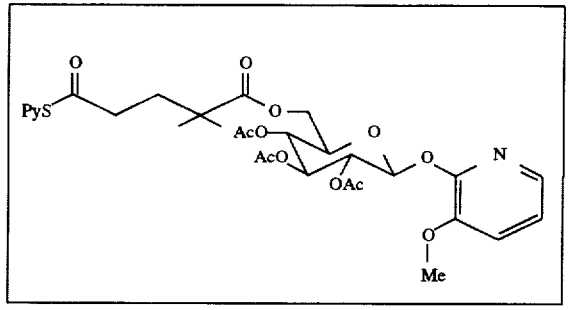

A mixture of 986 mg (1.78 mmol of acid precursor, 530 mg (2.14 mmol) of di(S-2-pyridyl)thiocarbonate, 298 μl (2.14 mmol) of $Et_3N$, 43 mg (0.36 mmol) of DMAP and 10 ml of dry $CH_2Cl_2$ was stirred at room temperature for 24 h. Concentration followed by flash chromatogrphy on silica gel column using $CH_2Cl_2$/EtOAc/hexane (1:2:1) gave the desired product as a yellow solid (850 mg, 72%). mp., 47°–48° C.; $[α]_D$=13.2° (c, 1.57, $CHCl_3$).

$^1$HNMR ($CDCl_3$): δ=8.61 (m, 1H, SPy-H-6"), 7.59–7.74 (m, 3H, 2SPy-H, Py-H-6'), 7.29 (m, 1H, SPy-H), 7.10 (br.d, 1H, J=6.6 Hz, Py-H-4'), 6.93 (dd, 1H, $J_{5',6}$=4.8 Hz, $J_{4',5}$=8.1 Hz, Py-H-5'), 6.24 (d, 1H, $J_{1,2}$=7.5 Hz, H-1), 5.37 (m, 2H, H-2, H-4), 5.15 (t, 1H, J=9.0 Hz, H-3), 4.20 (m, 2H, 2H-6), 3.96 (m, 1H, H-5), 3.81 (s, 3H, OMe), 2.64 (t, 2H, J=7.5, $CH_2$), 2.06, 2.04, 1.99 (3s, 9H, 3Ac), 1.72 (m, 2H, $CH_2$), 1.16 (s, 6H, 2Me).

3'-methoxy-2'-pyridyl 2,3,4-tri-O-acetyl-6-O-(2,2-dimethyl-4-thiopyridyl-carbonylbutyryl)-β-D-galactopyranoside

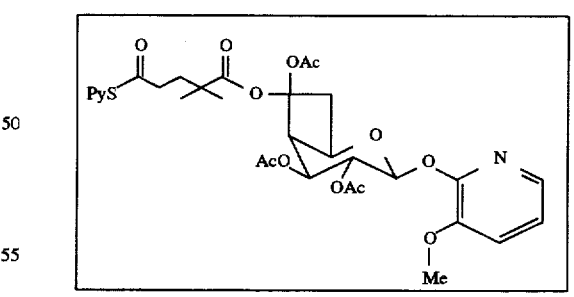

The same procedure described above was followed. 68% yield, mp., 50°–52° C.; $[α]_D$=+20.8° (c 2.36, $CHCl_3$).

$^1$HNMR ($CDCl_3$): δ=8.61 (m, 1H, SPy-H-6"), 7.57–7.76 (m, 3H, 2SPy-H, Py-H-6'), 7.27 (m, 1H, SPy-H), 7.10 (dd, 1H, $J_{4',6}$=1.5 Hz, $J_{4',5}$=7.8 Hz, Py-H-4'), 6.92 (dd, 1H, $J_{5',6}$=4.8 Hz, $J_{4',5}$=7.8 Hz, Py-H-5'), 6.23 (d, 1H, $J_{1,2}$=8.1 Hz, H-1), 5.58 (dd, 1H, $J_{1,2}$=8.1 Hz, $J_{2,3}$=10.2 Hz, H-2), 5.45 (d, 1H, $J_{3,4}$=3.3 Hz, H-4), 5.19 (dd, 1H, $J_{3,4}$=3.3 Hz, $J_{2,3}$=10.2 Hz, H-3), 4.15 (m, 3H, H-5, 2H-6), 3.82 (s, 3H,

OMe), 2.60 (m, 2H, CH$_2$), 2.15, 2.00, 1.97 (3s, 9H, 3Ac), 1.90 (m, 2H, CH$_2$), 1.13 (s, 6H, 2Me).

$^{13}$CNMR (CDCl$_3$): δ=195.81, 176.12, 170.07, 169.93, 169.27, 151.52, 151.27, 150.22, 144.09, 136.98, 136.62, 130.03, 123.36, 119.12, 118.89, 93.73 (C-1).

3'-methoxy-2'-pyridyl-2,3-di-O-acetyl-6-O-(2,2-dimethyl-4-thiopyridyl-carbonylbutyryl)-2-azido-2-deoxy-β-D-galactopyranoside

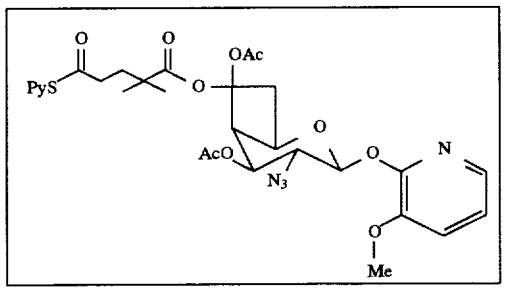

The same procedure described above was followed. 50% yield. [α]$_D$=$^1$HNMR (CDCl$_3$): δ=8.62 (m, 1H, SPy-H-6'), 7.14 (dd, 1H, J$_{4'',6''}$=1.5 Hz, J$_{4'',5''}$=7.8 Hz, Py-H-4"), 6.97 (dd, 1H, J$_{5'',6''}$=4.8 Hz, Py-H-5"), 6.11 (d, 1H, J$_{1,2}$=8.7 Hz, H-1), 5.41 (d, 1H, J$_{3,4}$=3.3 Hz, H4), 5.00 (dd, 1H, J$_{3,4}$=3.3 Hz, J$_{2,3}$=10.8 Hz, H-3), 4.13 (m, 4H, H2, H5, 2H-6), 3.87 (s, 3H, OMe), 2.63 (m, 2H, CH$_2$), 2.16, 2.08 (2s, 6H, 2Ac), 1.90 (m, 2H, CH$_2$), 1.14 (s, 6H, 2Me)

at 100° C. for 5 h. After being cooled to room temperature, the mixture was filtered. The resin was washed with DMF (3×), H$_2$O (3×), MeOH (3×) and Et$_2$O (3×), then dried in vacuo overnight (1.162 g) IR Umax: 1770, 1720 cm$^{-1}$.

Aminomethylpolystyrene

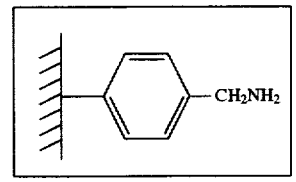

A mixture of 1.162 g of the resin obtained above, 1.2 ml of hydrazine hydrate and 10 ml of EtOH was refluxed for 6 h. After the mixture was cooled to room temperature, the resin was filtered, washed with H$_2$O (2×), MeOH (3×), CH$_2$Cl$_2$ (3×), and Et$_2$O (3×), and dried in vacuo for 24 h (0.953 g). IR bands at 1770 and 1720 cm$^{-1}$n were absent.

general procedure for attachment

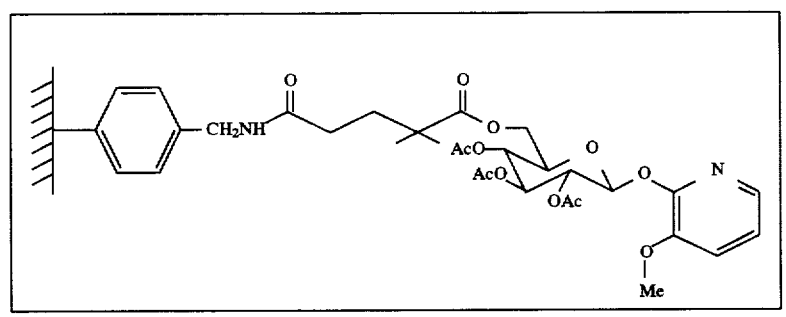

Phthalimidomethylpolystyrene

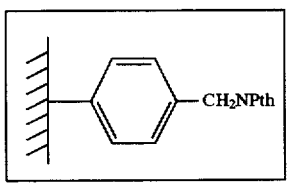

1.108 g of chloromethylpolystyrene cross-linked with 1% divinylbenzene (Merrifield resin, –1 meq. Cl/g) was suspended in 10 ml of dry DMF. 330 mg (1.78 mmol) of potassium phthalimide was added. The mixture was heated A suspension of 790 mg of resin (aminomethylpolystyrene), 800 mg (1.23 mmol) of 3'-methoxy-2'-pyridyl 2,3,4-tri-O-acetyl-6-O-(2,2-dimethyl-4-thiopyridyl-carbonylbutyryl)-β-D-glucopyranoside in 15 ml of dry CH$_2$Cl$_2$ was stirred at room temperature under argon for 30 h. The mixture was filtered, and the resin was washed with CH$_2$Cl$_2$ (4×) and MeOH (4×). The obtained resin was dried in vacuo overnight, then treated with 1.5 ml of Et$_3$N/1 ml of Ac$_2$O in 10 ml of DMF for 4 h. Filtration, washing with DMF, CH$_2$Cl$_2$ (4×), MeOH (4×) and CH$_2$Cl$_2$, and drying in vacuo for 24 h provided 1.219 g of resin.

IR Umax: 1760, 1680 cm$^{-1}$.

general procedure for activation of polymer-bound glycosyl donor

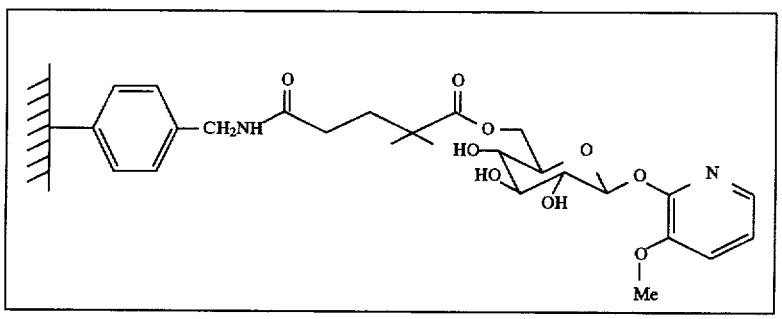

A suspension of 1.0167 g of resin in 18 ml of half-saturated NH$_3$/MeOH solution and 4 ml of CH$_2$Cl$_2$ was stirred at room temperature for 16 h. Filtration and washing with MeOH (3×) and CH$_2$Cl$_2$ (3×) gave the resin which was dried overnight in vacuo. The same procedure was repeated and washed in the same manner. 919.4 mg of dry resin was obtained.

IR Umax: 3400, 1730, 1670 cm$^{-1}$; 1760 cm$^{-1}$ (absent) general procedure for cleavage (Estimation of the amount of glycosyl donor attached to the polymer)

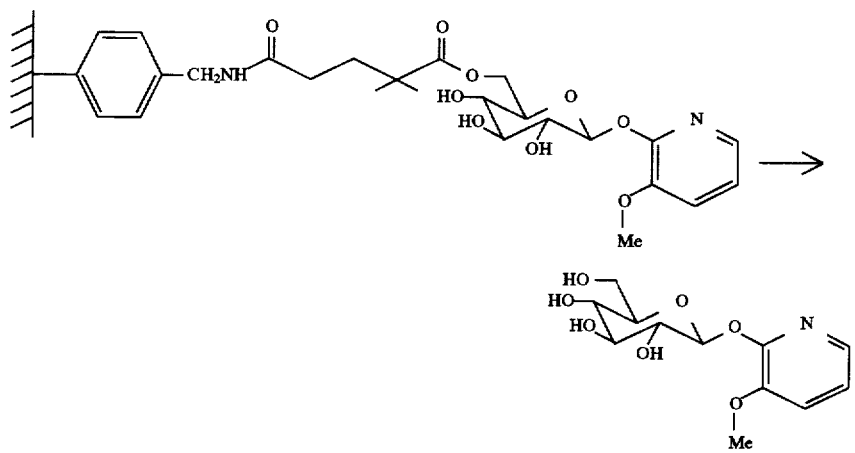

40 mg of activated resin was treated with 0.6 ml of 0.02M NaOMe solution in MeOH/CHCl$_2$ (1:1) with stirring for 15 h. The resin was filtered and washed with MeOH (3×). The filtrate was neutralized with ion-exchange resin (Amberlite 120R), concentrated to provide 8.7 mg (0.0303 mmol) of pure 3'-methoxy-2'-pyridyl β-D-glucopyranoside (−0.76 mmol donor/g of resin).

glycosylation in solid-phase using iso-PrOH as acceptor

To a suspension of 40 mg of polymer-bound glycosyl donor (0.76 mmol donor/g) in 0.4 ml of dry CH$_3$NO$_2$ and 0.4 ml of iso-PrOH was added 28 μl of 1M -MeOTf solution in CH$_3$NO$_2$. The mixture was stirred vigorously at room temperature for 1 h under argon. After addition of one drop of pyridine, the resin was filtered, washed with CH$_3$NO$_2$, MeOH (2×) and CH$_2$Cl$_2$, and dried in vacuo. The obtained resin was treated with 0.4 ml of 0.02M NaOMe solution in MeOH/CH$_2$Cl$_2$ (1:1) for 15 h. The mixture was filtered and washed with MeOH and CH$_2$Cl$_2$. The filtrate was neutralized with ion-exchange resin (Amberlite 120R), and concentrated to provide 6.8 mg of product in quantitative yield (α: β, 7.6:1), (physical data: see the experimental section for solution chemistry.)

glycosylation in solid-phase using diacetone-D-galactose as acceptor

To a mixture of 40 mg of polymer-bound glycosyl donor (0.76 mmol/g), 806 mg of acceptor, 0.4 ml of dry CH$_3$NO$_2$ was added 20 μl of 1M MeOTf solution in CH$_3$NO$_2$. The resulting suspension was vigorously stirred at room temperature for 1 h. After addition of one drop of pyridine, the mixture was filtered and washed with CH$_2$Cl$_2$ and MeOH. The obtained resin was dried in vacuo for 1 h, then treated with with 0.4 ml of 0.02M NaOMe solution in MeOH/CH$_2$Cl$_2$ (1:1) overnight. After filtration and washing with MeOH and CH$_2$Cl$_2$, the filtrate was neutralized with ion-exchange resin (Amberlite 120R) and concentrated to give 10.4 mg crude disaccharide which was purified by flash chromatography on a short silica gel column eluted by MeOH/CHCl$_3$/EtOAc (1:2:2) to give 8 mg of pure compound in 62% yield (α: β, 4:1) (physical data: see the experimental section for solution chemistry.)

glycosylation in solid-phase using 3'-methoxy-2'-pyridyl 2,3,4-tri-O-p-fluoro-benzoyl-6-O-(2,3,4-tri-O-p-fluoro-benzoyl-β-D-glucopyranosyl)-β-D-glucopyranoside as acceptor

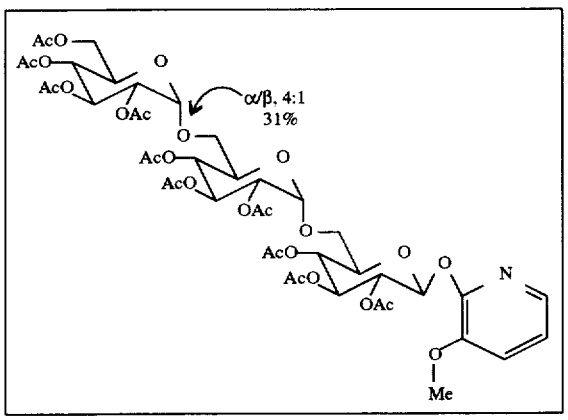

The same procedure described above was followed using 20 equiv. of acceptor, and the desired peracetyated trisaccharides were obtained by flash chromatography on silica gel column using $CH_2Cl_2/MeOH$ (40:1) as the irrigant in 31% yield (α: β, 4:1. seperable).

α-anomer: $[α]_D$=+86.7° (c 0.3, $CHCl_3$)

$^1$HNMR ($CDCl_3$): δ=7.77 (br.d, 1H, J=4.6 Hz, Py-H-6), 7.14 (br.d, 1H, J=7.7 Hz, Py-H-4), 6.95 (dd, 1H, J=4.6 Hz, 7.7 Hz, Py-H-5), 6.17 (, 1H, $J_{1,2}$=7.8 Hz, H-1), 5.42 (t, 1H, J=9.6 Hz), 5.41 (t, 1H, J=9.6Hz), 5.36(t, 1H, J=9.5 Hz), 5.31 (t, 1H, J=9.6 Hz), 5.17 (t, 1H, J=9.6 Hz), 5.08 (d, 1H, $J_{1',2'}$=3.7 Hz, H-1'), 4.98 (d, 1H, $J_{1'',2''}$=3.8 Hz, H-1''), 4.99–5.06 (m, 2H), 4.83 (dd, 1H, J=3.7 Hz, 10.3 Hz, H-2'), 4.78 (dd, 1H, J=3.8 Hz, 10.3 Hz, H-2''), 4.20 (dd, 1H, J=4.3 Hz, 12.4 Hz, H-6''a), 4.09 (dd, 1H, J=2.4 Hz, 12.4 Hz, H-6''b), 3.91–3.99 (m, 3H, H-5, H-5', H-5''), 3.83 (s, 3H, OMe), 3.77 (dd, 1H, J=5.6 Hz, 11.3 Hz, H-6a), 3.61 (dd, 1H, J=2.5 Hz, 11.3 Hz, H-6b), 3.42 (m, 2H, 2H-6'), 2.13, 2.10, 2.09, 2.08, 2.04, 2.03, 2.01, 1.98, 1.97 (9s, 30H, 10Ac).

$^{13}$CNMR ($CDCl_3$): δ=95.76 (C-1''), 95.57 (C-1'), 93.54 (C-1).

MS (FAB): m/z 1054.1 ($M+Na^+$).

β-anomer: $[α]_D$=+40° (c 0.2, $CHCl_3$). $^1$HNMR ($CDCl_3$): δ=7.77 (dd, 1H, J=4.8 Hz, 1.5 Hz, Py-H-6), 7.12 (dd, 1H, J=7.8 Hz, 1.5 Hz, Py-H-4), 6.95 (dd, 1H, J=4.8 Hz, 7.8 Hz, Py-H-5), 6.15 (d, 1H, $J_{1,2}$=7.8 Hz, H-1), 5.41 (t, 1H, J=9.6Hz) 5.35 (t, 1H, J=9.5 Hz), 5.30 (t, 1H, J=9.6 Hz), 5.21 (t, 1H J=9.7 Hz), 5.18 (t, 1H, J=9.5 Hz), 5.06 (t, 1H, J=9.6 Hz), 5.04 (d, 1H, $J_{1',2'}$=3.7 Hz. H-glycosylation in solid-phase using 3'-methoxy-2'-pyridyl 2,3,-4-tri-O-p-fluorobenzoyl-β-D-glucopyranoside as acceptor

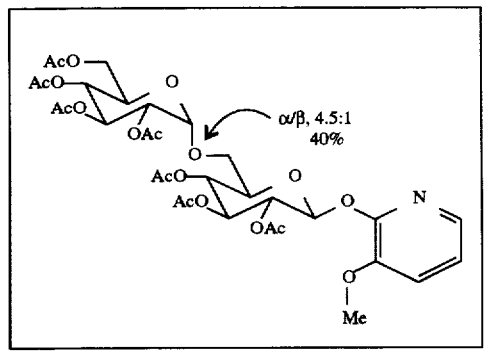

To a mixture of 60 mg of polymer-bound glycosyl donor (0.76 mmol/g) 596 mg (0.908 mmol) of acceptor and 0.6 ml of dry DMF was added 16 μl of HOTf. The resulting suspension was stirred at room temperature for 6 h under argon. After addition of two drops of $^iPr_2NEt$, the mixture was filtered and the resin was washed with MeOH and $CHCl_2$. The filtrate was concentrated, then purified by flash chromatography on column to recover about 78% of acceptor. After being dried in vacuo for 24 h, the resin was glycosylated again under the same condition, washed and dried in the same manner. IR spectra of finally obtained resin indicated the highly increased intensity of ester group bands at 1740 $cm^{-1}$. The disaccharide-containing polymaer was treated with 1 ml of 0.04M of NaOMe solution in MeOH for 24 h, followed by filtration and concentration of the filtrate to afford the residue which was subjected to acetylation ($Ac_2O/Py$) overnight. After usual work up, 15.5 mg of acetylated disaccharide was obtained by purification by flash column chromatography using EtOAc/hexane (2:1–3:1) as the irrigant in 46% yield (α: β4.5:1, unseparable)

α-anomer (an authentic sample prepared by other method): $[α]_D$=+74.7° (c 0.86, $CHCl_3$).

$^1$HNMR ($CDCl_3$): δ=7.76 (dd, 1H, J=4.8 Hz, 1.5 Hz, Py-H-6), 7.12 (dd, 1H, J=7.8 Hz, 1.5 Hz, Py-H-4), 6.93 (dd, 1H, J=4.8 Hz, 7.8 Hz, Py-H-5), 6.18 (d, 1H, $J_{1,2}$=7.8 Hz, H-1), 5.42 (t, 1H, J=9.9 Hz, H-3'), 5.34 (m, 2H, H-2, H-4), 5.07 (t, 1H, J=9.9 Hz, H-3), 5.01 (d, 1H, $J_{1',2'}$=3.6 Hz, H-1'), 4.97 (t, 1H, J=9.9 Hz, H-4'), 4.84 (dd, 1H, J1'2'=3.6 Hz, J2',3'=10.2 Hz, H-2'), 3.98 (m, 2H), 3.83 (s, 3H, OMe), 3.64–3.78 (m, 4H), 2.10, 2.08, 2.04, 2.03, 2.00, 1.99, 1.95 (7s, 21H, 7Ac).

$^{13}$CNMR ($CDCl_3$): δ=95.81 (C-1'), 93.22(C-1).

MS(FAB): m/z 744.1 ($M+H^+$), 684.1, 619.0 1'), 4.96 (dd, 1H, J=8.0 Hz, 9.6 Hz), 4.91 (dd, 1H, J=9.4 Hz, 10.2 Hz), 4.80 (dd, 1H, J=3.8 Hz, 10.2 Hz, H-2'), 4.42 (d, 1H, $J_{1'',2''}$=7.9 Hz, H-1'').

4.27 (dd, 1H, J=4.8 Hz, 12.3 Hz, H-6''a), 4.12 (dd, 1H, J=2.4 Hz, 12.3 Hz, H-6''b), 3.83 (s, 3H, OMe), 3.58–3.93 (m, 6H), 3.26b (dd, 1H, J=5.4 Hz, 11.1 Hz), 2.11, 2.09, 2.08, 2.04, 2.02, 2.01, 2.00, 1.99, 1.98, 1.96 (10s, 30H, 10Ac).

$^{13}$CNMR ($CDCl_3$): δ=100.72 (C-1''), 95.73 (C-1'), 93.57 (C-1).

MS (FAB): m/z 1054.1 ($M+Na^+$), 1032.1 ($M+H^+$).

The above noted examples and illustrations are illustrative only in nature and not limiting.

As those skilled in the art would realize these preferred illustrated details can be subjected to substantial variation, modification, change, alteration, and substitution without affecting or modifying the function of the illustrated embodiments.

This invention is not limited to the embodiments described above, and it will be apparent to persons skilled in the art that numerous modifications and variations form part of the present invention insofar as they do not depart from the spirit, nature and scope of the claimed and described invention.

I claim:

1. In a process of glycoside synthesis comprising reaction of a donor selected from O-pyranosyl and O-furanosyl glycosides, with an acceptor comprising an alcoholic hydroxyl, in the presence of a promoter and a solvent, the improvement comprising selecting said donor from the group consisting of glycosides having aglyconic moieties as leaving groups X having the structure of formula I:

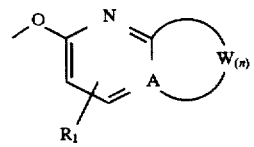

FORMULA I where n is 0 or 1, and W is a fused heterocyclic or biheterocyclic ring with each ring having from 5 to 7 atoms of which up to 2 atoms can be selected independently from the group consisting of S, O or N; when n=0, A is CH, and when n=1, A is C; and R1 is H except where A is CH, alkoxy-alkyl in which the alkoxy and alkyl group contain up to 5 carbon atoms each, or alkoxy of 1 to 5 carbon atoms;
selecting said promoter from the group consisting of MeOTf, TMSOTf, TfOH, BF$_3$, Cu(OTf)$_2$, ZnCl$_2$, Lewis acids, other acids and N-haloimides; and
selecting said solvent from the group consisting of CH$_3$NO$_2$, CH$_2$Cl$_2$, Et$_2$O, CH$_3$CN, DMF, THF, toluene, benzene, dioxane and mixtures thereof.

2. A process of claim 1, wherein said donor is selected from the group consisting of glycosides of formula RX wherein X has formula I, and R has the formula II wherein R2 is azido, acyloxy of 2 to 6 carbon atoms, acylamino of 2 to 5 carbon

FORMULA II atoms, hydroxy, arylcarboxy of 7 to 10 carbon atoms unsubstituted or halogen substituted, arylalkoxy of 7 to 10 carbon atoms, or alkoxy of 1 to 10 carbon atoms; R3 and R4 are independently hydroxy, acyloxy of 2 to 6 carbon atoms, arylcarboxy of 7 to 10 carbon atoms unsubstituted or halogen substituted, arylalkoxy of 7 to 10 carbon atoms, or alkoxy of I to 10 carbon atoms; R5 is independently hydroxy, acyloxy of 2 to 6 carbon atoms, arylcarboxy of 7 to 10 carbon atoms unsubstituted or halogen substituted, arylalkoxy of 7 to 10 carbon atoms, alkoxy of 1 to 10 carbon atoms, trialkylsiloxy wherein the alkyls are independently of 1 to 5 carbon atoms, or R2, R3, R4, R5, may be glycosidyl radicals of formula II;

said promoter is selected from the group consisting of MeOTf, TMSOTf, TfOH, BF$_3$, Cu(OTf)$_2$, and ZnCl$_2$;
said solvent is selected from the group consisting of CH$_3$NO$_2$, CH$_2$Cl$_2$, Et$_2$O, CH$_3$CN, DMF, and THF and mixtures thereof.

3. A process of claim 2, wherein said acceptor is selected from the group consisting of R'OH and glycosides of formula R"Y, wherein R' is alkyl, alkenyl, cycloalkyl, cycloalkenyl, or aralkyl, having from 1 to 27 carbon atoms, N-substituted amino-alcohols, S-substituted thio-alcohols, esters of alkanols of 1 to 10 carbon atoms with hydroxyalkanoic acids of 2 to 6 carbon atoms, esters or alkanols of 1 to 10 carbon atoms with hydroxyaminoalkanoic acids of 2 to 6 carbon atoms having the amino function acylated by an acid of 2 to 10 carbon atoms:

FORMULA III containing at least one unprotected alcoholic hydroxyl, where Y is selected from the group consisting of alkoxy of 1 to 12 carbon atoms and X; R7 is azido, hydroxyl, acyloxy of 2 to 6 carbon atoms, arylcarboxy of 7 to 10 carbon atoms unsubstituted or halogen substituted arylalkoxy of 7 to 10 carbon atoms, alkoxy of 1 to 10 carbon atoms, hydrogen, or aminocarbalkoxy of 2 to 10 carbon atoms; R8 is hydrogen, hydroxyl, alkenyloxy of 1 to 5 carbon atoms, acyloxy of 2 to 6 carbon atoms, arylcarboxy of 7 to 10 carbon atoms unsubstituted or halogen substituted, arylalkoxy of 7 to 10 carbon atoms, or alkoxy of 1 to 10 carbon atoms; R9 is hydroxyl, arylcarboxy of 7 to 10 carbon atoms unsubstituted or halogen substituted, arylalkoxy of 7 to 10 carbon atoms, alkoxy of 1 to 10 carbon atoms, or acyloxy of 2 to 6 carbon atoms; R10 is hydroxyl arylalkoxy of 7 to 10 carbon atoms, or alkoxy of 1 to 10 carbon atoms. Y and R7 may together be alkylidenyldioxy of 3 to 9 carbon atoms, or cycloalkylidenyldioxy of 5 to 10 carbon atoms, or R8 and R9 may together be alkylidenyldioxy of 3 to 9 carbon atoms, or cycloalkylidenyldioxy of 5 to 10 carbon atoms or R9 and R10 arylalkylidenyldioxy of 7 to 10 carbon atoms or R7, R8, R9, R10 may be glycosidyl radicals of formulae II or III.

4. A process of claim 3, wherein X is 3-methoxy-pyridyl-2-oxy.

5. A process of claim 4, wherein R has formula IV:

FORMULA IV

6. A process of claim 4, wherein R has formula V:

FORMULA V where R2 is azido, arylalkoxy of 7 to 10 carbon atoms, or alkoxy of 1 to 10 carbon atoms, R3, R4 and R5 are arylalkoxy of 7 to 10 carbon atoms, or alkoxy of 1 to 10 carbon atoms;

said promoter is Cu(OTf)$_2$;
said solvent is selected from the group consisting of CH$_2$Cl$_2$, Et$_2$O, and mixtures thereof;
said acceptor is selected from the group consisting of glycosides of formula R"Y, containing at least one unprotected alcoholic hydroxyl, wherein Y is alkoxy of 1 to 12 carbon atoms; R7 is hydroxy, acyloxy of 2 to 6 carbon atoms, or aminocarbalkoxy of 2 to 10 carbon atoms; R8 is hydrogen, hydroxyl, acyloxy of 2 to 6 carbon atoms arylalkoxy of 7 to 10 carbon atoms, or alkoxy of 1 to 10 carbon atoms; R9 is hydroxyl, or acyloxy of 2 to 6 carbon atoms, R10 is hydroxyl arylalkoxy of 7 to 10 carbon atoms, or alkoxy of 1 to 10 carbon atoms; R9 and R10 may together be aralkylidenyldioxy of 7 to 10 carbon atoms.

7. A process of claim 3, wherein R2, R3 and R4 are independently hydroxy, arylalkoxy of 7 to 10 carbon atoms, or alkoxy of 1 to 10 carbon atoms; R5 is independently hydroxy, arylalkoxy of 7 to 10 carbon atoms, alkoxy of 1 to 10 carbon atoms or trialkylsiloxy, wherein the alkyls are independently of 1 to 5 carbon atoms, or R2, R3, R4, R5 may be glycosidyl radicals of formula II, and at least one of R2, R3, R4 and R5 is hydroxyl;

said promoter is selected from the group consisting of MeOTf, TMSOTf, BF$_3$, Cu(OTf)$_2$, and ZnCl$_2$;
said solvent is selected from the group consisting of CH$_3$NO$_2$, CH$_2$Cl$_2$, CH$_3$CN, DMF and THF and mixtures thereof.

8. A process of claim 6, wherein R2, R3, R4 and R5 are hydroxyl.

9. A process of claim 4, wherein R2, R3, R4 and R5 are arylalkoxy of 7 to 10 carbon atoms, or alkoxy of 1 to 10 carbon atoms;

said promoter is selected from the group consisting of MeOTf and Cu(OTf)$_2$;

said solvent is selected from the group consisting of $CH_3NO_2$, $CH_2Cl_2$, $Et_2O$, $CH_3CN$ and DMF and mixtures thereof.

10. A process of claim wherein said acceptor is selected from the group consisting of alkanols of 1 to 12 carbon atoms and glycosides of formula R"Y, containing at least one unprotected alcoholic hydroxyl, wherein Y is selected from the group consisting of alkoxy of 1 to 12 carbon atoms and 3-methoxy-pyridyl-2-oxy; R7 is azido, hydroxyl, acyloxy of 2 to 6 carbon atoms, arylcarboxy of 7 to 10 carbon atoms unsubstituted or halogen substituted, arylalkoxy of 7 to 10 carbon atoms, alkoxy of 1 to 10 carbon atoms, hydrogen or aminocarbalkoxy of 2 to 10 carbon atoms; R8 is hydroxyl, acyloxy of 2 to 6 carbon atoms, arylcarboxy of 7 to 10 carbon atoms unsubstituted or halogen substituted, arylalkoxy of 7 to 10 carbon atoms, or alkoxy of 1 to 10 carbon atoms; R9 is hydroxyl, arylcarboxy of 7 to 10 carbon atoms unsubstituted or halogen substituted, or acyloxy of 2 to 6 carbon atoms, or alkoxy of 1 to 10 carbon atoms; Y and R7 may together be alkylidenyldioxy of 3 to 9 carbon atoms, or R8 and R9 may together be alkylidenyldioxy of 3 to 9 carbon atoms, or R9 and R10 may together be aralkylidenyldioxy of 7 to 10 carbon atoms.

11. A process of claim 4, wherein R2, R3 and R4 are independently acyloxy of 2 to 6 carbon atoms, or arylcarboxy of 7 to 10 carbon atoms unsubstituted or halogen substituted; R5 is independently acyloxy of 2 to 6 carbon atoms, arylcarboxy of 7 to 10 carbon atoms unsubstituted or halogen substituted, and trialkylsiloxy wherein the alkyls are independently of 1 to 5 carbon atoms:

said promoter is $Cu(OTf)_2$;
said solvent is $CH_2Cl_2$.

12. The process of claim 4, wherein R2 is acylamino of 2 to 5 carbon atoms, R3, R4 and R5 are hydroxyl;
said promoter is selected from the group consisting of MeOTf and TfOH;
said solvent is selected from the group consisting of $CH_3NO_2$ and DMF and mixtures thereof.

13. A process of claim 4, wherein R2 is azido, R3 is arylalkoxy of 7 to 10 carbon atoms, alkoxy of 1 to 10 carbon atoms or glycosidyl radicals of formula II, wherein R2, R3, R4 and R5 are acyloxy of 2 to 6 carbon atoms, R4 and R5 are arylalkoxy of 7 to 10 carbon atoms, alkoxy of 1 to 10 carbon atoms, or R4 and R5 together are alkylidenyldioxy of 3 to 9 carbon atoms;
said promoter is $Cu(OTf)_2$;
said solvent is selected from the group consisting of $CH_2Cl_2$, and $CH_3CN$ and mixtures thereof.

14. In a process of glycoside synthesis comprising reaction of a donor selected from O-pyranosyl and O-furanosyl glycosides, with an acceptor comprising an alcoholic hydroxyl, in the presence of a promoter and a solvent, the improvement comprising said donor is selected from the group consisting of glycosides having aglyconic moieties as leaving groups of formula VIII:

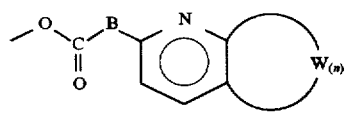

FORMULA VIII where B is O or S, and where n is 0 or 1, and W is a fused heterocyclic or biheterocyclic ring with each ring having from 5 to 7 atoms of which up to 2 atoms can be selected independently from the group consisting of S, O or N;
said promoter is selected from the group consisting of MeOTf, TMSOTf, TfOH, $BF_3$, AgOTf, $Cu(OTf)_2$, $ZnCl_2$, Lewis acids, other acids and N-haloimides;
said solvent is selected from the group consisting of $CH_3NO_2$, $CH_2Cl_2$, $Et_2O$, $CH_3CN$, DMF, THF and mixtures thereof.

15. A process of claim 14, wherein said donor is an O-pyranosyl glycoside:
said promoter is selected from the group consisting of AgOTf and $Cu(OTf)_2$;
said solvent is selected from the group consisting of $CH_3NO_2$, $CH_2Cl_2$, $Et_2O$, $CH_3CN$, DMF, THF and mixtures thereof.

16. A process of claim 15, wherein said donor is selected from the group consisting of glycosides of formula X wherein Z has formula VII:

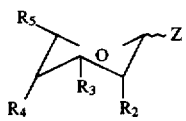

FORMULA X

17. A process of claim 14, wherein said acceptor is selected from the group consisting of glycosides of formula RX wherein X has formula I and R has the formula II:

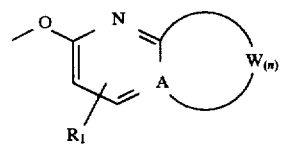

FORMULA I

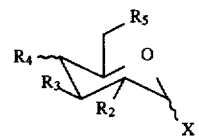

FORMULA II where n is 0 or 1, and W is a fused heterocyclic or biheterocyclic ring with each ring having from 5 to 7 atoms of which up to 2 atoms can be selected independently from the group consisting of S, O or N, A is N, or CH, and R1 is H except where A is CH or alkoxy of 1 to 5 carbon atoms; R2 is azido, acyloxy of 2 to 6 carbon atoms, arylcarboxy of 7 to 10 carbon atoms unsubstituted or halogen substituted, arylalkoxy of 7 to 10 carbon atoms, or alkoxy of 1 to 10 carbon atoms; R3 and R4 are independently hydroxy, acyloxy of 2 to 6 carbon atoms, arylcarboxy of 7 to 10 carbon atoms unsubstituted or halogen substituted, arylalkoxy of 7 to 10 carbon atoms, or alkoxy of 1 to 10 carbon atoms; R5 is independently hydroxy.

18. In a process of nucleoside synthesis comprising reaction of a donor selected from O-pyranosyl and O-furanosyl glycosides, with an acceptor comprising an acylated purine in the presence of bromine or a like oxidizer, and a solvent, the improvement comprising said donor is selected from the group consisting of glycosides having aglyconic moieties as leaving groups of formula VIII:

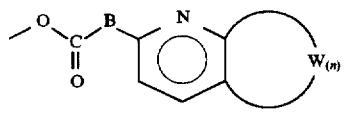

FORMULA VIII where n is 0 or 1, and W is a heterocyclic or biheterocyclic ring with each ring having from 5 to 7 atoms of which up to 2 atoms can be selected independently from the group consisting of S, O or N, and where B is O or S;

said solvent is DMF.

19. A process of claim 18, wherein said purine is 6-benzoyl adenine.

* * * * *